(12) United States Patent
Albert et al.

(10) Patent No.: US 6,686,513 B1
(45) Date of Patent: *Feb. 3, 2004

(54) SUGARCANE UBI9 GENE PROMOTER SEQUENCE AND METHODS OF USE THEREOF

(75) Inventors: Henrik H. Albert, Honolulu, HI (US); Hairong Wei, Honolulu, HI (US)

(73) Assignees: The United States of America as represented by the Secretary of Agriculture, Washington, DC (US); University of Hawaii, Honolulu, HI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/693,467

(22) Filed: Oct. 20, 2000

Related U.S. Application Data

(63) Continuation-in-part of application No. 09/270,976, filed on Mar. 17, 1999.
(60) Provisional application No. 60/078,767, filed on Mar. 19, 1998.

(51) Int. Cl.$^7$ .......................... C12N 5/04; C12N 15/82; C12N 15/90; A01H 5/00
(52) U.S. Cl. ....................... 800/278; 435/411; 435/419; 536/24.1; 800/298
(58) Field of Search ................................ 435/410, 419, 435/468, 411, 412, 414, 415; 536/23.6, 24.1; 800/278, 295, 298, 312, 317.3, 317.4, 320, 320.1, 320.2

(56) References Cited

U.S. PATENT DOCUMENTS

| | | | |
|---|---|---|---|
| 4,683,195 A | 7/1987 | Mullis et al. .................. 435/6 |
| 4,683,202 A | 7/1987 | Mullis ....................... 435/91.1 |
| 4,940,835 A | 7/1990 | Shah et al. .................. 800/278 |
| 4,940,838 A | 7/1990 | Schilperoort et al. ....... 800/278 |
| 4,965,188 A | 10/1990 | Mullis et al. .................. 435/6 |
| 4,971,908 A | 11/1990 | Kishore et al. ............. 435/468 |
| 5,015,580 A | 5/1991 | Christou et al. ............ 435/468 |
| 5,365,015 A | 11/1994 | Grierson et al. ............ 800/278 |
| 5,501,967 A | 3/1996 | Offringa et al. ............ 435/468 |
| 5,510,474 A | 4/1996 | Quail et al. ................. 536/24.1 |
| 5,512,466 A | 4/1996 | Klee et al. .................. 435/468 |
| 5,545,815 A | 8/1996 | Fischer et al. .............. 800/278 |
| 5,584,807 A | 12/1996 | McCabe ....................... 604/71 |
| 5,593,874 A | 1/1997 | Brown et al. ............... 435/468 |
| 5,614,399 A | 3/1997 | Quail et al. ................. 435/468 |
| 5,723,766 A | 3/1998 | Theologis et al. .......... 800/278 |
| 6,054,574 A | 4/2000 | Quail et al. ................. 536/24.1 |

OTHER PUBLICATIONS

Benfey et al "The Cauliflower Mosaic Virus 35S Promoter: combinatorial Regulation of Transcription in Plants", Nov. 1999, Science vol. 250, pp. 959–966.*

Kim et al, "A 20 nucleotide upstream element is essential for the nopaline synthase (nos) promoter activity", 1994, Plant Molecular Biology vol. 24, pp. 105–117.*

Hershko et al. (1992) "The Ubiquitin System for Protein Degradation," Annual Review of Biochem. 61:761–807.

Callis et al. (1995) "Structure and Evolution of Genes Encoding Polyubiquitin and Ubiquitin–Like Proteins in *Arabidopsis thaliana* Ecotype Columbia," Genetics 139:921–939.

Callis et al. (1989) "Ubiquitin and Ubiquitin Genes in Higher Plants," Oxford Surv. Plant Mol. Cell. Biol. 6:1–30.

Sun et al. (1997) "Independent modulation of *Arabidopsis thaliana* polyubiquitin mRNAs in different organs and in response to environmental changes," Plant J. 11:1017–1027.

Kawalleck et al. (1993) "Polyubiquitin gene expression and structure properties of the ubi4–2 gene in *Petroselinum crispum*," Plant Mol. Biol. 21:673–684.

Callis et al. (1994) "Developmentally regulated loss of ubiquitin and ubiquitinated proteins during pollen maturation in maize," Proc. Natl. Acad. Sci. USA 91:6074–6077.

Plesse et al. (1997) "Identification of a new cis–regulatory element in a *Nicotiana tabacum* polyubiquitin gene promoter," Mol. Gen. Genet. 254:258–266.

Christensen et al. (1989) "Sequence analysis and transcriptional regulation by heat shock of polyubiquitin transcripts from maize," Plant Mol. Biol. 12:619–632.

Liu et al. (1995) "Characterization, chromosomal mapping, and expression of different polyubiquitin genes in tissues from control and heat–shocked maize seedlings,"Biochem. Cell. Biol. 73:19–30.

Almoguera et al. (1995) "Differential Accumulation of Sunflower Tetraubiquitin mRNAs during Zygotic Embryogenesis and Developmental Regulation of Their Heat–Shock Response," Plants Physiology 107:765–773.

Binet et al. (1991) "Structure and expression of sunflower ubiquitin genes," Plant Mol. Biol. 17:395–407.

Burke et al. (1988) "Characterization of a polyubiquitin gene from *Arabidopsis thaliana*," Mol. Gen. Genet. 213:435–443.

Garbarino et al. (1992) "Expression of stress–responsive ubiquitin genes in potato tubers," Plant Mol Biol 20:235–244.

(List continued on next page.)

*Primary Examiner*—Ashwin Mehta
(74) *Attorney, Agent, or Firm*—Medlen & Carroll, LLP; Margaret A. Connor

(57) ABSTRACT

The invention relates to the nucleotide sequence from the sugarcane ubi9 polyubiquitin gene promoter, which is capable of directing constitutive expression of a nucleic acid sequence of interest that is operably linked to it. The sugarcane ubi9 promoter is useful in regulating expression of a nucleic acid sequence of interest in monocotyledonous and dicotyledonous plants.

13 Claims, 30 Drawing Sheets

OTHER PUBLICATIONS

Genschik et al. (1994) "Structure and promoter activity of a stress and developmentally regulated polyubiquitin–encoding gene of *Nicotania tabacum*." Gene 148:195–202.

Takimoto et al. (1994) "Non–systemic expression of a stress–responsive maize of polyubiquitin gene (Ubi–1) in transgenic rice plants," Plant Mol Biol 26:1007–1012.

Christensen et al. (1992) "Maize polyubiquitin genes: structure, thermal perturbation of expression and transcript splicing, and promoter activity following transfer to protoplasts by electroporation," Plant Mol Biol 18:675–689.

Garbarino et al. (1995) "Isolation of a Polyubiquitin Promoter and Its Expression in Transgenic Potato Plants," Plant Physiology 109:1371–1378.

Gallo–Meagher et al. (1993) "Effects of Tissue Type and Promoter Strength on Transient GUS Expression in Sugarcane Following Particle Bombardment," Plant Cell Reporter 12:666–670.

Taylor et al. (1993) "Enhanced GUS gene expression in cereal/grass cell suspensions and immature embryos using the maize ubiquitin–based plasmid pAHC25," Plant Cell Reports 12:491–495.

Sreenivasan et al., Cytogenics in *Sugarcane Improvement Through Breeding*, pp. 211–253 Heinz DJ (ed.) Elsevier, Amsterdam (1987).

Albert et al. (1995) "Plant Gene Register PGR95–045, Nucleotide Sequence of a Sugarcane Polyubiquitin cDNA (GenBank L41658)," Plant Physiology 109:337.

Rhodes et al. (1995) "Transformation of Maize by Electroporation of Embyros," Methods Mol. Biol. 55:121–131.

Wigler et al., (1980) "Transformation of mammalian cells with an amplifiable dominant–acting gene," Proc. Natl. Acad. Sci. 77:3567–3570.

Colbere–Garapin et al., (1981) "A New Dominant Hybrid Selective Marker for Higher Eukaryotic Cells," J. Mol. Biol. 150:1–14.

Caruthers et al. (1980) "New chemical methods for synthesizing polynucleotides," Nuc. Acids Res. Symp. Ser. 215–223.

Horn et al. (1980) "Synthesis of oligonucleotides on cellulose. Part II: design and synthetic strategy to the synthesis of 22 oligodeoxynucleotides coding for Gastric Inhibitory Polypeptide (GIP)[1]," Nuc. Acids Res. Symp. Ser. 225–232.

Worrell et al. (1991) "Expression of a Maize Sucrose Phosphate Synthase in Tomato Alters Leaf Carbohydrate Partitioning," Plant Cell 3:1121–1130.

Mariani et al. (1990) "Induction of male sterility in plants by a chimaeric ribonuclease gene," Nature 347: 737–741.

Picton et al. (1993) "Altered fruit ripening and leaf senescence in tomatoes expressing an antisense ethylene–forming enzyme transgene," Plant J. 3:469–481.

Shahar et al. (1992) "The Tomato 66.3–kD Polyphenoloxidase Gene: Molecular Identification and Developmental Expression," Plant Cell 4:135–147.

Bachem et al. (1994) "Antisense Expression of Polyphenol Oxidase Genes Inhibits Enzymatic Browning in Potato Tubers," Bio/Tech 2:1101–1105.

Hooykas–Van Slogteren et al. (1984) "Expression of Ti plasmid genes in monocotyledonous plants infected with *Agrobacterium tumefaciens*," Nature 311:763–764.

Klee et al. (1987) "Agrobacterium–Mediated Plant Transformation and Its Further Applications to Plant Biology," Ann. Rev. Plant Phys. 38:467–486.

Bidney et al. (1992) "Microprojectile bombardment of plant tissues increases transformation frequency by *Agrobacterium tumefaciens*," Plant Molec. Biol. 18:301–313.

Nan et al. (1995) in *Biotechnology in Agriculture and Forestry*, ed., Y.P.S. Bajaj, Springer–Verlag Berlin Heidelberg, vol. 34:145–155.

Griesbach (1992) "Incorporation of the Gus Gene into Orchids via Embryo Electrophoresis," Hort Science 27:620.

Fraley et al. (1982) "Liposome–mediated delivery of tobacco mosaic virus RNA into tobacco protoplasts: A sensitive assay for monitoring liposome–protoplast interactions," Proc. Natl. Acad. Sci. USA 79:1859–1863.

Krens et al. (1982) "In vitro transformation of plant protoplasts with Ti–plasmid DNA," Nature 296:72–74.

Albert et al. (1992) "Structure and expression of a sugarcane gene encoding a housekeeping phosphoenolpyruvate carboxylase." Plant Mol Biol 20:663–671.

Moore, Anatomy and Morphology in *Sugarcane Improvement Through Breeding*, pp. 85–142, Heinz DJ (ed) Elsevier, Amsterdam (1987).

Church et al. (1984) "Genomic sequencing," Proc. Natl. Acad. Sci. USA 81:1991–1995.

Feinberg, A.P. and Voglestein, B. (1983) "A Technique for Radiolabeling DNA Restriction Endonuclease Fragments to High Specific Activity," Anal. Biochem. 132:6–13.

Bugos et al. (1995) "RNA Islation from Plant Tissues Recalcitrant to Extraction in Guanidine," Biotechniques 19:734–737.

Fourney et al. (1988) "Northern Blotting: Efficient RNA Staining and Transfer," Focus 10:5–7.

Virca et al. (1990) "Simplified Northern Blot Hybridization Using 5% Sodium Dodecyl Sulfate," BioTechniques 8:370–371.

Scharf et al., Heat stress promoters and transcription factors in *Plant Promoters and Transcription Factors*, pp. 125–162, L. Nover (ed), Springer–Verlag, Berlin (1994).

Bugos et al. (1993) "Glucose Transporter cDNAs from Sugarcane," Plant Physiol. 103:1469–1470.

Wessler et al. (1995) "LTR–retrotransposons and MITEs: important players in the evolution of plant genomes," Curr. Opin. Genet. Dev. 5:814–821.

Norris et al. (1993) "The intron of *Arabidopsis thaliana* polyubiquitin genes is conserved in location and is a quantitative determinant of chimeric gene expression," Plant Mol. Biol. 21:895–906.

Jefferson et al. (1986) "β–Glucuronidase from *Escherichia coli* as a gene–fusion marker," Proc. Natl. Acad. Sci. USA 83:8447–8451.

Christensen et al. (1996) "Ubiquitin promoter–based vectors for high–level expression of selectable and/or screenable marker genes in monocotyledonous plants," Transgenic Research 5:213–218.

Roberts et al. (1997) "A comprehensive new set of modular vectors to allow both routine and advanced manipulations and efficient transformation of rice by both Agrobacterium and direct gene–transfer methods," CAMBIA Vectors, Rockefeller Foundation Meeting of the International Program on Rice Biotechnology, Malacca, Malaysia.

Nickell et al. (1969) "Growth of Suspension Cultures of Sugarcane Cells in Chemically Defined Media," Physiol. Plant. 22:117–125.

Klein et al. (1987) "High–velocity microprojectiles for deliverying nucleic acids into living cells," Nature 327:70–73.

Bradford (1976) "A Rapid Sensitive Method for the Quantitation of Microgram Quantities of Protein Utilizing the Principle of Protein–Dye Binding," Anal. Biochem. 72:248–254.

Hood et al. (1986) "The Hypervirulence of *Agrobacterium tumefaciens* A281 Is Encoded in a Region of pTiBo542 Outside of T–DNA," J. Bacteriol. 168:1291–1301.

Hiei et al. (1994) "Efficient transformation of rice (*Oryza sativa* L.) mediated by Agrobacterium and sequence analysis of the boundaries of the T–DNA," Plant J. 6:271–282.

Horsch et al. (1985) "A Simple and General Method for Transferring Genes into Plants," Science 227:1229–1231.

Wei et al. (1999) "Differential Expression of Sugarcane Polyubiquitin Genes and Isolation of Promoters from two Highly–Expressed Members of the Gene Family," J. Plant Physiol. 155:513–519.

Dong and Hall (1996) "Agrobacterium–mediated transformation of Javanica rice," Molecular Breeding 2:267–276.

Kumpatla et al. (1997) "Epigenetic Transcriptional Silencing and 5–Azacytidine–Mediated Reactivation of a Complex Transgene in Rice," Plant Physiol. 115:361–373.

Wei and Albert "Differential Expression of Sugarcane Polyubiquitin Genes," 1997 CTAHR Student Research Symposium.

Wei and Albert "Isolation of a Strong Gene Promoter for Genetic Engineering," (1996) HSPA and HARC Annual Report, pp 24–25.

Albert et al. "Cloning of Polyubiquitin Genes From Sugarcane," 1994 Hawaiian Sugar Planters' Annual Report, p. 5.

Wei et al., "Isolation and Characterization of Two Strong Sugarcane Polyubiquitin Gene Promoters for Genetic Engineering of Agriculturally Important Crops," Poster, Oct. 1999, Hawaii Sugarcane Technology.

Cornejo et al. (1993) "Activity of a maize ubiquitin promoter in transgenic rice," Plant Mol. Biol. 23:567–581.

Watt et al. (1997) "UB14, the polyubiquitin gene of *Saccharomyces cerevisiae$_2$* is a heat shock gene that is also subject to catabolite derepression control," Mol. Gen. Genet. 253:43–447.

* cited by examiner

FIGURE 3A

```
   1 GAATTCATTA TGTGGTCTAG GTAGGTTCTA TATATAAGAA AACTTGAAAT
  51 GTTCTAAAAA AAAATTCAAG CCCATGCATG ATTGAAGCAA ACGGTATAGC
 101 AACGGTGTTA ACCTGATCTA GTGATCTCTT GCAATCCTTA ACGGCCACCT
 151 ACCGCAGGTA GCAAACGGCG TCCCCCTCCT CGATATCTCC GCGGCGACCT
 201 CTGGCTTTTT CCGCGGAATT GCGCGGTGGG GACGGATTCC ACnAnACCGC
 251 GACGCAACCG CCTCTCGCCG CTGGGCCCCA CACCGCTCGG TGCCGTAGCC
 301 TCACGGGACT CTTTCTCCCT CCTCCCCCGT TATAAATTGG CTTCATCCCC
 351 TCCTTGCCTC ATCCATCCAA ATCCAGTCC CCAATCCCAT CCCTTCGTCG
 401 GAGAAATTCA TCGAAGCGAA GCGAATCCTC GCGATCCTCT CAAGGTACTG
 451 CGAGTTTTCG ATCCCCTCT CGACCCCTCG TATGTtTGTG TTTGTCGTAC
 501 GTTTGATTAG GTATGCTTTC CCTGTTTGTG TTCGTCGTAg CGTTTGATTA
 551 GGTaTGCTTT CCCTGTTCGT GTTCATCGTA GTGTTTGATT AGGTCGTGTG
 601 AGGCGATGGC CTGCTCGCGT CCTTCGATCT GTAGTCGATT TGCGGGTCGT
 651 GGTGTAGATC TGCGGGCTGT GATGAAGTTA TTTGGTGTGA TCTGCTCGCC
 701 TGATTCTGCG GGtTGGCTCG AGTAGATATg GATGGTTGGA CCGGTTGGTT
 751 CGTTTACCGC GCTAGGGTTG GGCTGGGATG ATGTTGCATn GCGCCGTTGC
 801 GCGTGATCCC GCAGCAGGAC TTGCGTTTGA TTGCCAGATC TCGTTACGAT
 851 TATGTGATtT GGTTTGGACT TATTAGATCT GTAGCTTCTG cTTATGtTGC
 901 CAGAtGCGCC TACTGCTcCA TATGCCTGAT GATAATcCAT AAATGGCAGT
 951 GGAAATCAAC TAGTTGATTG CGGAGTCATG TATCAGCTAC AGGTGTAGGG
1001 ACTAGCTACA GGTGTAGGGA CTnGCGTCTA ATTGTTTGGT CCTTAACTCA
1051 TGTGCAATTA TGCAATTTAG TTTAGATGTT TGTTCCAAnT CATCTAGGCT
1101 GTAAAGGGA CACTGGTTAG ATTGCTGTTT AATCTTTTA GTAGATTATA
1151 TTATATTGGT AACTTATTAA CCCnTATTAA CATGCCATAA CGTGGATTCT
1201 GCTCATGCCT GATGATAATC ATAGATCACT GTGGAATTAA TTAGTTGATT
```

1251 GTTGAATCAT GTTTCATGTA CATACCACGG CACAATTGCT TAGTTCCTTA

1301 ACAAATGCAA ATTTTACTGA TCCATGTATG ATTTGCGTGG TTCTCTAATG

1351 TGAAATACTA TAGCTACTTG TTAGTAAGAA TCAGGTTCGT ATGCTTAATG

1401 CTGTATGTGC CTTCTGCTCA TGCCTGATGA TAATCATATA TCACTGGAAT

1451 TAATTAGTTG ATCGTTTAAT CATATATCAA GTACATACCA TGGCACAATT

1501 TTTAGTCACT TAACCCATGC AGATTGAACT GGTCCCtGCA TGTTTtGCTA

1551 AATTGTTcTA TTCtGAttAG ACcATATATC AggTATtTTt TTtTGGTAat

1601 GGTTcTcTTA TtTtaAAtGc tAtATAGTTc tGGtACTtGT TAGAAaGATc 1651 tGgTtncATA GTTTAGttGC CTATCCtTcG AaTTAGGAtG cTGAGCAGCt 1701 GATCCTATAG cTTTGTTTCA TGtATCaATt cTTTTGtGTT CAACAGTCAG 1751 TTtTtGTTAG AtTCAttGTA ACTTATGTTC GCTTAcTCTT CTGGTCCTCa 1801 ATGCTtGcAG ATG

```
   1 TAATCCTGGG CCATGAnCAG CTGTCCTTCC AGGTTCACAA GTCTGGTGCC
  51 TTCTTCTGTC CCTCCGATGG AGATTATCTG CATGTCGTGG TCGTGTCCTG
 101 ATCGAATCCT CgTTGAATCC CTATgTTTTT CTTCAAGAAA TGTGAgTCCT
 151 ATgTCAgTCT GGTTGCGTTT GTGAACATTt CTGCTGCTGA gCAgCACTTt
 201 GGCTGGAAcT GTGCAATGAA ATAAATGGAA CCCTGGTTTC TGGTTATGTG
 251 TGTGTTAGCT AATGTTTTTG AAGTGGAAGC TCTAATCTTC TATCGCGTTG
 301 CTACTACAAT TCTGCTTGTG TTTTGATGGT TCTTGGTTTC TGTTAGTTGG
 351 TTCAGAGGAA GTTTTGCTTC CACAGACTAA GATGCAGTTG AACTTTGGTT
 401 GCCCTGGTTT CTAGATTTCA TTTGTGCTGG TTGAGTGATA GTAAGAAACA
 451 ACCGGTGTTC ACATATAATC AGGTTTTGTG CTGCTCGAGT GATCGTCAAA
 501 AACCACCGGT GTTCACATCT AAAAGGTTT CGATCCCCAG GTTTAGATCT
 551 CCCGTTTAAT TCCAAAAAAA AGTTCTGTG TACTTGCATT TAGTTGGGTG
 601 GTTGATGCTG GAAAGAgTAA CTTTCAAGAg TAATAATCTT TGGTGACTAC
 651 TCTGTTTCAA CTGATCAATC CCTAGGAAAG GTACACCTTT ACTTAGGGAA
 701 GAAAtTCtTA GAACCTTGCA CTTTGTTTCA ACTGATAATA GTATACtTTA
 751 TTAgATAAAA AATAtTCAGA TATATTAgAC ACCGGATGTC ATCCACTCAT
 801 CCTTACAAAC CTCTGTCATG GTCCTGCAGA AATGTTTGCC AGCTCCAGTG
 851 GCTTCCTGAT AAATCTGTGG AGTGCCTGTT AATCnGCTGC CAATTTTTGC
 901 TGAGCACTGT ATATATGTTA GTAAGTACTA TTGGGCCACC AATTCCATTT
 951 TGACACAGCA CTATTGGTCC ACCAATTCGA TCCTGACACA GCACTGCATA
1001 ATTTGAAACG TTTTTGCTcC CATTTTGCAA gGCTACaAAT TTAgATCATG
1051 TTTAsCATyC TGTGGGATAC aATATATGGA TATCGAACaA ACTTGGTATG
1101 TCAGAGAAAA AATAgTTTAt TTTCAaAACT AACATTTTta AAgCCTTCTA
1151 tGaACTTtaA ACCTTCAgCA TTtgGGATCa AgAtgAGTGC tCGAACAAgA
1201 GTGCaCTTTT TCTCCAAAAT aATCtACtAC agAGTTCTTT TTTATaTATa
1251 aaAAAACTTA TACTTAACAG ATAAATCAGA CCTCTTCTGC TCCATATCAC
```

FIGURE 3B (continued)

```
1301  CTTGACAAAT CAAAGAAGCA GCACCAGCGA AGGGTATTAT TATTGAGGTA
1351  AATATAAGAT CTCGTTTACT GAAAAAGACC GCGTGTTTAC CTAAACTACC
1401  ATTTTGCTTT GATAGCAGCA TACATGTGAT AGAATTGCGG ATCCTACCGT
1451  GCTGACTGTG AAnGTGGTAA GGGTGAgAgA TTGgTgGGCG AgGTcTGAAC
1501  GAgCGAAAAC AGtACTGCAT TTAcTGTTCA CAAgGAGGCG GcTTAGGTTT
1551  TGGTCTCCCA gcTcTcTAAG GGAAGCTGAG AATTATGATT cTCTTGCtTA
1601  ATTATTTCTT AACCAAAGTT aTAAAtATAT AgCcTaTGAg ATCcTAATTT
1651  ATGGAAATAA CTAAACTATT TTAAGGAAAT ATATAAATAG ATAATCAGCC
1701  CACTAAtGGG CnTAGCGCCC ACTAACAGGC CTGGTGCTGA GCCCGACATA
1751  ACATCTCTCC CcGCcTGGrG AAAcAGCTcg TCcTcGaGcT GAAATCtGGT
1801  AGAAGCATCw TCAaCCAACA CCGGGGTcAT GcTGGAAcAc TGcATCAGGC
1851  GcTACcGCAG CTGgTACgTC gTCGTCGAGG AaGTCAgCCG AcTCcAAGTA
1901  GAACAGTCGC TTACAacTGA TGTCCGCGGA cGTAGGGcTC ATCACAATTG
1951  TAAaCAAAGC CCTyGACGAC GGCAcTCCAA aCAGCTCtTC cGGTGTGAGA
2001  CGACGAAACG AGGGAGcTAG AGCGGGTAGT GGCGCGGGgA ACAGCCAGTG
2051  TAGCGCCTGT AGTCACCGAG GGATGGGGCG GTCGGgCGCC GCGAGGCTGC
2101  GGTGCcAGgT GGAGgTTcAA CATTCTTCAA ACGCCCGTGC CAAGTACATG
2151  GCGGACTGGA GGTCGGGCGG TGCGCGGAGC TGAACCTGCT TACGGAGGTG
2201  GTCCGGCAGC CCACCCACGT ACAACTCCGC CTTTTGGCGA GCGGAGAGGT
2251  TGTGGGCATG GCACAGGACG GCGTTGTAAC GCTCCGAGTA ATCCTGAACG
2301  GAAGAACCAA AAGGAAGGCG GGCAAGcTCC GCCAACCGAG TGCCCAAAAC
2351  AGGAGGCCCG AAGCGAAGCG AGCATAATTC GCGGAAGCGC TCCCAAGGAG
2401  GCATACCCTc GTcTTGCTcC AGGGCGTAGT ACCATGTcTG GCAACACCC
2451  CGAAGATGgT AGgACGCGAG CCATGTGCGA GCGGAGGCGA GCGTnTGCTG
2501  GCCGCGGAAG AACTGCTCGC ACTGGTTCAA CCAATTCAGG GGATCGGTCG
2551  AACCGTCGTA CGTAGGGAAC TCCAGTTTGT AGAATTTGGG CCCCGCCTGG
2601  GCGCCTGCGA GGGCAGCAGC AAGGGCTGGG TCGAGCCCCC CCTGCGGCTG
```

```
2651  GCCGCCCGAG GGAGAGGGCG CCCGAAGAAC AGCGGCCCGT CCACCCCCCC
2701  GAAAAGAGTG CTGGCGGGGG GTAGGGAGGA CATCGTTGTC GCCGCCGCCG
2751  TCGTGTAGGC TGTCGGGGAG GGCGACGTGG CCATCGAGTA GATCCGGGGA
2801  ATTC
```

```
   1 gaattcatta tgtggtctag gtaggttcta tatataagaa aacttgaaat gttctaaaaa
  61 aaaattcaag cccatgcatg attgaagcaa acggtatagc aacggtgtta acctgatcta
 121 gtgatctctt gcaatcctta acggccacct accgcaggta gcaaacggcg tccccctcct
 181 cgatatctcc gcggcgacct ctggcttttt ccgcggaatt gcgcggtggg gacggattcc
 241 acaaccgcga cgcaaccgcc tctcgccgct gggcccaca ccgctcggtg ccgtagcctc
 301 acgggactct ttctccctcc tccccgtta taaattggct tcatcccctc cttgcctcat
 361 ccatccaaat cccagtcccc aatccatcc cttcgtcgga gaaattcatc gaagcgaagc
 421 gaatcctcgc gatcctctca aggtactgcg agttttcgat cccctctcg acccctcgta
 481 tgtttgtgtt tgtcgtacgt ttgattaggt atgctttccc tgtttgtgtt cgtcgtagcg
 541 tttgattagg tatgctttcc ctgttcgtgt tcatcgtagt gtttgattag gtcgtgtgag
 601 gcgatggcct gctcgcgtcc ttcgatctgt agtcgatttg cgggtcgtgg tgtagatctg
 661 cgggctgtga tgaagttatt tggtgtgatc tgctcgcctg attctgcggg ttggctcgag
 721 tagatatgga tggttggacc ggttggttcg tttaccgcgc tagggttggg ctgggatgat
 781 gttgcatgcg ccgttgcgcg tgatcccgca gcaggacttg cgtttgattg ccagatctcg
 841 ttacgattat gtgatttggt tggacttat tagatctgta gcttctgctt atgttgccag
 901 atgcgcctac tgctccatat gcctgatgat aatccataaa tggcagtgga aatcaactag
 961 ttgattgcgg agtcatgtat cagctacagg tgtagggact agctacaggt gtagggactg
1021 cgtctaattg tttggtcctt aactcatgtg caattatgca atttagttta gatgtttgtt
1081 ccaatcatct aggctgtaaa agggacactg gttagattgc tgtttaatct ttttagtaga
1141 ttatattata ttggtaactt attaaccta ttacatgcca taacgtggat tctgctcatg
1201 cctgatgata atcatagatc actgtggaat taattagttg attgttgaat catgtttcat
1261 gtacatacca cggcacaatt gcttagttcc ttaacaaatg caaatttac tgatccatgt
1321 atgatttgcg tggttctcta atgtgaaata ctatagctac ttgttagtaa gaatcaggtt
1381 cgtatgctta atgctgtatg tgccttctgc tcatgcctga tgataatcat atatcactgg
1441 aattaattag ttgatcgttt aatcatatat caagtacata ccatgcaca attttagtc
1501 acttaaccca tgcagattga actgtccct gcatgttttg ctaaattgtt ctattctgat
1561 tagaccatat atcaggtatt tttttttggt aatgttctc ttattttaaa tgctatatag
1621 ttctggtact tgttagaaag atctggttca tagtttagtt gcctatcctt cgaattagga
1681 tgctgagcag ctgatcctat agctttgttt catgtatcaa ttcttttgtg ttcaacagtc
1741 agttttgtt agattcattg taacttatgt tcgcttactc ttctggtcct caatgcttgc
1801 agatgcagat cttcgttaag accctcactg gcaagaccat cacccttgag gttgagtctt
1861 cagacamtat tgacmatgtc maggctaaga tacaggacaa ggaaggcatt cctccggatc
1921 agcagaggct gatctttgct ggcaagcagc tcgaggatgg ccgtaccta gytgactaca
1981 acatccagaa ggagtccacc stccacctgg tgctcaggct caggggaggc atgcaaatct
2041 tcgtcaagac cctcactggc aagactatca gcttgaggt cgagtcttct gacacgatcg
2101 acaacgtgaa ggccaagatc caggacaagg agggaatccc cccggaccag cagcgtctca
2161 tcttcgctgg caagcagctc gaggatggcc gcaccctcgc tgactacaac atccagangg
2221 agtcgantnt ccaccttgtg ctcaggttna ggggtggcat gcagattttt gtcaagacct
2281 tnactggcaa gaccatcacc ttggaggtgg agtcttcgga caccatngac aatgtgaagg
2341 ngaagatcca ggacaaggaa ggaatccccc cagaccagca gcgtctattt tttgctggca
2401 agcagcttga ggatggccgc accctagcag actacaacat ccagaaggag tccacccttc
2461 acctggtgct ccgcttncgc ggtggtatgc agatcttcgt caagaccctc accggcaaga
2521 ccatcaccct ggaggtggag tcctctgaca ccatcgacaa tgtgaaggcg aagatccagg
2581 acaaggaggg catccccccg gaccagcagc gtctcatctt cgccggcaag cagctggagg
2641 atggccgcac cctggcagac tacaacatcc agaaggagtc cactctccac ctggtgctcc
2701 gtctccgtgg tggccagtaa tcctgggcca tgaagctgtc cttccaggtt cacaagtctg
2761 gtgccttctt ctgtccctcc gatgagatt atctgcatgt cgtggtcgtg tcctgatcga
2821 atcctcgttg aatccctatg tttttcttca agaaatgtga gtcctatgtc agtctggttg
2881 cgtttgtgaa catttctgct gctgagcagc actttggctg gaactgtgca atgaaataaa
2941 tggaaccctg gtttctggtt atgtgtgtgt tagctaatgt ttttgaagtg gaagctctaa
3001 tcttctatcg cgttgctact acaattctgc ttgtgttttg atgttcttgg tttctgttag
3061 ttggttcaga ggaagttttg cttccacaga ctaagatgca gttgaacttt ggttgccctg
3121 gtttctagat ttcatttgtg ctggttgagt gatagtaaga aacaaccggt gttcacatat
3181 aatcaggttt tgtgctgctc gagtgatcgt caaaaccac cggtgttcac atctaaaaag
3241 gtttcgatcc ccaggtttag atctcccgtt taattccaaa aaaaagttc tgtgtacttg
3301 catttagttg ggtggttgat gctggaaaga gtaactttca agagtaataa tctttggtga
3361 ctactctgtt tcaactgatc aatccctagg aaaggtacac ctttacttag ggaagaaatt
3421 cttagaacct tgcacttttgt ttcaactagt aatagtatac tttattagat aaaaaatatt
3481 cagatatatt agacaccgga tgtcatccac tcatccttac aaacctctgt catggtcctg
3541 cagaaatgtt tgccagctcc agtggcttcc tgataaatct gtggagtgcc tgttaatcgg
3601 ctgccaattt ttgctgagca ctgtatatat gttagtaagt actattgggc caccaattcg
```

FIGURE 5A (continued)

```
3661 attttgacac agcactattg gtccaccaat tcgattctga cacagcactg cataatttga
3721 aacgtgttgc tccatttttgc aaggctacaa atttagatca tgtttagcat tctgtgggat
3781 acaatatatg gatatcgaac aaacttggta tgtcagagaa aaaatagttt attttcaaaa
3841 ctaacatttt taaagccttc tatgaactt aaaccttcag catttgggat caagatgagt
3901 gctcgaacaa gagtgcactt tttctccaaa ataatctact acagagttct tttttatata
3961 taaaaaaact tatacttaac agataaatca gacttttctt gctccatatc accttgacaa
4021 atcaaagaag cagcaccagc gaagggtatt attattgagg taaatataag atctcgttta
4081 ctgaaaaaga ccgcgtgttt acctaaacta ccatttttgct ttgatagcag catacatgtg
4141 atagaattgc ggatcctacc gtgctgactg tgaaggtggt aggggtgaga gattggtggg
4201 cgaggtctga acgagcgaga acagtactgc atttactgtt cacaaggagg cggcttaggt
4261 tttgggtctc ccagctctct aagggaagct gagaattatg attctcttgc ttaattattt
4321 cttaaccaaa gttataaata tatagcctat gagatcctaa tttatggaaa taactaaact
4381 attttaagga aatatataaa tagataatca gcccactaac gggcctagcg cccactaaca
4441 ggcctggtgc tgagcccgac ataacatctc tccccgcctg gagaaacagc tcgtcctcga
4501 gctgaaatct ggtagaagca tcatcaacca acaccggggt catgctggaa cactgcatca
4561 ggcgctaccg cagctggtac gtcgtcgtcg aggaagtcag ccgactccaa gtagaacagt
4621 cgcttacact gatgtccgcg gacgtagggc tcatcacaat tgtaacaaag cccttgacga
4681 cggcactcca acagctcctc cggtgtgaga cgacgaaacg agggagctag agcgggtagt
4741 ggcgcgggaa cagccagtgt agcgcctgta gtcaccgagg gatggggcgg tcgggcgccg
4801 cgaggctgcg gtgcaggtgg aggtttcaca ttcctcaaac gcccgtgcca agtacatggc
4861 ggactggagg tcgggcggtg cgcggagctg aacctgctta cggaggtggt ccggcagccc
4921 acccacgtac aactccgcct tttggcgagc ggagaggttg tgggcatggc acaggacggc
4981 gttgtaacgc tccgagtaat cctgaacgga agaaccaaaa ggaaggcggg caagctccgc
5041 caaccgagtg cccaaaacag gaggcccgaa gcgaagcgag cataattcgc ggaagcgctc
5101 ccaaggaggc atacCctcgt cttgctccag ggcgtagtac catgtctggg caacaccccg
5161 aagatggtag gacgcgagcc atgtgcgagc ggaggcgagc gtctgctggc cgcggaagaa
5221 ctgctcgcac tggttcaacc aattcagggg atcggtcgaa ccgtcgtacg tagggaactc
5281 cagtttgtag aatttgggcc ccgcctgggc gcctgcgagg gcagcagcaa gggctgggtc
5341 gagccccccc tgcggctggc cgcccgaggg agagggcgcc cgaagaacag cggcccgtcc
5401 acccccccga aaagagtgct ggcggggggt agggaagaca tcgttgtcgc cgccgccgtc
5461 gtgtaggctg tcggggaagg cgacgtggcc atcgagtaga tccggggaat tc
```

FIGURE 5B

MQIFVKTLTGKTITLEVESSDXIDXVXAKIQDKEGIPPDQQRLIFAGKQLED
GRTLXDYNIQKESTXHLVLRLRGGMQIFVKTLTGKTITLEVESSDTIDNV
KAKIQDKEGIPPDQQRLIFAGKQLEDGRTLADYNIQXESXXHLVLRXRGGMQIFVKTX
TGKTITLEVESSDTXDNVKXKIQDKEGIPPDQQRLIFAGKQLEDGRTLADYNIQKEST
LHLVLRXRGGMQIFVKTLTGKTITLEVESSDTIDNVKAKIQDKEGIPPDQQRLIFAGK
QLEDGRTLADYNIQKESTLHLVLRLRGGQ

FIGURE 6
ubi4
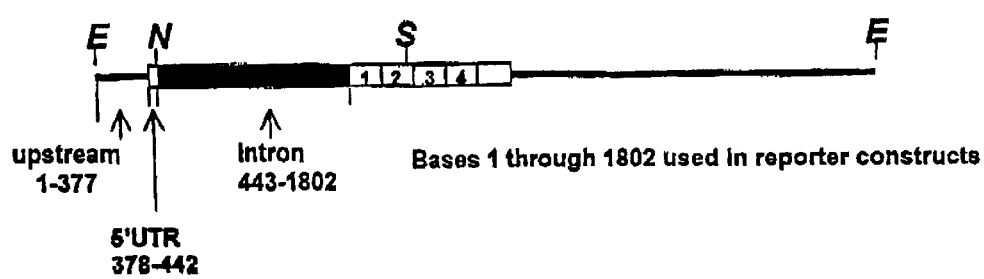
ubi9
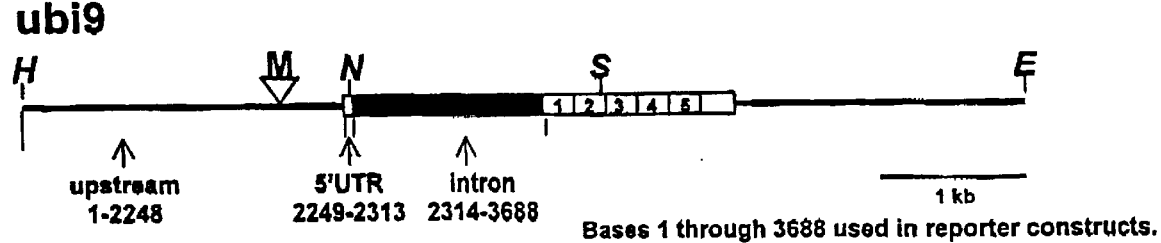

FIGURE 7A

```
   1  AAGTTTTGnT AAAATGAACA AAGAATTGGG GAAACTATAG CCAAAGTGGG
  51  TGGGGAATGG TGCCAAACAA AACTTCGTAA ACCAACCCAA AAAGATCCGG
 101  AAAACAAATG GATACGTGCA GGGCATGCAT GCAATAGCCC AGCCATAAAA
 151  AGCGGCGAGC CAATGCCCGG GTGTCAAACA AAATGGCGCC TGTGCCGGCT
 201  CTGGCTGCTT CCGGCTCAGC TTTCGGAACG ATCCGCCGCA GTTTGGCCTC
 251  GCATATGATG ACGATGATGG TCTCCTCTTC TCGATTTGTA GCTCCGGCAT
 301  GGGAGCCACC TCCTGTCGGC TCACACATAG CACGCGCCTT AGCCCGTGCT
 351  CGCTCTCCCC TAGATGCTTC ACCTGCGCCA ATCAGTGTGA GCCCATCGTG
 401  TCAGATGGTA CTCGTACGTA TGGAGTAACG TGATACCACA ACACGTACAC
 451  TGGTCAGAAT TGATAGTATA TGATCCTGTC GACCCGATGT GTTTTAGTAC
 501  CTTGCAGTGG CCGGAGAGGA GTGGCCGCGC GCATGCGGCG CAGGGGTTCT
 551  CCGCGCTCGC TGATCGCTTC CTCACTGTGC GCTCGTTTAG GAACACCACC
 601  TCGTGGTCGC TCACCATGTG TGACTGCATG CAACGCTACG AATCAGGACC
 651  CAGATGGAAA CGAAGCGCCT CTCGACCACC TCTGCCTCGG TGATGGTTGG
 701  TGTGCAGTGC GTACGCATGC ACGCTACCAA TATCATACCT GGATGCCGGT
 751  GCAATCGAAC AGCTTCAGGT TGTCGACGCG GACGGCGAAG CAGGACGCGT
 801  ACTTCCATAT CTTTGGGTTC CATTACGTAC CGTCAATCGA ATAAATAAAG
 851  AGAAGAGTTT GAGATCAGCT TGTTGGGAGC AGGTGACCGC CCGACATGCA
 901  TGCCGATTGT CGACGGCACG GAAATAAACA ACACATTTGT GAGGGAGCCA
 951  GGGAGGCAGT GGCGGCACAG CGTCGCGGCA CAGTCGATGC AGAAGTGGTT
1001  CTTGTCGTTC TTGCGCTCCC CCCGGGTGTG CAGCGCACGC CTTTGAAAAA
1051  CTCCGATAGC AGGCCACACA GCCATTGCGG GGCGCCGCGC ACGGCCGCCA
1101  GCTGCATCCC CGTTTGTTCG CACATGCGCT AGGTGGTCCT GCGGCCGTTC
1151  CTTGCACCGC GGAGACGCGG GGTGGACCAG TGGGGAATG GATGAACTGC
1201  TGGTAGGTTT GGTTGGATTG GCGAGTGCGT AGAGGGGGCA TGGGCAACGA
```

FIGURE 7A (continued)

```
1251  TAGACTCGAT TCAATTCAAA GACTGAAAAT AGTGGAGTTC TAACACCATT

1301  CTGTGCGGCG CTAATTCTCG ACATGGCAGG CGTAAGCATA ATACCGACAT

1351  GGCATGCAAC GATGTTCGTG AACAGTGGTG ACACATGGAT ATGGTGGCCG

1401  TCCAGGGGAT TCGTTCCATT CAATTCAAAG ACCGAAAATC GCGGGGTTCC

1451  GTAGCATTTT GTGCGGTGCT AATTCTCGAA CATGCGAGAC GTAAGCCTAA

1501  TACCGAGATG GCATGCAACA ATGTTCGTGA ACAACAGTGA CACGTGGATG

1551  CGGTGGCCGT CTAGGGATTC GCGTTCTAAG CTGGTATATG TGCGGTGTTA

1601  ATTCTTGACA TGCGGGGCGT AAGTGTAATA CCAAGATGAA CGGTGACACG

1651  TGGACGCGGG GGTCGTCAAA CAATTCATTC CGTGGTCTAG GGTAGGTTAT

1701  ATATAAAGGC CAGTCTTAGT GGGGGATTTT ATGGCCATGT TATTAATGCA

1751  ACCCATATTT GGAAAACAGT GCAGGAAGAG TTTCATCTTC GTAAAACTCT

1801  CTCTAATTCC ATGAAACTCT TATCATCTCT CTCTTCATCA ATACGGTGCC

1851  ACATCAGCCT ATTTAATGTC CATGAAACTC TGATGAAATC CACTGAGACG

1901  GGCCTCAGAA AACTTGAAAT CTTCTAAAAA AAATTCAAGT CCATGCATGA

1951  TTGAAGCAAA CGGTATAGCA ACGGTGTTAA CCTGATCTAG TGATCTCTTG

2001  TAATCCTTAA CGGCCACCTA CCACAGGTAG CAAACGGCGT CCCCCTCCTC

2051  GATATCTCCG CGGCGGCCTC TGGCTTTTTC CGCGGAATTG CGCGGTGGGG

2101  ACGGATTCCT CGAGACCGCG ACACAACCGC CTTTCGCCGC TGGGCCCCAC

2151  ACCGCTCGGT GCCGTAGCCT CACGGGACTC TTTCTCCCTC CTCCCCCGCT

2201  ATAAATTGGC TTCATCCCCT CCTTGCCTCA TCCATCCAAA TCCCAGTCCC

2251  CAATCCCAGC CCATCGTCGG AGAAATTCAT AGAAGCGAAG CGAATCCTCG

2301  CGATCCTCTC AAGGTAGTGC GAGTTTTCGA TTCCCCTCTC GACCCCTCGT

2351  ATGCTTTCCC TGTTTGTGTT TCGTCGTAGC GTTTGATTAG GTATGCTTTC

2401  CCTGTTTGTG TTCGTCGTAG CGTTTGATTT GGTATGCTTT CCCCGTTCGT

2451  GTTCCTCGTA GTGTTTGATT AGGTCGTGTG AGGCGAtGGC CTGCTCGCAT

2501  CCTTCGATCT GTAGTCGATT TGCGGGTCGT GGTGTAGATC TGCGGGCTGT

2551  GATGAAGTTA TTTGGTGTGA TCGTGCTCGC CTGATTCTGC GGGTTGGCTC
```

FIGURE 7A (continued)

```
2601  GAGTAGATAT GATGGTTGGA CCGGTTGGTT TGTTTACCGC GCTAGGGTTG
2651  GGCTGGGATG ATGTTGCATG CGCCGTTGCG CGTGATCCCG CAGCAGGACT
2701  TGCGTTTGAT TGCCAGATCT CGTTACGATT ATGTGATTTG GTTTGGACTT
2751  TTTAGATCTG TAGCTTCTGC TTATGTGCCA GATGCGCCTA CTGCTCATAT
2801  GCCTGATGAT AATCATAAAT GGCTGTGGAA CTAACTAGTT GATTGCGGAG
2851  TCATGTATCA GCTACAGGTG TAGGGACTAG CTACAGGTGT AGGGACTTGC
2901  GTCTAAATTG TTTGGTCCTG TACTCATGTT GCAATTATGC AATTTAGTTT
2951  AGATTGTTTG TTCCACTCAT CTAGGCTGTA AAAGGGACAC TGCTTAGATT
3001  GCTGTTTAAT CTTTTTAGTA GATTATATAT TATATTGGTA ACTTATTACC
3051  CTTATTACAT GCCATACGTG ACTTCTGCTC ATGCCTGATG ATAATCATAG
3101  ATCACTGTGG AATTAATTAG TTGATTGTTG AATCATGTTT CATGTACATA
3151  CCACGGCACA ATTGCTTAGT TCCTTAACAA ATGCAAATTT TACTGATCCA
3201  TGTATGATTT GCGTGGTTCT CTAATGTGAA ATACTATAGC TACTTGTTAG
3251  TAAGAATCAG GTTCGTATGC TTAATGCTGT ATGTGCCTTC TGCTCATGCC
3301  TGATGATAAT CATATATCAC TGGAATTAAT TAGTTGATCG TTAATCATA
3351  TATCAAGTAC ATACCATGGC ACAATTTTTA GTCACTTAAC CCATGCAGAT
3401  TGAACTGGTC CCTGCATGTT TTGCTAAATT GTTCTATTTC TGATTAGACC
3451  ATATATCATG TAATTTTTTT TTTGGGTAAT GGTTCTCCTA TTTTAAATGC
3501  TATATAGTTC TGGTACTTGT TAGAAAAATC TGCTTCCATA GTTTAGTTGC
3551  TTATCCCTCG AATTATGATG CTGAGCAGCT GATCCTATAG CTTtGTTTCA
3601  GGTATCAATT CTnGTGTTCA ACAGTCAGTT TTtGTTAGAT TCATtGtAAc
3651  TTAtGGTCGC TTAcTcTTcT GGTCCTCAAT GCTTGCAGAT G
```

FIGURE 7B

```
  1  TAAGTCCTGG GCCATGAGCA GCTGTCCTTC CAGGGTTCAC AAGTAGTGGT
 51  GCCTTCTTnC TGTCCCTCCG ATGGAGATTA TCTGCATGTC GTGGTCGTGT
101  CCTGATCGAG TCGTCGTTGA GTCCCTATGT TTTTTCTTCA AGAAATGTGA
151  GTCCTATGTC AGTCTGGTTG CGTTTGTGAA CATTTCTGC TGCTGCGCAG
201  CAGTTTGGTT GGAACTGTGC AATGAAATAA ATTGAACCCT GGTTTCTGGT
251  TATGTGTGTT AGCTAATGTT TTTGAAGTGG AAGCTnTAAT CTTnTATCGC
301  GTTGCTACTA CAATTCTGnT TGTGTTTTGA TGTTCTTGTT TCT
```

FIGURE 8A

```
   1 aagttttgnt aaaatgaaca aagaattggg gaaactatag ccaaagtggg tggggaatgg
  61 tgccaaacaa aacttcgtaa accaacccaa aaagatccgg aaaacaaatg gatacgtgca
 121 gggcatgcat gcaatagccc agccataaaa agcggcgagc caatgcccgg gtgtcaaaca
 181 aaatggcgcc tgtgccggct ctggctgctt ccggctcagc tttcggaacg atccgccgca
 241 gtttggcctc gcatatgatg acgatgatgg tctcctcttc tcgatttgta gctccggcat
 301 gggagccacc tcctgtcggc tcacacatag cacgcgcctt agcccgtgct cgctctcccc
 361 tagatgcttc acctgcgcca atcagtgtga gcccatcgtg tcagatggta ctcgtacgta
 421 tggagtaacg tgataccaca acacgtacac tggtcagaat tgatagtata tgatcctgtc
 481 gacccgatgt gttttagtac cttgcagtgg ccggagagga gtggccgcgc gcatgcggcg
 541 caggggttct ccgcgctcgc tgatcgcttc ctcactgtgc gctcgtttag gaacaccacc
 601 tcgtggtcgc tcaccatgtg tgactgcatg aacgctacg aatcaggacc cagatggaaa
 661 cgaagcgcct ctcgaccacc tctgcctcgg tgatggttgg tgtgcagtgc gtacgcatgc
 721 acgctaccaa tatcatacct ggatgccggt gcaatcgaac agcttcaggt tgtcgacgcg
 781 gacggcgaag caggacgcgt acttccatat ctttgggttc cattacgtac cgtcaatcga
 841 ataaataaag agaagagttt gagatcagct tgttgggagc aggtgaccgc ccgacatgca
 901 tgccgattgt cgacggcacg gaaataaaca acacatttgt gagggagcca gggaggcagt
 961 ggcggcacag cgtcgcggca cagtcgatgc agaagtggtt cttgtcgttc ttgcgctccc
1021 cccgggtgtg cagcgcacgc ctttgaaaaa ctccgatagc aggccacaca gccattgcgg
1081 ggcgccgcgc acggccgcca gctgcatccc cgtttgttcg cacatgcgct aggtggtcct
1141 gcggccgttc cttgcaccgc ggagacgcgg ggtggaccag tgggggaatg gatgaactgc
1201 tggtaggttt ggttggattg gcgagtgcgt agagggggca tggcaacga tagactcgat
1261 tcaattcaaa gactgaaaat agtggagttc taacaccatt ctgtgcggcg ctaattctcg
1321 acatggcagg cgtaagcata ataccgacat ggcatgcaac gatgttcgtg aacagtggtg
1381 acacatggat atggtggccg tccaggggat tcgttccatt caattcaaag accgaaaatc
1441 gcggggttcc gtagcatttt gtgcggtgct aattctcgaa catgcgagac gtaagcctaa
1501 taccgagatg gcatgcaaca atgttcgtga acaacagtga cacgtcggatg cggtggccgt
1561 ctagggattc gcgttctaag ctggtatatg tgcggtgtta attcttgaca tgcgggcgt
1621 aagtgtaata ccaagatgaa cggtgacacg tggacgcggg ggtcgtcaaa caattcattc
1681 cgtggtctag ggtaggttat atataaaggc cagtcttagt gggggatttt atggccatgt
1741 tattaatgca acccatattt ggaaaacagt gcaggaagag tttcatcttc gtaaaactct
1801 ctctaattcc atgaaactct tatcatctct ctcttcatca atacggtgcc acatcagcct
1861 atttaatgtc catgaaactc tgatgaaatc cactgagacg ggcctcagaa aacttgaaat
1921 cttctaaaaa aaattcaagt ccatgcatga ttgaagcaaa cggtatagca acggtgttaa
1981 cctgatctag tgatctcttg taatccttaa cggccaccta ccacaggtag caaacggcgt
2041 cccctcctc gatatctccg cggcggcctc tggcttttc cgcggaattg cgcggtgggg
2101 acggattcct cgagaccgcg acacaaccgc ctttcgccgc tgggccccac accgctcggt
2161 gccgtagcct cacgggactc tttctccctc ctcccccgct ataaattggc ttcatccct
2221 ccttgcctca tccatccaaa tcccagtccc caatcccagc ccatcgtcgg agaaattcat
2281 agaagcgaag cgaatcctcg cgatcctctc aaggtagtgc gagttttcga ttcccctctc
2341 gaccctcgt atgctttccc tgtttgtgtt tcgtcgtagc gtttgattag gtatgctttc
2401 cctgtttgtg ttcgtcgtag cgtttgattt ggtatgcttt ccccgttcgt gttcctcgta
2461 gtgtttgatt aggtcgtgtg aggcgatggc ctgctcgcat ccttcgatct gtagtcgatt
2521 tgcgggtcgt ggtgtagatc tgcgggctgt gatgaagtta tttggtgtga tcgtgctcgc
2581 ctgattctgc gggttggctc gagtagatat gatggttgga ccggttggtt tgtttaccgc
2641 gctagggttg ggctgggatg atgttgcatg cgccgttgcg cgtgatcccg cagcaggact
2701 tgcgtttgat tgccagatct cgttacgatt atgtgatttg gtttggactt tttagatctg
2761 tagcttctgc ttatgtgcca gatgcgccta ctgctcatat gcctgatgat aatcataat
2821 ggctgtggaa ctaactagtt gattgcggag tcatgtatca gctacaggtg tagggactag
2881 ctacaggtgt agggacttgc gtctaaattg tttgtcctg tactcatgtt gcaattatgc
2941 aatttagttt agattgtttg ttccactcat ctaggctgta aaagggacac tgcttagatt
3001 gctgtttaat cttttagta gattatatat tatattggta acttattacc cttattacat
3061 gccatacgtg acttctgctc atgcctgatg ataatcatag atcactgtgg aattaattag
3121 tgattgttg aatcatgttt catgtacata ccacggcaca attgcttagt tccttaacaa
3181 atgcaaattt tactgatcca tgtatgattt gcgtggttct ctaatgtgaa atactatagc
3241 tacttgttag taagaatcag gttcgtatgc ttaatgctgt atgtgccttc tgctcatgcc
3301 tgatgataat catatatcac tggaattaat tagttgatcg tttaatcata tatcaagtac
3361 ataccatggc acaattttta gtcacttaac ccatgcagat tgaactggtc cctgcatgtt
3421 ttgctaaatt gttctatttc tgattagacc atatatcatg taattttttt tttgggtaat
3481 ggttctccta ttttaaatgc tatatagttc tggtacttgt tagaaaaatc tgcttccata
3541 gtttagttgc ttatccctcg aattatgatg ctgagcagct gatcctatag ctttgtttca
3601 kgtatcaatt cttgtgttca acagtcagtt tttgttagat tcattgtaac ttatggtcgc
```

FIGURE 8A (continued)

```
3661 ttactcttct ggtcctcaat gcttgcagat gcagattttc gttaagaccc tcactggcaa
3721 gaccatcacc cttgaggttg agtcctcaga cactattgac aatgtcaagg ctaagatcca
3781 ggacaaggaa ggcattcctc cagatcagca gaggctgaty tttgctggca agcagctcga
3841 ggatggccgt accctagctg actacaacat ccagaaggag tccaccctcc acctggtgct
3901 caggcttagg ggaggcatgc agattttcgt caagaccctc actggcaaga ctatcacgct
3961 tgaggtcgag tcttctgaca cgatcgacaa cgtgaaggcc aagatccagg acaaggaggg
4021 aatccccccg gaccagcagc gtytcatttt cgctggcaag cagctcgagg atggccgcac
4081 cctcgctgac tacaacatcc agaaggagtc gactctccac cttgtgctca ggctcagggg
4141 tggcatgcag atcttcgtca agaccctcac tggcaagacc atcaccttgg aggtggagtc
4201 ctcggacacc attgacaatg tgaaggcgaa gatccaggac aaggagggca tccccccgga
4261 ccagcagcgt ctcatyttcg ccggcaagca rcttgaggat ggccgcaccc ttgcgganta
4321 caacatccag aargagtcca cccttcacct ggtgctccgc cttcgtggtg gtatgcagat
4381 tttcgtcaag accctcaccg gcaagaccat caccctggag gtggagtcct ctgacaccat
4441 tgacaatgtg aaggcgaaga tccaggataa ggagggcatc ccccggacc agcagcgtyt
4501 tatctttgct ggcaagcagc ttgaggatgg ccgcaccctg gcagantaca acatccagaa
4561 ggagtccacc cttcacctgg tgctccgcct tcgcggtggt atgcagatyt tcgtcaagac
4621 cctcaccggc aagaccatca ccctggaggt ggagtcctct gacaccatcg acaatgtgaa
4681 ggcgaagatc caggacaagg agggcatccc cccggaccag cagcgtctca tcttcgccgg
4741 caagcagctg gaggatggcc gcaccctggc agactacaac atccagaagg agtccactct
4801 ccacctggtg ctccgtctcc gtggtggcca gtaagtcctg ggccatgagc agctgtcctt
4861 ccagggttca caagtagtgg tgccttcttn ctgtccctcc gatggagatt atctgcatgt
4921 cgtggtcgtg tcctgatcga gtcgtcgttg agtccctatg ttttttcttc aagaaatgtg
4981 agtcctatgt cagtctggtt gcgtttgtga acattttctg ctgctgcgca gcagtttggt
5041 tggaactgtg caatgaaata aattgaaccc tggtttctgg ttatgtgtgt tagctaatgt
5101 ttttgaagtg gaagctntaa tcttntatcg cgttgctact acaattctgn ttgtgttttg
5161 atgttcttgt ttct
```

FIGURE 8B

MQIFVKTLTGKTITLEVESSDTIDNVKAKIQDKEGIPPDQQRLI

FAGKQLEDGRTLADYNIQKESTLHLVLRLRGGMQIFVKTLTGKTITLEVESSDTIDNV

KAKIQDKEGIPPDQQRXIFAGKQLEDGRTLADYNIQKESTLHLVLRLRGGMQIFVKTL

TGKTITLEVESSDTIDNVKAKIQDKEGIPPDQQRLIFAGKQLEDGRTLAXYNIQKEST

LHLVLRLRGGMQIFVKTLTGKTITLEVESSDTIDNVKAKIQDKEGIPPDQQRXIFAGK

QLEDGRTLAXYNIQKESTLHLVLRLRGGMQIFVKTLTGKTITLEVESSDTIDNVKAKI

QDKEGIPPDQQRLIFAGKQLEDGRTLADYNIQKESTLHLVLRLRGGQ

FIGURE 10

```
   1 gaattcatta tgtggtctag gtaggttcta tatataagaa aacttgaaat gttctaaaaa
  61 aaaattcaag cccatgcatg attgaagcaa acggtatagc aacggtgtta acctgatcta
 121 gtgatctctt gcaatcctta acggccacct accgcaggta gcaaacggcg tccccctcct
 181 cgatatctcc gcggcgacct ctggctttt ccgcggaatt gcgcggtggg gacggattcc
 241 acaaccgcga cgcaaccgcc tctcgccgct gggccccaca ccgctcggtg ccgtagcctc
 301 acgggactct ttctccctcc tcccccgtta taaattggct tcatccctc cttgcctcat
 361 ccatccaaat cccagtcccc aatcccatcc cttcgtcgga gaaattcatc gaagcgaagc
 421 gaatcctcgc gatcctctca aggtactgcg agttttcgat ccccctctcg accctcgta
 481 tgtttgtgtt tgtcgtacgt ttgattaggt atgctttccc tgtttgtgtt cgtcgtagcg
 541 tttgattagg tatgctttcc ctgttcgtgt tcatcgtagt gtttgattag gtcgtgtgag
 601 gcgatggcct gctcgcgtcc ttcgatctgt agtcgatttg cgggtcgtgg tgtagatctg
 661 cgggctgtga tgaagttatt tggtgtgatc tgctcgcctg attctgcggg ttggctcgag
 721 tagatatgga tggttggacc ggttggttcg tttaccgcgc tagggttggg ctgggatgat
 781 gttgcatgcg ccgttgcgcg tgatcccgca gcaggacttg cgtttgattg ccagatctcg
 841 ttacgattat gtgatttggt ttggacttat tagatctgta gcttctgctt atgttgccag
 901 atgcgcctac tgctccatat gcctgatgat aatccataaa tggcagtgga aatcaactag
 961 ttgattgcgg agtcatgtat cagctacagg tgtagggact agctacaggt gtagggactg
1021 cgtctaattg tttggtcctt aactcatgtg caattatgca atttagttta gatgtttgtt
1081 ccaatcatct aggctgtaaa agggacactg gttagattgc tgtttaatct ttttagtaga
1141 ttatattata ttggtaactt attaacccta ttacatgcca taacgtggat tctgctcatg
1201 cctgatgata atcatagatc actgtggaat taattagttg attgttgaat catgtttcat
1261 gtacatacca cggcacaatt gcttagttcc ttaacaaatg caaatttac tgatccatgt
1321 atgatttgcg tggttctcta atgtgaaata ctatagctac ttgttagtaa gaatcaggtt
1381 cgtatgctta atgctgtatg tgccttctgc tcatgcctga tgataatcat atatcactgg
1441 aattaattag ttgatcgttt aatcatatat caagtacata ccatggcaca ttttttagtc
1501 acttaaccca tgcagattga actggtccct gcatgttttg ctaaattgtt ctattctgat
1561 tagaccatat atcaggtatt ttttttttggt aatggttctc ttatttaaa tgctatatag
1621 ttctggtact tgttagaaag atctggttca tagtttagtt gcctatcctt cgaattagga
1681 tgctgagcag ctgatcctat agctttgttt catgtatcaa ttctttttgtg ttcaacagtc
1741 agttttttgtt agattcattg taacttatgt tcgcttactc ttctggtcct caatgcttgc
1801 ag
```

FIGURE 11

```
   1 aagttttgnt aaaatgaaca aagaattggg gaaactatag ccaaagtggg tggggaatgg
  61 tgccaaacaa aacttcgtaa accaacccaa aaagatccgg aaaacaaatg gatacgtgca
 121 gggcatgcat gcaatagccc agccataaaa agcggcgagc caatgcccgg gtgtcaaaca
 181 aaatggcgcc tgtgccggct ctggctgctt ccggctcagc tttcggaacg atccgccgca
 241 gtttggcctc gcatatgatg acgatgatgg tctcctcttc tcgatttgta gctccggcat
 301 gggagccacc tcctgtcggc tcacacatag cacgcgcctt agcccgtgct cgctctcccc
 361 tagatgcttc acctgcgcca atcagtgtga gcccatcgtg tcagatggta ctcgtacgta
 421 tggagtaacg tgataccaca acacgtacac tggtcagaat tgatagtata tgatcctgtc
 481 gacccgatgt gttttagtac cttgcagtgg ccggagagga gtggccgcgc gcatgcggcg
 541 caggggttct ccgcgctcgc tgatcgcttc ctcactgtgc gctcgtttag gaacaccacc
 601 tcgtggtcgc tcaccatgtg tgactgcatg caacgctacg aatcaggacc cagatggaaa
 661 cgaagcgcct ctcgaccacc tctgcctcgg tgatggttgg tgtgcagtgc gtacgcatgc
 721 acgctaccaa tatcatacct ggatgccggt gcaatcgaac agcttcaggt tgtcgacgcg
 781 gacggcgaag caggacgcgt acttccatat cttgggttc cattacgtac cgtcaatcga
 841 ataaataaag agaagagttt gagatcagct tgttgggagc aggtgaccgc cgacatgca
 901 tgccgattgt cgacggcacg gaaataaaca acacatttgt gagggagcca gggaggcagt
 961 ggcggcacag cgtcgcggca cagtcgatgc agaagtggtt cttgtcgttc ttgcgctccc
1021 cccgggtgtg cagcgcacgc ctttgaaaaa ctccgatagc aggccacaca gccattgcgg
1081 ggcgccgcgc acggccgcca gctgcatccc cgtttgttcg cacatgcgct aggtggtcct
1141 gcggccgttc cttgcaccgc ggagacgcgg ggtggaccag tgggggaatg gatgaactgc
1201 tggtaggttt ggttggattg gcgagtgcgt agaggggca tgggcaacga tagactcgat
1261 tcaattcaaa gactgaaaat agtggagttc taacaccatt ctgtgcggcg ctaattctcg
1321 acatggcagg cgtaagcata ataccgacat ggcatgcaac gatgttcgtg aacagtggtg
1381 acacatggat atggtggccg tccaggggat tcgttccatt caattcaaag accgaaaatc
1441 gcggggttcc gtagcatttt gtgcggtgct aattctcgaa catgcgagac gtaagcctaa
1501 taccgagatg gcatgcaaca atgttcgtga acaacagtga cacgtggatg cggtggccgt
1561 ctagggattc gcgttctaag ctggtatatg tgcggtgtta attcttgaca tgcggggcgt
1621 aagtgtaata ccaagatgaa cggtgacacg tggacgcggg ggtcgtcaaa caattcattc
1681 cgtggtctag ggtaggttat atataaaggc cagtcttagt gggggatttt atggccatgt
1741 tattaatgca acccatattt ggaaaacagt gcaggaagag tttcatcttc gtaaaactct
1801 ctctaattcc atgaaactct tatcatctct ctcttcatca atacggtgcc acatcagcct
1861 atttaatgtc catgaaactc tgatgaaatc cactgagacg ggcctcagaa aacttgaaat
1921 cttctaaaaa aaattcaagt ccatgcatga ttgaagcaaa cggtatagca acggtgttaa
1981 cctgatctag tgatctcttg taatccttaa cggccaccta ccacaggtag caaacggcgt
2041 ccccctcctc gatatctccg cggcggcctc tggcttttc cgcggaattg cgcggtgggg
2101 acggattcct cgagaccgcg acacaaccgc ctttcgccgc tgggccccac accgctcggt
2161 gccgtagcct cacgggactc tttctccctc ctccccgct ataaattggc ttcatcccct
2221 ccttgcctca tccatccaaa tcccagtccc caatcccagc ccatcgtcgg agaaattcat
2281 agaagcgaag cgaatcctcg cgatcctctc aaggtagtgc gagttttcga ttcccctctc
2341 gaccctcgt atgctttccc tgtttgtgtt tcgtcgtagc gtttgattag gtatgctttc
2401 cctgtttgtg ttcgtcgtag cgtttgattt ggtatgcttt ccccgttcgt gttcctcgta
2461 gtgtttgatt aggtcgtgtg aggcgatggc ctgctcgcat ccttcgatct gtagtcgatt
2521 tgcgggtcgt ggtgtagatc tgcgggctgt gatgaagtta tttggtgtga tcgtgctcgc
2581 ctgattctgc gggttggctc gagtagatat gatggttgga ccggttggtt tgtttaccgc
2641 gctagggttg ggctgggatg atgttgcatg cgccgttgcg cgtgatcccg cagcaggact
2701 tgcgtttgat tgccagatct cgttacgatt atgtgatttg gtttggactt tttagatctg
2761 tagcttctgc ttatgtgcca gatgcgccta ctgctcatat gcctgatgat aatcataaat
2821 ggctgtggaa ctaactagtt gattgcggag tcatgtatca gctacaggtg tagggactag
2881 ctacaggtgt agggacttgc gtctaaattg tttggtcctg tactcatgtt gcaattatgc
2941 aatttagttt agattgtttg ttccactcat ctaggctgta aaagggacac tgcttagatt
3001 gctgtttaat ctttttagta gattatatat tatattggta acttattacc cttattacat
3061 gccatacgtg acttctgctc atgcctgatg ataatcatag atcactgtgg aattaattag
3121 ttgattgttg aatcatgttt catgtacata ccacggcaca attgcttagt tccttaacaa
3181 atgcaaattt tactgatcca tgtatgattt gcgtggttct ctaatgtgaa atactatagc
```

FIGURE 11 (continued)

```
3241 tacttgttag taagaatcag gttcgtatgc ttaatgctgt atgtgccttc tgctcatgcc
3301 tgatgataat catatatcac tggaattaat tagttgatcg tttaatcata tatcaagtac
3361 ataccatggc acaattttta gtcacttaac ccatgcagat tgaactggtc cctgcatgtt
3421 ttgctaaatt gttctatttc tgattagacc atatatcatg taattttttt tttgggtaat
3481 ggttctccta ttttaaatgc tatatagttc tggtacttgt tagaaaaatc tgcttccata
3541 gtttagttgc ttatccctcg aattatgatg ctgagcagct gatcctatag ctttgtttca
3601 kgtatcaatt cttgtgttca acagtcagtt tttgttagat tcattgtaac ttatggtcgc
3661 ttactcttct ggtcctcaat gcttgcag
```

FIGURE 14

```
   1 agatctacaa ttatcngcaa cgtgttacac attttgtgct acaatatacc ttcaccattt
  61 tgtgtatata taaaggttgc atctcttcaa acaaaaatca ctccatcaca acacaatgtc
 121 ttcttcttct tctattacta ctactcttcc tttatgcacc aacaaatccc tctcttcttc
 181 cttcaccacc accaactcat ccttgttatc aaaaccctct caacttttcc tccacggaag
 241 gcgtaatcaa agtttcaagg tttcatgcaa cgcaaacaac gttgacaaaa accctgacgc
 301 tgttgataga cgaaacgttc ttttagggtt aggaggtctt tatggtgcag ctaatcttgc
 361 accattagcg actgctgcac ctataccacc tcctgatctc aagtcttgtg gtactgccca
 421 tgtaaaagaa ggtgttgatg taatatacag ttgttgccct cctgtacccg atgatatcga
 481 tagtgttccg tactacaagt tcccttctat gactaaactc cgcatccgcc ccctgctca
 541 tgcggcggat gaggagtacg tagccaagta tcaattggct acgagtcgaa tgagggaact
 601 tgataaagac ccctttgacc ctcttggctt taaacaacaa gctaatattc attgtgctta
 661 ttgcaacggt gcttacaaag ttggtggcaa agaattgcaa gttcatttct cgtggctttt
 721 ctttcccttt catagatggt acttgtactt ttacgaaaga attttgggat cacttattaa
 781 tgatccaact tttgctttac cttactggaa ttgggatcat ccaaaaggca tgcgtatacc
 841 tcccatgttt gatcgtgagg gatcatctct ttacgatgag aaacgtaacc aaaatcatcg
 901 caatggaact attattgatc ttggtcattt tggtaaggaa gttgacacac ctcagctaca
 961 gataatgact aataatttaa ccctaatgta ccgtcaaatg gttactaatg ctccttgccc
1021 ttcccaattc ttcggtgctg cttacctctg ggttctgaac ccaagtccgg gtcagggtac
1081 tattgaaaac atccctcata ctccggttca catctggacc ggtgacaaac ctcgtcaaaa
1141 aaacggtgaa gacatgggta atttctactc agccggttta gatccgattt tttactgcca
1201 ccatgccaat gtggacagga tgtggaatga atggaaatta attggcggga aagaaggga
1261 tttaacagat aaagattggt tgaactctga attcttttc tacgatgaaa atcgtaaccc
1321 ttaccgtgtg aaagtccgtg atgttttgga cagtaaaaaa atgggattcg attacgcgcc
1381 aatgcccact ccatggcgta attttaaacc aatcagaaag tcatcatcag gaaaagtgaa
1441 tacagcgtca attgcaccag ttagcaaggt gttcccattg gcgaagctgg accgtgcgat
1501 ttcgttctct atcacgcggc cagcctcgtc aaggacaaca caagagaaaa atgagcagga
1561 ggagattctg acattcaata aaatatcgta tgatgatagg aactatgtaa ggttcgatgt
1621 gtttctgaac gtggacaaga ctgtgaatgc agatgagctt gataaggcgg agtttgcagg
1681 gagttatact agcttgccgc atgttcatgg aagtaatact aatcatgtta ccagtgttac
1741 tttcaagctg gcgataactg aactgttgga ggatattgga ttggaagatg aagatactat
1801 cgcggtgact ttaattccaa aagctggcgg tgaaggtgta tccattgaaa gtgtggagat
1861 caagcttgag gattgttaaa gtctgcatga gttggtggct atggagccaa atttatgttt
1921 aattagtata attatgtgtg gtttgagtta tgttttatgt taaaatgtat cagctcgatc
1981 gatagctgat tgctagttgt gttaatgcta tgtatgaaat aaataaatgg ttgtcttcca
2041 ttcagtttat catttttgt cattctaatt aacggttaac ttttttttct actatttata
2101 cgaagctact atactatgta tatcatttgg aaaattatat attatt
```

FIGURE 15

```
   1 gaattccggc gtgggcgctg ggctagtgct cccgcagcga gcgatctgag agaacggtag
  61 agttccggcc gggcgcgcgg gagaggagga gggtcgggcg gggaggatcc gatggccggg
 121 aacgagtgga tcaatgggta cctggaggcg atcctcgaca gccacacctc gtcgcggggt
 181 gccggcggcg gcggcggcgg gggggacccc aggtcgccga cgaaggcggc gagcccccgc
 241 ggcgcgcaca tgaacttcaa ccccccgcac tacttcgtcg aggaggtggt caagggcgtc
 301 gacgagagcg acctccaccg gacgtggatc aaggtcgtcg ccacccgcaa cgcccgcgag
 361 cgcagcacca ggctcgagaa catgtgctgg cggatctggc acctcgcgcg caagaagaag
 421 cagctggagc tggagggcat ccagagaatc tcggcaagaa ggaaggaaca ggagcaggtg
 481 cgtcgtgagg cgacggagga cctggccgag gatctgtcag aaggcgagaa gggagacacc
 541 atcggcgagc ttgcgccggt tgagacgacc aagaagaagt tccagaggaa cttctctgac
 601 cttaccgtct ggtctgacga caataaggag aagaagcttt acattgtgct catcagcgtg
 661 catggtcttg ttcgtggaga aaacatggaa ctaggtcgtg attctgatac aggtggccag
 721 gtgaaatatg tggtcgaact tgcaagagcg atgtcaatga tgcctggagt gtacagggtg
 781 gacctcttca ctcgtcaagt gtcatctcct gacgtggact ggagctacgg tgagccaacc
 841 gagatgttat gcgccggttc caatgatgga gaggggatgg gtgagagtgg cggagcctac
 901 attgtgcgca taccgtgtgg gccgcgggat aaatacctca agaaggaagc gttgtggcct
 961 tacctccaag agtttgtcga tggagccctt gcgcatatcc tgaacatgtc caaggctctg
1021 ggagagcagg ttggaaatgg gaggccagta ctgccttacg tgatacatgg cactatgcc
1081 gatgctggag atgttgctgc tctcctttct ggtgcgctga atgtgccaat ggtgctcact
1141 ggccactcac ttgggaggaa caagctggaa caactgctga agcaagggcg catgtccaag
1201 gaggagatcg attcgacata caagatcatg aggcgtatcg agggtgagga gctggccctg
1261 gatgcgtcag agcttgtaat cacgagcaca aggcaggaga ttgatgagca gtggggattg
1321 tacgatggat ttgatgtcaa gcttgagaaa gtgctgaggg cacgggcgag gcgcggggtt
1381 agctgccatg gtcgttacat gcctaggatg gtggtgattc ctccgggaat ggatttcagc
1441 aatgttgtag ttcatgaaga cattgatggg gatggtgacg tcaaagatga tatcgttggt
1501 ttggagggtg cctcacccaa gtcaatgccc caatttgggc cgaagtgat gcggttcctg
1561 accaacccctc acaagccgat gatcctggcg ttatcaagac cagacccgaa gaagaacatc
1621 actaccctcg tcaaagcgtt tggagagtgt cgtccactca gggaacttgc aaaccttact
1681 ctgatcatgg taacagaga tgacatcgac gacatgtctg ctggcaatgc cagtgtcctc
1741 accacagttc tgaagctgat tgacaagtat gatctgtacg gaagcgtggc gttccctaag
1801 catcacaatc aggctgacgt cccggagatc tatcgcctcg cggccaaaat gaagggcgtc
1861 ttcatcaacc ctgctctcgt tgagccgttt ggtctcaccc tgatcgaggc tgcggcacac
1921 ggactcccga tagtcgctac caagaatggt ggtccggtcg acattacaaa tgcattaaac
1981 aacggactgc tcgttgaccc acacgaccag aacgccatcg ctgatgcact gctgaagctt
2041 gtggcagaca agaacctgtg gcaggaatgc cggagaaacg ggctgcgcaa catccacctc
2101 tactcatggc cggagcactg ccgcacttac ctcaccaggg tggccgggtg ccggttaagg
2161 aacccgaggt ggctgaagga cacaccagca gatgccggag ccgatgagga ggagttcctg
2221 gaggattcca tggacgctca ggacctgtca ctccgtctgt ccatcgacgg tgagaagagc
2281 tcgctgaaca ctaacgatcc actgtggttc gaccccagg atcaagtgca agatcatg
2341 aacaacatca gcagtcgtc agcgcttcct ccgtccatgt cctcagtcgc agccgagggc
```

FIGURE 15 (continued)

```
2401 acaggcagca ccatgaacaa atacccactc ctgcgccggc gccggcgctt gttcgtcata
2461 gctgtggact gctaccagga cgatggccgt gctagcaaga agatgctgca ggtgatccag
2521 gaagttttca gagcagtccg atcggactcc cagatgttca agatctcagg gttcacgctg
2581 tcgactgcca tgccgttgtc cgagacactc cagcttctgc agctcggcaa gatcccagcg
2641 accgacttcg acgccctcat ctgtggcagc ggcagcgagg tgtactatcc tggcacggcg
2701 aactgcatgg acgctgaagg aaagctgcgc ccagatcagg actatctgat gcacatcagc
2761 caccgctggt cccatgacgg cgcgaggcag accatagcga agctcatggg cgctcaggac
2821 ggttcaggcg acgctgtcga gcaggacgtg gcgtccagta atgcacactg tgtcgcgttc
2881 ctcatcaaag accccaaaa ggtgaaaacg gtcgatgaga tgagggagcg gctgaggatg
2941 cgtggtctcc gctgccacat catgtactgc aggaactcga caaggcttca ggttgtccct
3001 ctgctagcat caaggtcaca ggcactcagg tatctttccg tgcgctgggg cgtatctgtg
3061 gggaacatgt atctgatcac cggggaacat ggcgacaccg atctagagga gatgctatcc
3121 gggctacaca agaccgtgat cgtccgtggc gtcaccgaga agggttcgga agcactggtg
3181 aggagcccag gaagctacaa gagggacgat gtcgtcccgt ctgagacccc cttggctgcg
3241 tacacgactg gtgagctgaa ggccgacgag atcatgcggg ctctgaagca agtctccaag
3301 acttccagcg gcatgtgaat ttgatgcttc ttttacattt tgtccttttc ttcactgcta
3361 tataaaataa gttgtgaaca gtaccgcggg tgtgtatata tatattgcag tgacaaataa
3421 aacaggacac tgctaactat actggtgaat atacgactgt caagattgta tgctaagtac
3481 tccatttctc aatgtatcaa tcggaattc
```

SUGARCANE UBI9 GENE PROMOTER SEQUENCE AND METHODS OF USE THEREOF

This is a continuation-in-part of application Ser. No. 09/270,976, filed Mar. 17, 1999, which claims priority to provisional application Serial No. 60/078,767, filed Mar. 19, 1998, now abandoned.

This work was made with Government support by the United States Department of Agriculture. The Government has certain rights in this invention.

FIELD OF THE INVENTION

The invention relates to nucleic acid sequences isolated from sugarcane and to methods of using them. In particular, the inventions relates to nucleotide sequences which are derived from sugarcane polyubiquitin genes and which are capable of directing constitutive expression of a nucleic acid sequence of interest that is operably linked to the sugarcane polyubiquitin nucleotide sequences. The sugarcane polyubiquitin nucleotide sequences are useful in regulating expression of a nucleic acid sequence of interest in monocotyledonous and dicotyledonous plants.

BACKGROUND OF THE INVENTION

Much scientific effort has been directed at genetically engineering plants to produce agronomically relevant proteins. Recombinant genes for producing proteins in plants require a promoter sequence which is capable of directing protein expression in plant cells. Promoter sequences which direct high levels of protein expression in plant cells are particularly desirable since fewer numbers of transgenic plants need to be produced and screened to recover plants producing agronomically significant quantities of the target protein. In addition, high levels of protein expression aid the generation of plants which exhibit commercially important phenotypic properties, such as pest and disease resistance, resistance to environmental stress (e.g., water-logging, drought, heat, cold, light-intensity, day-length, chemicals, etc.), improved qualities (e.g., high yield of fruit, extended shelf-life, uniform fruit shape and color, higher sugar content, higher vitamins C and A content, lower acidity, etc.).

Some promoter sequences which are capable of driving expression of transgenes (e.g., selectable marker genes) in plants are known in the art and are derived from a variety of sources such as bacteria, plant DNA viruses, and plants. Promoters of bacterial origin include the octopine synthase promoter, the nopaline synthase promoter and other promoters derived from native Ti plasmids. Promoters of viral origin include the 35S and 19S RNA promoters of cauliflower mosaic virus. Plant promoters include the ribulose-1,3-diphosphate carboxylase small subunit promoter, the phaseolin promoter, and the maize polyubiquitin promoter.

While some promoter sequences which function in plant cells are available, expression of more than one gene (e.g., a selectable marker gene and an agronomically relevant gene) which is operably linked to the same promoter sequence is likely to be hampered by homology dependent silencing of transgenes in plants. Thus, what is needed are additional promoter sequences which are capable of driving transgene expression. In particular, what is needed are promoter sequences which drive transgene expression in both monocotyledonous and dicotyledonous plant cells.

SUMMARY OF THE INVENTION

The present invention provides nucleic acid sequences having promoter activity. The nucleic acid sequences provided herein direct expression of operably linked nucleotide sequences in cells, tissues and organs of monocotyledonous and dicotyledonous plants. In one embodiment, the invention provides a substantially purified nucleic acid sequence comprising a nucleotide sequence selected from the group consisting of SEQ ID NO:7, the complement of SEQ ID NO:7, homologs of SEQ ID NO:7, homologs of the complement of SEQ ID NO:7; SEQ ID NO:10, the complement of SEQ ID NO:10, homologs of SEQ ID NO:10, and homologs of the complement of SEQ ID NO:10. In a preferred embodiment, the nucleotide sequence is characterized by having promoter activity. In a more preferred embodiment, the promoter activity is constitutive. In another embodiment, nucleotide sequence is double-stranded. In yet another embodiment, the nucleotide sequence is single-stranded. In yet another alternative embodiment, the nucleic acid sequence is contained in a plant cell. In a preferred embodiment, the plant cell is derived from a monocotyledonous plant. In a more preferred embodiment, the monocotyledonous plant is selected from the group consisting of sugarcane, maize, sorghum, pineapple, rice, barley, oat, wheat, rye, yam, onion, banana, coconut, date, and hop. In an alternative more preferred embodiment, the plant cell is derived from a dicotyledonous plant. In a preferred embodiment, the dicotyledonous plant is selected from the group consisting of tobacco, tomato, soybean, and papaya.

The invention also provides a substantially purified nucleic acid sequence comprising a portion of a nucleotide sequence selected from the group consisting of SEQ ID NO:7 and the complement thereof. In a preferred embodiment, the portion is characterized by having promoter activity. In a more preferred embodiment, the promoter activity is constitutive. In an alternative preferred embodiment, the portion is double-stranded. In another alternative preferred embodiment, the portion is single-stranded. In yet another alternative preferred embodiment, the portion comprises the nucleotide sequence selected from the group consisting of the nucleotides from 1 to 242, from 245 to 787, from 788 to 1020, from 1021 to 1084, from 1085 to 1168, from 1169 to 1173, from 1174 to 1648, from 1649 to 1802, from 1 to 377, from 378 to 442, and from 443 to 1802. In a further alternative preferred embodiment, nucleic acid sequence is contained in a plant cell. In a more preferred embodiment, the plant cell is derived from a monocotyledonous plant. In a yet more preferred embodiment, the monocotyledonous plant is selected from the group consisting of sugarcane, maize, sorghum, pineapple, rice, barley, oat, wheat, rye, yam, onion, banana, coconut, date, and hop. In another more preferred embodiment, the plant cell is derived from a dicotyledonous plant. In a yet more preferred embodiment, the dicotyledonous plant is selected from the group consisting of tobacco, tomato, soybean, and papaya.

Further provided by the invention is a substantially purified nucleic acid sequence comprising a portion of a nucleotide sequence selected from the group consisting of SEQ ID NO:10 and the complement thereof. In a preferred embodiment, the portion is characterized by having promoter activity. In a more preferred embodiment, the promoter activity is constitutive. In an alternative preferred embodiment, the portion is double-stranded. In another alternative preferred embodiment, the portion is single-stranded. In yet another alternative preferred embodiment, the portion comprises the nucleotide sequence selected from the group consisting of the nucleotides 1 to 3600, from 3602 to 3612, from 3614 to 3688, from 1 to 2248, from 2249 to 2313, from 2314 to 3688, and from 1671 to 2248. In another alternative preferred embodiment, the nucleic acid sequence is contained in a plant cell. In a more preferred embodiment, the plant cell is derived from a monocotyledonous plant. In yet a more preferred embodiment, the monocotyledonous plant is selected from the group consisting of sugarcane, maize, sorghum, pineapple, rice, barley, oat, wheat, rye, yam, onion, banana, coconut, date, and hop. In an alternative more preferred embodiment, the plant cell is derived from a dicotyledonous plant. In a yet more preferred embodiment, the dicotyledonous plant is selected from the group consisting of tobacco, tomato, soybean, and papaya.

The invention additionally provides a substantially purified nucleic acid sequence comprising the EcoRI/XbaI fragment isolated from plasmid pubi4-GUS contained in *Escherichia coli* cells deposited as NRRLB-30115, the complement of the fragment, homologs of the fragment, and homologs of the complement of the fragment. In a preferred embodiment, the nucleotide sequence is SEQ ID NO:7. In a more preferred embodiment, the nucleotide sequence is characterized by having promoter activity. In a yet more preferred embodiment, the promoter activity is constitutive. In an alternative yet more preferred embodiment, the nucleotide sequence is double-stranded. In another alternative more preferred embodiment, the nucleotide sequence is single-stranded. In yet another alternative more preferred embodiment, the nucleic acid sequence is contained in a plant cell. In another preferred embodiment, the plant cell is derived from a monocotyledonous plant. In a more preferred embodiment, the monocotyledonous plant is selected from the group consisting of sugarcane, maize, sorghum, pineapple, rice, barley, oat, wheat, rye, yam, onion, banana, coconut, date, and hop. In an alternative preferred embodiment, the plant cell is derived from a dicotyledonous plant. In a yet more preferred embodiment, the dicotyledonous plant is selected from the group consisting of tobacco, tomato, soybean, and papaya.

Also provided herein is a substantially purified nucleic acid sequence comprising the HindIII/XbaI fragment isolated from plasmid pubi9-GUS contained in *Escherichia coli* cells deposited as NRRLB-30116, the complement of the fragment, homologs of the fragment, and homologs of the complement of the fragment. In a preferred embodiment, the nucleotide sequence is SEQ ID NO:10. In an alternative preferred embodiment, the nucleotide sequence is characterized by having promoter activity. In a more preferred embodiment, the promoter activity is constitutive. In another alternative preferred embodiment, the nucleotide sequence is double-stranded. In yet another alternative preferred embodiment, the nucleotide sequence is single-stranded. In another alternative preferred embodiment, the nucleic acid sequence is contained in a plant cell. In a more preferred embodiment, the plant cell is derived from a monocotyledonous plant. In a yet more preferred embodiment, the monocotyledonous plant is selected from the group consisting of sugarcane, maize, sorghum, pineapple, rice, barley, oat, wheat, rye, yam, onion, banana, coconut, date, and hop. In another more preferred embodiment, the plant cell is derived from a dicotyledonous plant. In a yet more preferred embodiment, the dicotyledonous plant is selected from the group consisting of tobacco, tomato, soybean, and papaya.

The invention further provides a substantially purified nucleic acid sequence comprising a portion of the EcoRI/XbaI fragment isolated from plasmid pubi4-GUS contained in *Escherichia coli* cells deposited as NRRLB-30115, and the complement of the fragment. In a preferred embodiment, the portion is characterized by having promoter activity. In a more preferred embodiment, the promoter activity is constitutive. In an alternative preferred embodiment, the portion is double-stranded. In another alterative preferred embodiment, the portion is single-stranded. In yet another alternative preferred embodiment, the nucleic acid sequence is contained in a plant cell. In a more preferred embodiment, the plant cell is derived from a monocotyledonous plant. In a yet more preferred embodiment, the monocotyledonous plant is selected from the group consisting of sugarcane, maize, sorghum, pineapple, rice, barley, oat, wheat, rye, yam, onion, banana, coconut, date, and hop. In an alternative more preferred embodiment, the plant cell is derived from a dicotyledonous plant. In yet a more preferred embodiment, the dicotyledonous plant is selected from the group consisting of tobacco, tomato, soybean, and papaya.

Also provided by the invention is a substantially purified nucleic acid sequence comprising a portion of the HindIII/XbaI fragment isolated from plasmid pubi9-GUS contained in *Escherichia coli* cells deposited as NRRLB-30116, and the complement of the fragment. In a preferred embodiment, the portion is characterized by having promoter activity. In a more preferred embodiment, the promoter activity is constitutive. In another preferred embodiment, the portion is double-stranded. In yet another preferred embodiment, the portion is single-stranded. In yet another preferred embodiment, the nucleic acid sequence is contained in a plant cell. In a more preferred embodiment, the plant cell is derived from a monocotyledonous plant. In a yet more preferred embodiment, the monocotyledonous plant is selected from the group consisting of sugarcane, maize, sorghum, pineapple, rice, barley, oat, wheat, rye, yam, onion, banana, coconut, date, and hop. In an alterative more preferred embodiment, the plant cell is derived from a dicotyledonous plant. In a yet more preferred embodiment, the dicotyledonous plant is selected from the group consisting of tobacco, tomato, soybean, and papaya.

The invention additionally provides a recombinant expression vector comprising a nucleotide sequence selected from the group consisting of SEQ ID NO:7, the complement of SEQ ID NO:7, homologs of SEQ ID NO:7, homologs of the complement of SEQ ID NO:7; SEQ ID NO:10, the complement of SEQ ID NO:10, homologs of SEQ ID NO:10, and homologs of the complement of SEQ ID NO:10. In a preferred embodiment, the recombinant expression vector is selected from the group consisting of pubi4-GUS, pubi9-GUS, pCAM-ubi4-GUS and pCAM-ubi9-GUS.

The invention also provides a recombinant expression vector comprising a portion of a nucleotide sequence selected from the group consisting of SEQ ID NO:7 and the complement thereof.

Also provided herein is a recombinant expression vector comprising a portion of a nucleotide sequence selected from the group consisting of SEQ ID NO:10 and the complement thereof.

Additionally provided by the invention is a transgenic plant cell comprising a nucleic acid sequence comprising a nucleotide sequence selected from the group consisting of SEQ ID NO:7, the complement of SEQ ID NO:7, homologs of SEQ ID NO:7, homologs of the complement of SEQ ID NO:7; SEQ ID NO:10, the complement of SEQ ID NO:10, homologs of SEQ ID NO:10, and homologs of the complement of SEQ ID NO:10, wherein the nucleotide sequence is operably linked to a nucleic acid sequence of interest. In a preferred embodiment, the transgenic plant cell expresses the nucleic acid sequence of interest. In a more preferred embodiment, the expression is constitutive. In an alternative embodiment, the transgenic plant cell is derived from a monocotyledonous plant. In a more preferred embodiment, the monocotyledonous plant is selected from the group consisting of sugarcane, maize, sorghum, pineapple, rice, barley, oat, wheat, rye, yam, onion, banana, coconut, date, and hop. In another alternative embodiment, the transgenic plant cell is derived from a dicotyledonous plant. In a more preferred embodiment, the dicotyledonous plant is selected from the group consisting of tobacco, tomato, soybean, and papaya. In yet another alternative embodiment, the nucleic acid sequence of interest is a sense sequence. In a more preferred embodiment, the sense sequence encodes a protein selected from the group consisting of β-glucuronidase, luciferase, β-galactosidase, 1-aminocyclopropane-1-carboxylic acid deaminase, sucrose phosphate synthase, 5-enolpyruvyl-3-phosphoshikimate synthase, acetolactate synthase, RNase, wheat germ agglutinin, sweetness protein, and *Bacillus thuringiensis* crystal toxin proteins. In a further alternative embodiment, the nucleic acid sequence of interest is an antisense sequence. In a more preferred embodiment, the antisense sequence is selected from the group consisting of an antisense sequence to ACC synthase, to ethylene inducible sequences, and to polyphenol oxidase.

The invention further provides a transgenic plant cell comprising a nucleic acid sequence comprising a portion of a nucleotide sequence selected from the group consisting of SEQ ID NO:7 and the complement thereof.

Also provided herein is a transgenic plant cell comprising a nucleic acid sequence comprising a portion of a nucleotide sequence selected from the group consisting of SEQ ID NO:10 and the complement thereof.

Additionally provided by the invention is a method for expressing a nucleic acid sequence of interest in a plant cell, comprising: a) providing: i) a plant cell; ii) a nucleic acid sequence of interest; and iii) a nucleotide sequence selected from the group consisting of SEQ ID NO:7, the complement of SEQ ID NO:7, homologs of SEQ ID NO:7, homologs of the complement of SEQ ID NO:7; SEQ ID NO:10, the complement of SEQ ID NO:10, homologs of SEQ ID NO:10, and homologs of the complement of SEQ ID NO:10; b) operably linking the nucleic acid sequence of interest to the nucleotide sequence to produce a transgene; and c) introducing the transgene into the plant cell to produce a transgenic plant cell under conditions such that the nucleic acid sequence of interest is expressed in the transgenic plant cell. In a preferred embodiment, the method further comprises d) identifying the transgenic plant cell. In another preferred embodiment, the method further comprises d) regenerating transgenic plant tissue from the transgenic plant cell. In an alternative preferred embodiment, the methods further comprises d) regenerating a transgenic plant from the transgenic plant cell. In another preferred embodiment, the plant cell is derived from a monocotyledonous plant. In yet a more preferred embodiment, the monocotyledonous plant is selected from the group consisting of sugarcane, maize, sorghum, pineapple, rice, barley, oat, wheat, rye, yam, onion, banana, coconut, date, and hop. In another alterative more preferred embodiment the plant cell is derived from a dicotyledonous plant. In a yet more preferred embodiment, the dicotyledonous plant is selected from the group consisting of tobacco, tomato, soybean, and papaya.

The invention further provides a method for expressing a nucleic acid sequence of interest in a plant cell, comprising: a) providing: i) a plant cell; ii) a nucleic acid sequence of interest; and iii) a portion of a nucleotide sequence selected from the group consisting of SEQ ID NO:7 and the complement thereof; b) operably linking the nucleic acid sequence of interest to the portion of a nucleotide sequence to produce a transgene; and c) introducing the transgene into the plant cell to produce a transgenic plant cell under conditions such that the nucleic acid sequence of interest is expressed in the transgenic plant cell. In a preferred embodiment, the portion comprises the nucleotide sequence selected from the group consisting of the nucleotides from 1 to 242, from 245 to 787, from 788 to 1020, from 1021 to 1084, from 1085 to 1168, from 1169 to 1173, from 1174 to 1648, from 1649 to 1802, from 1 to 377, from 378 to 442, and from 443 to 1802.

Also provided by the invention is a method for expressing a nucleic acid sequence of interest in a plant cell, comprising: a) providing: i) a plant cell; ii) a nucleic acid sequence of interest; and iii) a portion of a nucleotide sequence selected from the group consisting of SEQ ID NO:10 and the complement thereof; b) operably linking the nucleic acid sequence of interest to the portion of a nucleotide sequence to produce a transgene; and c) introducing the transgene into the plant cell to produce a transgenic plant cell under conditions such that the nucleic acid sequence of interest is expressed in the transgenic plant cell. In a preferred embodiment, the portion comprises the nucleotide sequence selected from the group consisting of the nucleotides 1 to 3600, from 3602 to 3612, from 3614 to 3688, from 1 to 2248, from 2249 to 2313, from 2314 to 3688, and from 1671 to 2248.

The invention further provides a transgenic plant cell comprising a nucleotide sequence selected from at least a portion of SEQ ID NO:7 and at least a portion of SEQ ID NO:10, wherein the nucleotide sequence is operably linked to a nucleic acid sequence of interest, and the plant is selected from sugar cane, tobacco, sorghum, pineapple, rice, maize, tomato, soybean, banana, and garlic. In one preferred embodiment, the portion of SEQ ID NO:7 comprises the nucleotide sequence selected from the nucleotides from 1 to 242, from 245 to 787, from 788 to 1020, from 1021 to 1084, from 1085 to 1168, from 1169 to 1173, from 1174 to 1648, from 1649 to 1802, from 1 to 377, from 378 to 442, and from 443 to 1802, and the portion of SEQ ID NO:10 comprises the nucleotide sequence selected from the nucleotides from 1 to 3600, from 3602 to 3612, from 3614 to 3688, from 1 to 2248, from 2249 to 2313, from 2314 to 3688, and from 1671 to 2248. In an alternative preferred embodiment, the plant is garlic. In another alternative embodiment, the plant cell is selected from leaf cell, root cell, fruit cell, and embryonic cell. In a further preferred embodiment, the plant cell is transiently transformed. In yet a further preferred embodiment, the plant cell is stably transformed.

The invention also provides a transgenic plant cell comprising a nucleotide sequence selected from a functional homolog of SEQ ID NO:7 having promoter activity, and a homolog of SEQ ID NO:10 having promoter activity, wherein the nucleotide sequence is operably linked to a nucleic acid sequence of interest, and the plant is selected from sugar cane, tobacco, sorghum, pineapple, rice, maize, tomato, soybean, banana, and garlic.

Additionally provided herein is a method for expressing a nucleic acid sequence of interest in a plant cell selected from sugar cane, tobacco, sorghum, pineapple, rice, maize, tomato, soybean, banana, and garlic, comprising: a) providing: i) the plant cell; ii) a nucleic acid sequence of interest; and iii) a nucleotide sequence selected from at least a portion of SEQ ID NO:7 having promoter activity, and at least a portion of SEQ ID NO:10 having promoter activity; b) operably linking the nucleic acid sequence of interest to the nucleotide sequence to produce a transgene; and c) introducing the transgene into the plant cell to produce a transgenic plant cell under conditions such that the nucleic acid sequence of interest is expressed in the transgenic plant cell. In one preferred embodiment, the method further comprises d) identifying the transgenic plant cell. In another preferred embodiment, the method further comprises d) regenerating transgenic plant tissue from the transgenic plant cell. In yet another preferred embodiment, the method further comprises d) regenerating a transgenic plant from the transgenic plant cell. In an alternative preferred embodiment, the plant is garlic. In another alternative embodiment, the plant cell is selected from leaf cell, root cell, fruit cell, and embryonic cell. In a further preferred embodiment, the transgenic plant cell is transiently transformed. In an alternative preferred embodiment, the transgenic cell is stably transformed.

BRIEF DESCRIPTION OF THE DRAWINGS

FIGS. 3(A–B) shows the nucleotide sequence of the sugarcane polyubiquitin ubi4 gene. FIG. 3A shows the nucleotide sequence (SEQ ID NO:1) including the translation start codon and sequences upstream thereof. FIG. 3B shows the nucleotide sequence (SEQ ID NO:2) including the translation stop codon and sequences downstream thereof. Boldface indicates putative TATA box, ATG translation initiation codon, TAA translation stop codon, and putative poly-A addition signal; underlining indicates the putative 5' and 3' UTRs, based on homology to scubi241 and 511 cDNAs; lowercase indicates that the base is as depicted but with some uncertainty (see also Tables 1 and 2 below).

FIGS. 5(A–B) shows the nucleotide sequence (SEQ ID NO:5) (nucleotides 1 to 5512 of the 5551 nucleotide sequence deposited as GenBank accession number AF093504) (A) and translated amino acid sequence (SEQ ID NO:6) (B) of sugarcane polyubiquitin ubi4 gene.

FIG. 6 is a diagrammatic representation of the organization of ubi4 (GenBank accession number AF093504) and ubi9 (GenBank accession number AF093505) polyubiquitin genes. Numbered white boxes indicate polyubiquitin coding repeats, unnumbered white boxes are 5' and 3' untranslated regions, black boxes are introns and lines are flanking DNA. E: EcoRI; N: NruI; S: SalI; H: HindIII; M: putative miniature inverted-repeat transposable element.

FIGS. 7(A–B) shows the nucleotide sequence of the sugarcane polyubiquitin ubi9 gene. FIG. 7A shows the nucleotide sequence (SEQ ID NO:3) including the translation start codon and sequences upstream thereof. FIG. 7B shows the nucleotide sequence (SEQ ID NO:4) including the translation stop codon and sequences downstream thereof. Boldface indicates the putative TATA box, ATG translation start codon, TAA translation stop codon, and putative poly-A addition signal; underlining indicates the 5' and 3' UTRs; lowercase indicates that the base is most probably as depicted (see also Tables 4 and 5 below).

FIGS. 8(A–B) shows the nucleotide sequence (SEQ ID NO:8) (GenBank accession number AF093505) (A) and translated amino acid sequence (SEQ ID NO:9) (B) of the sugarcane polyubiquitin ubi9 gene.

FIG. 10 shows the nucleotide sequence (SEQ ID NO:7) of the portion of the ubi4 gene which was ligated to the gene encoding β-glucuronidase (GUS) in plasmids pubi4-GUS and pCAM-ubi4-GUS. SEQ ID NO:7 corresponds to nucleotides 1–1802 of SEQ ID NO:5.

FIG. 11 shows the nucleotide sequence (SEQ ID NO:10) of the portion of the ubi9 gene which was ligated to the gene encoding β-glucuronidase (GUS) in plasmids pubi9-GUS and pCAM-ubi9-GUS. SEQ ID NO:10 corresponds to nucleotides 1–3688 of SEQ ID NO:8.

FIG. 14 shows the nucleotide sequence (SEQ ID NO:11) encoding polyphenol oxidase (GenBank accession number s40548).

FIG. 15 shows the nucleotide sequence (SEQ ID NO:2) encoding maize sucrose phosphate synthase enzyme (GenBank accession number m97550).

DEFINITIONS

Figure 1:
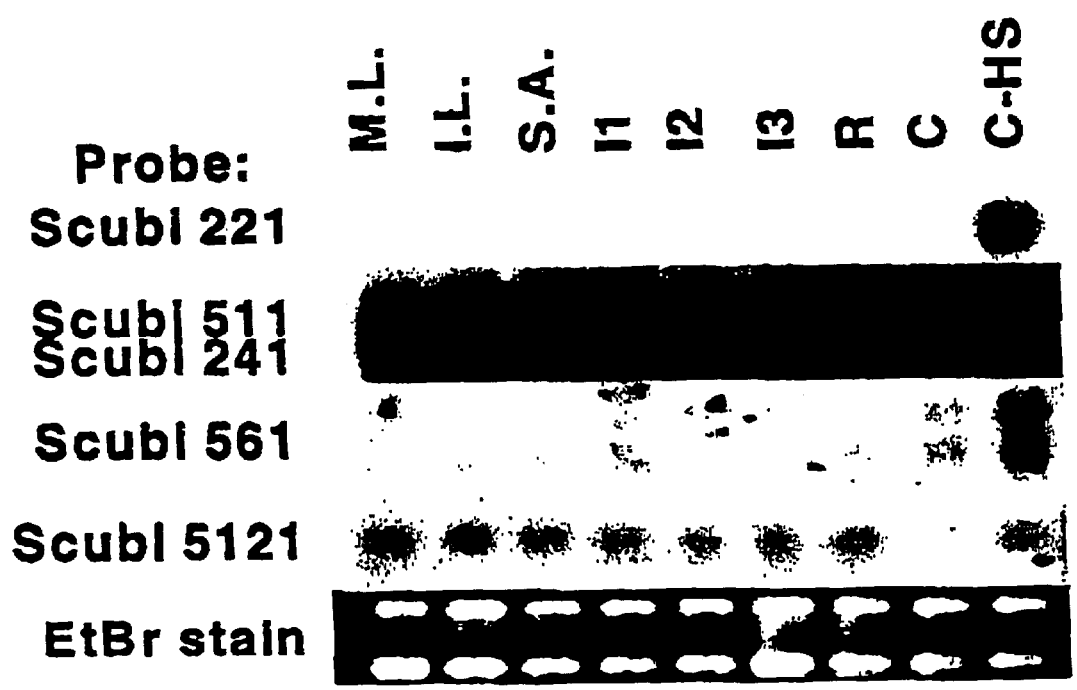
FIG. 1 shows a RNA gel blot of sugarcane polyubiquitin mRNA pools hybridized to gene-specific probes for Scubi 221, Scubi 511, Scubi 241, Scubi561, and Scubi 5121.

To facilitate understanding of the invention, a number of terms are defined below.

The term "transgenic" when used in reference to a cell refers to a cell which contains a transgene, or whose genome has been altered by the introduction of a transgene. The term "transgenic" when used in reference to a tissue or to a plant refers to a tissue or plant, respectively, which comprises one or more cells that contain a transgene, or whose genome has been altered by the introduction of a transgene. Transgenic cells, tissues and plants may be produced by several methods including the introduction of a "transgene" comprising nucleic acid (usually DNA) into a target cell or integration of the transgene into a chromosome of a target cell by way of human intervention, such as by the methods described herein.

The term "transgene" as used herein refers to any nucleic acid sequence which is introduced into the genome of a cell by experimental manipulations. A transgene may be an "endogenous DNA sequence," or a "heterologous DNA sequence" (i.e., "foreign DNA"). The term "endogenous DNA sequence" refers to a nucleotide sequence which is naturally found in the cell into which it is introduced so long as it does not contain some modification (e.g., a point mutation, the presence of a selectable marker gene, etc.) relative to the naturally-occurring sequence. The term "heterologous DNA sequence" refers to a nucleotide sequence which is ligated to, or is manipulated to become ligated to, a nucleic acid sequence to which it is not ligated in nature, or to which it is ligated at a different location in nature. Heterologous DNA is not endogenous to the cell into which it is introduced, but has been obtained from another cell. Heterologous DNA also includes an endogenous DNA sequence which contains some modification. Generally, although not necessarily, heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), etc.

The term "foreign gene" refers to any nucleic acid (e.g., gene sequence) which is introduced into the genome of a cell by experimental manipulations and may include gene sequences found in that cell so long as the introduced gene contains some modification (e.g., a point mutation, the presence of a selectable marker gene, etc.) relative to the naturally-occurring gene.

The term "transformation" as used herein refers to the introduction of a transgene into a cell. Transformation of a cell may be stable or transient. The term "transient transformation" or "transiently transformed" refers to the introduction of one or more transgenes into a cell in the absence of integration of the transgene into the host cell's genome. Transient transformation may be detected by, for example, enzyme-linked immunosorbent assay (ELISA) which detects the presence of a polypeptide encoded by one or more of the transgenes. Alternatively, transient transformation may be detected by detecting the activity of the protein (e.g., β-glucuronidase) encoded by the transgene (e.g., the uid A gene) as demonstrated herein [e.g., histochemical assay of GUS enzyme activity by staining with X-gluc which gives a blue precipitate in the presence of the GUS enzyme; and a chemiluminescent assay of GUS enzyme activity using the GUS-Light kit (Tropix)]. The term "transient transformant" refers to a cell which has transiently incorporated one or more transgenes. In contrast, the term "stable transformation" or "stably transformed" refers to the introduction and integration of one or more transgenes into the genome of a cell. Stable transformation of a cell may be detected by Southern blot hybridization of genomic DNA of the cell with nucleic acid sequences which are capable of binding to one or more of the transgenes. Alternatively, stable transformation of a cell may also be detected by the polymerase chain reaction of genomic DNA of the cell to amplify transgene sequences. The term "stable transformant" refers to a cell which has stably integrated one or more transgenes into the genomic DNA. Thus, a stable transformant is distinguished from a transient transformant in that, whereas genomic DNA from the stable transformant contains one or more transgenes, genomic DNA from the transient transformant does not contain a transgene.

The term "nucleotide sequence of interest" refers to any nucleotide sequence, the manipulation of which may be deemed desirable for any reason (e.g., confer improved qualities), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product, (e.g., promoter sequence, polyadenylation sequence, termination sequence, enhancer sequence, etc.).

The term "isolated" when used in relation to a nucleic acid, as in "an isolated nucleic acid sequence" refers to a nucleic acid sequence that is identified and separated from at least one contaminant nucleic acid with which it is ordinarily associated in its natural source. Isolated nucleic acid is nucleic acid present in a form or setting that is different from that in which it is found in nature. In contrast, non-isolated nucleic acids are nucleic acids such as DNA and RNA which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs which encode a multitude of proteins. However, an isolated nucleic acid sequence comprising SEQ ID NO:7 includes, by way of example, such nucleic acid sequences in cells which ordinarily contain SEQ ID NO:7 where the nucleic acid sequence is in a chromosomal or extrachromosomal location different from that of natural cells, or is otherwise flanked by a different nucleic acid sequence than that found in nature. The isolated nucleic acid sequence may be present in single-stranded or double-stranded form. When an isolated nucleic acid sequence is to be utilized to express a protein, the nucleic acid sequence will contain at a minimum at least a portion of the sense or coding strand (i.e., the nucleic acid sequence may be single-stranded). Alternatively, it may contain both the sense and anti-sense strands (i.e., the nucleic acid sequence may be double-stranded).

As used herein, the term "purified" refers to molecules, either nucleic or amino acid sequences, that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated.

As used herein, the terms "complementary" or "complementarity" are used in reference to nucleotide sequences related by the base-pairing rules. For example, the sequence 5'-AGT-3' is complementary to the sequence 5'-ACT-3'. Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands.

A "complement" of a nucleic acid sequence as used herein refers to a nucleotide sequence whose nucleic acids show total complementarity to the nucleic acids of the nucleic acid sequence.

The term "homology" when used in relation to nucleic acids refers to a degree of complementarity. There may be partial homology (i.e., partial identity) or complete homology (i.e., complete identity). A partially complementary sequence is one that at least partially inhibits a completely complementary sequence from hybridizing to a target nucleic acid and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe (i.e., an oligonucleotide which is capable of hybridizing to another oligonucleotide of interest) will compete for and inhibit the binding (i.e., the hybridization) of a completely homologous sequence to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target. Thus, a "homolog" of a first nucleotide sequence refers to a nucleic acid sequence which can hybridize to the nucleotide sequence under conditions of low stringency, as described infra.

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described infra.

When used in reference to a single-stranded nucleic acid sequence, the term "substantially homologous" refers to any probe which can hybridize to the single-stranded nucleic acid sequence under conditions of low stringency as described infra.

The term "hybridization" as used herein includes "any process by which a strand of nucleic acid joins with a complementary strand through base pairing." [Coombs J (1994) *Dictionary of Biotechnology*, Stockton Press, New York N.Y.]. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl [see e.g., Anderson and Young, Quantitative Filter Hybridization, in *Nucleic Acid Hybridization* (1985)]. Other references include more sophisticated computations which take structural as well as sequence characteristics into account for the calculation of $T_m$.

Low stringency conditions when used in reference to nucleic acid hybridization comprise conditions equivalent to binding or hybridization at 68° C. in a solution consisting of 5×SSPE (43.8 g/l NaCl, 6.9 g/l NaH$_2$PO$_4$.H$_2$O and 1.85 g/l EDTA, pH adjusted to 7.4 with NaOH), 1% SDS, 5×Denhardt's reagent [50×Denhardt's contains the following per 500 ml: 5 g Ficoll (Type 400, Pharmacia), 5 g BSA (Fraction V; Sigma)] and 100 μg/ml denatured salmon sperm DNA followed by washing in a solution comprising 0.2× SSPE, and 0.1% SDS at room temperature when a DNA probe of about 100 to about 1000 nucleotides in length is employed.

High stringency conditions when used in reference to nucleic acid hybridizatiton comprise conditions equivalent to binding or hybridization at 68° C. in a solution consisting of 5×SSPE, 1% SDS, 5×Denhardt's reagent and 100 μg/ml denatured salmon sperm DNA followed by washing in a solution comprising 0.1×SSPE, and 0.1% SDS at 68° C. when a probe of about 100 to about 1000 nucleotides in length is employed.

The term "equivalent" when made in reference to a hybridization condition as it relates to a hybridization condition of interest means that the hybridization condition and the hybridization condition of interest result in hybridization of nucleic acid sequences which have the same range of percent (%) homology. For example, if a hybridization condition of interest results in hybridization of a first nucleic acid sequence with other nucleic acid sequences that have from 50% to 70% homology to the first nucleic acid sequence, then another hybridization condition is said to be equivalent to the hybridization condition of interest if this other hybridization condition also results in hybridization of the first nucleic acid sequence with the other nucleic acid sequences that have from 50% to 70% homology to the first nucleic acid sequence.

When used in reference to nucleic acid hybridization the art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above-listed conditions.

Those skilled in the art know that whereas higher stringencies may be preferred to reduce or eliminate non-specific binding between the nucleotide sequence of SEQ ID NOs:7 and 10 and other nucleic acid sequences, lower stringencies may be preferred to detect a larger number of nucleic acid sequences having different homologies to the nucleotide sequence of SEQ ID NOs:7 and 10.

The term "promoter," "promoter element," or "promoter sequence" as used herein, refers to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest whose transcription into mRNA it controls, and provides a site for specific binding by RNA polymerase and other transcription factors for initiation of transcription.

Promoters may be tissue specific or cell specific. The term "tissue specific" as it applies to a promoter refers to a promoter that is capable of directing selective expression of a nucleotide sequence of interest to a specific type of tissue (e.g., petals) in the relative absence of expression of the same nucleotide sequence of interest in a different type of tissue (e.g., roots). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining. Briefly, tissue sections are embedded in paraffin, and paraffin sections are reacted with a primary antibody which is specific for the polypeptide product encoded by the nucleotide sequence of interest whose expression is controlled by the promoter. A labeled (e.g., peroxidase conjugated) secondary antibody which is specific for the primary antibody is allowed to bind to the sectioned tissue and specific binding detected (e.g., with avidin/biotin) by microscopy.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue. In contrast, a "regulatable" promoter is one which is capable of directing a level of transcription of an operably linked nuclei acid sequence in the presence of a stimulus (e.g., heat shock, chemicals, light, etc.) which is different from the level of transcription of the operably linked nucleic acid sequence in the absence of the stimulus.

The terms "infecting" and "infection" with a bacterium refer to co-incubation of a target biological sample, (e.g., cell, tissue, etc.) with the bacterium under conditions such that nucleic acid sequences contained within the bacterium are introduced into one or more cells of the target biological sample.

The term "Agrobacterium" refers to a soil-borne, Gram-negative, rod-shaped phytopathogenic bacterium which causes crown gall. The term "Agrobacterium" includes, but is not limited to, the strains *Agrobacterium tumefaciens*, (which typically causes crown gall in infected plants), and *Agrobacterium rhizogens* (which causes hairy root disease in infected host plants). Infection of a plant cell with Agrobacterium generally results in the production of opines (e.g., nopaline, agropine, octopine etc.) by the infected cell. Thus, Agrobacterium strains which cause production of nopaline (e.g., strain LBA4301, C58, A208) are referred to as "nopaline-type" Agrobacteria; Agrobacterium strains which cause production of octopine (e.g., strain LBA4404, Ach5, B6) are referred to as "octopine-type" Agrobacteria; and Agrobacterium strains which cause production of agropine (e.g., strain EHA105, EHA101, A281) are referred to as "agropine-type" Agrobacteria.

The terms "bombarding, "bombardment," and "biolistic bombardment" refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807, the contents of which are herein incorporated by reference), and are commercially available (e.g., the helium gas-driven microprojectile accelerator (PDS-1000/He) (BioRad).

The term "microwounding" when made in reference to plant tissue refers to the introduction of microscopic wounds in that tissue. Microwounding may be achieved by, for example, particle bombardment as described herein.

The term "plant" as used herein refers to a plurality of plant cells which are largely differentiated into a structure that is present at any stage of a plant's development. Such structures include, but are not limited to, a fruit, shoot, stem, leaf, flower petal, etc. The term "plant tissue" includes differentiated and undifferentiated tissues of plants including, but not limited to, roots, shoots, leaves, pollen, seeds, tumor tissue and various types of cells in culture (e.g., single cells, protoplasts, embryos, callus, protocorm-like bodies, etc.). Plant tissue may be in planta, in organ culture, tissue culture, or cell culture.

The term "embryonic cell" as used herein in reference to a plant cell refers to one or more plant cells (whether differentiated or un-differentiated) which are capable of differentiation into a plant tissue or plant. Embryonic cells include, without limitation, protoplasts such as those derived from the genera Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Hyoscyamus, Lycopersicon, Nicotiana, Solanum, Petunia, Digitalis, Majorana, Ciohorium, Helianthus, Lactuca, Bromus, Asparagus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum, and Datura. Also included are embryos such as those from sorghum (Example 5), from maize (Example 10, U.S. Pat. No. 5,593,874 incorporated by reference), and from banana (Example 13), embryonic meristems such as those from soybean (Example 12; U.S. Pat. No. 5,015,580 incorporated by reference), embryogenic callus such as from sugarcane (Example 15), protocorm-like bodies such as from pineapple (Example 6), and embryogenic cells as exemplified by those from garlic (Example 16). The ability of an embryonic cell to differentiate into a plant is determined using methods known in the art as well as methods described herein. For example, differentiation of pineapple protocorm-like bodies into shoots may be accomplished by culturing the protocorm-like body on agar-solidified hormone-free modified Murashige & Skoog (MS) medium or on agar-solidified PM2 medium (U.S. Pat. No. 6,091,003 incorporated by reference). Differentiation into pineapple roots may be accomplished by culture of protocorm-like bodies in liquid modified MS medium containing 1 mg/L NAA.

DESCRIPTION OF THE INVENTION

The present invention provides nucleic acid sequences having promoter activity. The nucleic acid sequences provided herein direct constitutive expression of operably linked nucleotide sequences in cells, tissues and organs of monocotyledonous and dicotyledonous plants. The promoter sequences provided herein were discovered by screening highly expressed sugarcane polyubiquitin genes. The sequences of the invention are capable of driving expression of operably linked nucleotide sequences in plant cells at a level which is comparable to or greater than those levels expressed under the control of the prior art's maize polyubiquitin promoter sequences. Also provided by the invention are methods for constitutive expression of a nucleic acid sequence of interest in plants. The nucleic acid sequences and methods of the invention allow generation of transgenic plants which exhibit agronomically desirable characteristics.

The invention is further described under (A) Sugarcane Polyubiquitin Promoter Sequences, (B) Using Probes To Identify And Isolate Homologs of The Sugarcane Promoter Sequences, (C) Using Primers to Amplify Nucleotide Sequences, and (D) Generating Transgenic Plants.

A. Sugarcane Polyubiquitin Promoter Sequences

Ubiquitin involvement has been shown in protein turnover, heat shock response, and many other important cellular processes [Hershko et al., Annual Review of Biochemistry 61, 761–808 (1992)]. Consistent with its essential biological roles, the structure of the protein is very highly conserved in all eukaryotes [Callis et al., Genetics 139, 921–39 (1995); Callis et al., Oxford Surv Plant Mol Cell Biol 6, 1–30 (1989); Sun et al., Plant J 11, 1017–27 (1997)]. Many genes encoding ubiquitin contain various numbers of tandem repeats of the entire protein coding region and hence are called polyubiquitin genes. The primary translation product is a polyprotein, which is processed to form ubiquitin monomers post-translationally.

Ubiquitin protein is abundant throughout the plant body, and several polyubiquitin genes have been shown to be expressed in most or all cell types under most or all environmental conditions [Kawalleck et al., Plant Mol Biol 21, 673–84 (1993)]. Numerous other polyubiquitin genes, however, are expressed in a tissue-specific manner [Callis et al., Proc Natl Acad Sci USA 91, 6074–7 (1994); Plesse et al., Mol Gen Genet 254, 258–66 (1997)], or in response to environmental signals such as heat stress [Christensen et al., Plant Molecular Biology 12, 619–632 (1989); Liu et al., Biochem Cell Biol 73, 19–30 (1995)], or both [Almoguera et al., Plant Physiology 107, 765–773 (1995); Binet et al., Plant Mol Biol 17, 395–407 (1991); Burke et al., Mol Gen Genet 213, 435–43 (1988); Garbarino et al., Plant Mol Biol 20, 235–44 (1992); Genschik et al., Gene 148, 195–202 (1994); Sun et al. (1997) supra; Takimoto et al., Plant Mol Biol 26, 1007–12 (1994)]. Several polyubiquitin promoters have been isolated and used to drive transgene expression [Christensen et al., Plant Mol Biol 18, 675–89 (1992); Garbarino et al., Plant Physiology 109, 1371–1378 (1995)], including some which have been widely used for constitutive expression of genes in plant transformation [Christensen et al., Transgenic Research 5, 213–218 (1996); Gallo-Meagher et al., Plant Cell Reporter 12, 666–670 (1993); Garbarino et al. (1995) supra; Taylor et al., Plant Cell Reports 12, 491–495 (1993); Quail et al., U.S. Pat. Nos. 5,614,399 and 5,510,474].

All Saccharum species are polyploid and most are at least octoploid (2N=40–128 or more). Commercial sugarcane cultivars are all Saccharum species hybrids derived from 2N+N chromosome transmission [Sreenivasan et al.: Cytogenics. In: Heinz D J (ed) Sugarcane Improvement Through Breeding, pp. 211–253. Elsevier, Amsterdam (1987)]. This suggests that sugarcane hybrids may have at least twelve alleles for each of the multiple genes that make up the polyubiquitin gene family.

The nucleic acid sequences of the invention were discovered during a search by the inventors for promoters which are suitable for high-level constitutive transgene expression in monocotyledonous and dicotyledonous plants. The inventors isolated five polyubiquitin cDNA clones (scubi221, 241, 511, 561, and 5121) from sugarcane stem tissue [Albert et al., Plant Physiology 109, 337 (1995)]. Based on comparison of their 3' untranslated sequences, the inventors then grouped these five genes into four "sub-families." The inventors' investigation of the expression of two members of these four sub-families and isolated genomic clones, led to isolation of clones which contained promoters for two members of the most highly expressed sub-family.

The invention provides the nucleic acid sequence of two members of the sugarcane polyubiquitin family, the ubi4 gene and the ubi9 gene. Referring to the ubi4 gene, the initially determined nucleic acid sequence (SEQ ID NO:1) of the ubi4 gene including the translation start codon (ATG) and the sequence upstream of the translation start codon is shown in FIG. 3A, and the nucleic acid sequence (SEQ ID NO:2) of the ubi4 gene including the translation stop codon and sequences downstram of the translation stop codon is shown in FIG. 3B. The subsequently determined nucleic acid sequence (SEQ ID NO:5) of the entire ubi4 gene is shown in FIG. 5A with the subsequently determined nucleic acid sequence (SEQ ID NO:7) located upstream of the translation start codon of the ubi4 gene being shown in FIG. 10. The nucleotide sequence of FIG. 5A represents nucleotides 1 to 5512 of the 5551 nucleotide sequence deposited as GenBank accession number AF093504.

Fragments of the ubi4 gene sequence which were identical in the initially determined and the subsequently determined nucleic acid sequences were as follows (the nucleotide numbers refer to the nucleotide number in SEQ ID NO:5): Fragment A: 1–242; fragment B: 245–787; fragment C: 788–1020; fragment D: 1021–1084; fragment E: 1085–1168; fragment F: 1169–1173; fragment G: 1174–1648; and fragment H: 1649–1805. The nucleotide sequence upstream of the transcription start codon of the ubi4 gene (i.e., nucleotides 1–1810 of SEQ ID NO:1, and nucleotides 1–1802 of SEQ ID NOs:5 and 7) contained three regions: (a) an upstream of the 5' UTR sequence (i.e., nucleotides 1–378 of SEQ ID NO:1, and nucleotides 1–377 of SEQ ID NOs:5 and 7), (b) a 5' UTR sequence (i.e., nucleotides 379–444 of SEQ ID NO:1, and nucleotides 378–442 of SEQ ID NOs:5 and 7); and (c) an intron sequence (i.e., nucleotides 445–1810 of SEQ ID NO:1, and nucleotides 443–1802 of SEQ ID NOs:5 and 7).

With respect of the ubi9 gene, the initially determined nucleic acid sequence (SEQ ID NO:3) of the ubi9 gene including the translation start codon and sequences upstream thereof is shown in FIG. 7A and the initially determined nucleic acid sequence (SEQ ID NO:4) of the ubi9 gene including the translation stop codon and sequences downstream thereof is shown in FIG. 7B. The subsequently determined nucleic acid sequence (SEQ ID NO:8) of the entire ubi9 gene is shown in FIG. 8A, with the nucleic acid sequence (SEQ ID NO:10) of the ubi9 gene upstream of the translation start codon being shown in FIG. 11.

It is noted that while the 5' end of the ubi9 gene was obtained by cleavage with HindIII which recognizes the sequence 5'-AAGCTT-3', repeated sequencing of the 5'-end of the ubi9 gene showed instead the sequence 5'-AAGTTT-3' (FIGS. 8 and 11). Thus, it is the inventors' view that the sequence of the full-length ubi9 gene (a) is as shown in FIG. 8A (SEQ ID NO:8) (i.e., total number of nucleotides being 5174, with the ten nucleotides at the 5'-end being 5'-AAGTTTTGnT-3') (SEQ ID NO:13), (b) is as shown in FIG. 8A (SEQ ID NO:8) with the exception that it has a total number of nucleotides of 5174, with the ten nucleotides at the 5'-end being 5'-AAGCTTTGnT-3' (SEQ ID NO: 14), assuming substitution of the "T" at position 4 with a "C"), or (c) is as shown in FIG. 8A (SEQ ID NO:8) with the exception that it has a total number of nucleotides of 5175, with the ten nucleotides at the 5'-end being 5'-AAGCTTTTGn-3' (SEQ ID NO: 15), assuming insertion of a "C" at position 4. Accordingly, any reference herein to SEQ ID NO:8 is intended to mean each and every one of the three nucleotide sequences described in the preceding sentence.

Similarly, it is the inventors' view that the sequence upstream of the translation start codon of the ubi9 gene (a) is as shown in FIG. 11 (SEQ ID NO:10) (i.e., total number of nucleotides being 3688, with the ten nucleotides at the 5'-end being 5'-AAGTTTTGnT-3') (SEQ ID NO:16), (b) is as shown in FIG. 11 (SEQ ID NO:10) with the exception that it has a total number of nucleotides of 3688, with the ten nucleotides at the 5'-end being 5'-AAGCTTTGnT-3' (SEQ ID NO:14), assuming substitution of the "T" at position 4 with a "C"), or (c) is as shown in FIG. 11 (SEQ ID NO:10) with the exception that it has a total number of nucleotides of 3689, with the ten nucleotides at the 5'-end being 5'-AAGCTTTTGn-3' (SEQ ID NO:15), assuming insertion of a "C" at position 4. Accordingly, any reference herein to SEQ ID NO:10 is intended to mean each and every one of the three nucleotide sequences described in the preceding sentence.

Fragments of the ubi9 gene sequence which were identical in the initially determined and the subsequently determined nucleic acid sequences were as follows (the nucleotide number refers to the nucleotide number in SEQ ID NO:8): Fragment A: 1–3600; fragment B: 3602–3612; and fragment C: 3614–3691. The nucleotide sequence upstream of the translation start codon of the ubi9 gene (i.e., nucleotides 1- 3691 of SEQ ID NO:3, and nucleotides 1–3691 of SEQ ID NO:8) contained three regions: (a) an upstream of the 5' UTR sequence (i.e., nucleotides 1–2248 of SEQ ID NO:3, and nucleotides 1–2248 of SEQ ID NOs:8 and 10), (b) a 5' UTR sequence (i.e., nucleotides 2249–2313 of SEQ ID NO:3, and nucleotides 2249–2313 of SEQ ID NOs:8 and 10), and (c) an intron sequence (i.e., nucleotides 2314–3688 of SEQ ID NO:3, and nucleotides 2314–3688 of SEQ ID NOs:8 and 10). A BLAST search of the GenBank database showed 100% homology to only a 20–22 bp region of nucleotides 1–3688 of SEQ ID NOs:8 and 10 (i.e. the region of the ubi9 gene which contained the sequence upstream of the 5' UTR, the 5' UTR sequence, and the intron sequence), 100% homology to only a 20 bp region of nucleotides 1–2248 of SEQ ID NOs:8 and 10 (i.e., the sequence upstream of the 5' UTR), and 87% homology between a 135 bp fragment of the sequence upstream of the 5' UTR of SEQ ID NOs:8 and 10 and a 118 bp fragment of Saccharum sp. glucose transporter mRNA, 3' end (GenBank accession number L21752).

Data presented herein demonstrates that plasmids which contain the uid A gene encoding β-glucuronidase (GUS) under the control of SEQ ID NO:7 (which is equivalent to the initially determined SEQ ID NO:1) of the ubi4 gene or under the control of SEQ ID NO:10 (which is equivalent to the initially determined SEQ ID NO:3) of the ubi9 gene successfully drive transient expression of GUS in monocotyledonous sugarcane suspension cultured cells (Example 3), monocotyledonous sorghum callus (Example 5), monocotyledonous pineapple leaves, protocorm-like bodies, roots and fruit (Example 6), and in dicotyledonous tobacco leaves (Example 4), as well as stable expression in monocotyledonous sugar cane callus (Example 7), monocotyledonous rice callus (Example 8), and dicotyledonous tobacco leaves (Example 9).

The present invention is not limited to SEQ ID NO:7 but specifically contemplates portions thereof. As used herein the term "portion" when made in reference to a nucleic acid sequence refers to a fragment of that sequence. The fragment may range in size from ten (10) contiguous nucleotide residues to the entire nucleic acid sequence minus one nucleic acid residue. Thus, a nucleic acid sequence comprising "at least a portion of" a nucleotide sequence comprises from ten (10) contiguous nucleotide residues of the nucleotide sequence to the entire nucleotide sequence.

In a preferred embodiment, portions contemplated to be within the scope of the invention include, but are not limited to, portions larger than 20 nucleotide bases, more preferably larger than 100 nucleotide bases, the sequence upstream of the 5' UTR sequence (i.e., nucleotide sequence from position 1 to 377 of SEQ ID NO:7), the 5' UTR sequence (i.e., nucleotides sequence from position 378 to 442 of SEQ ID NO:7 ), and the intron sequence (i.e., nucleotide sequence from position 443 to 1802 of SEQ ID NO:7). In an alternative preferred embodiment, portions within the scope of the invention include portions larger than 20 nucleotide bases, more preferably larger than 100 nucleotide bases, those sequences which are upstream of the translation start codon and which are identical in the initially determined and subsequently determined sequence of the ubi4 gene, and are exemplified by the nucleotide sequence from position 1 to 242, from position 245 to 787, from position 788 to 1020, from position 1021 to 1084, from position 1085 to 1168, from position 1169 to 1173, from position 1174 to 1648, and from position 1649 to 1802 of SEQ ID NO:7. In yet another alternative preferred embodiment, the portion contains the 377 bp sequence which is upstream of the 5' UTR and which is highly homologous (>90% identity) in both the ubi4 and ubi9 gene sequences, i.e., the nucleotide sequence from position 1 to 377 of SEQ ID NO:7.

It is contemplated that the present invention is not limited to SEQ ID NO: 10 but specifically includes portions thereof. In a preferred embodiment, portions contemplated to be within the scope of the invention include, but are not limited to, portions larger than 20 nucleotide bases, more preferably larger than 100 nucleotide bases, the sequence upstream of the 5' UTR sequence (i.e., nucleotide sequence from position 1 to 2248 of SEQ ID NO:10), the 5' UTR sequence (i.e., nucleotides sequence from position 2249 to 2313 of SEQ ID NO:10), and the intron sequence (i.e., nucleotide sequence from position 2314 to 3688 of SEQ ID NO:10). In an alternative preferred embodiment, portions within the scope of the invention include portions larger than 20 nucleotide bases, more preferably larger than 100 nucleotide bases, those sequences which are upstream of the translation start codon and which are identical in the initially determined and subsequently determined sequence of the ubi9 gene, and are exemplified by the nucleotide sequence from position 1 to 3600, from position 3602 to 3612, and from position 3614 to 3688 of SEQ ID NO:10. In yet another alternative preferred embodiment, the portion contains the sequence which is upstream of the transcription start codon and which is highly homologous (>90% identity) in both the ubi4 and ubi9 gene sequences, i.e., the nucleotide sequence from position 1671 to 2248 of SEQ ID NO:10. This sequence includes the MITE (from position 1706 to 1906) which is not homologous to sequences in the polyubiquitin ubi4 promoter.

The sequences of the present invention are not limited to SEQ ID NOs:7 and 10 and portions thereof, but also include homologs of SEQ ID NOs:7 and 10, as well as portions of these homologs. A nucleotide sequence which is a "homolog" of SEQ ID NOs:7 and 10 is defined herein as a nucleotide sequence which exhibits greater than 61% identity (but not 100% identity) to the sequence of SEQ ID NOs:7 and 10, respectively.

The present invention also contemplates functioning or functional homologs of SEQ ID NOs:7 and 10. A "functional homolog" of SEQ ID NOs:7 and 10 is defined as a nucleotide sequence which can hybridize to SEQ ID NOs:7 and 10, respectively, under conditions of low stringency (as described supra), preferably having less than 100% homology, more preferably greater than 60%, yet more preferably greater than 75%, and still more preferably greater than 85% homology, with SEQ ID NOs:7 and 10, respectively, and which has promoter activity having some or all the characteristics (e.g., constitutive promoter activity) of the promoter activity of SEQ ID NOs:7 and 10, respectively. Homologs of SEQ ID NOs:7 and 10, and of portions thereof, include, but are not limited to, nucleotide sequences having deletions, insertions or substitutions of different nucleotides or nucleotide analogs as compared to SEQ ID NOs:7 and 10, respectively. Such homologs may be produced using methods well known in the art.

The invention also contemplates at least a portion of SEQ ID NOs:7 and 10, and homologs thereof having promoter activity. The term "promoter activity" when made in reference to a nucleic acid sequence refers to the ability of the nucleic acid sequence to initiate transcription of an operably linked nucleotide sequence into mRNA. The terms "operably linked," "in operable combination," and "in operable order" as used herein refer to the linkage of nucleic acid sequences in a manner such that a nucleic acid molecule is capable of directing the transcription of nucleic acid sequence of interest and/or the synthesis of a polypeptide sequence of interest.

Promoter activity may be determined using methods known in the art. For example, a candidate nucleotide sequence whose promoter activity is to be determined is ligated in-frame to a nucleic acid sequence of interest (e.g., a reporter gene sequence, a selectable marker gene sequence) to generate a reporter vector, introducing the reporter vector into plant tissue using methods described herein, and detecting the expression of the reporter gene (e.g., detecting the presence of encoded mRNA or encoded protein, or the activity of a protein encoded by the reporter gene). The reporter gene may express a visible markers. Reporter gene systems which express visible markers include β-glucuronidase and its substrate (X-Gluc), luciferase and its substrate (luciferin), and β-galactosidase and its substrate (X-Gal) which are widely used not only to identify transformants, but also to quantify the amount of transient or stable protein expression attributable to a specific vector system [Rhodes C A et al. (1995) Methods Mol Biol 55:121–131]. In a preferred embodiment, the reporter gene is a GUS gene. The selectable marker gene may confer antibiotic or herbicide resistance. Examples of reporter genes include, but are not limited to, dhfr which confers resistance to methotrexate [Wigler M et al., (1980) Proc Natl Acad Sci 77:3567–70]; npt, which confers resistance to the aminoglycosides neomycin and G-418 [Colbere-Garapin F et al., (1981) J. Mol. Biol. 150:1–14] and als or pat, which confer resistance to chlorsulfuron and phosphinotricin acetyl transferase, respectively. Detecting the presence of encoded mRNA or encoded protein, or the activity of a protein encoded by the reporter gene or the selectable marker gene indicates that the candidate nucleotide sequence has promoter activity.

Sequences within a promoter which affect promoter activity may be determined by using deletion constructs such as those described by Sherri et al. for the determination of HSP70 intron alterations which impact transcription of genes operably linked thereto [U.S. Pat. No. 5,593,874, hereby incorporated by reference]. Briefly, several expression plasmids are constructed to contain a reporter gene under the regulatory control of different candidate nucleotide sequences which are obtained either by restriction enzyme deletion of internal sequences in SEQ ID NOs:7 and 10, restriction enzyme truncation of sequences at the 5' and/or 3' end of SEQ ID NOs:7 and 10, or by the introduction of single nucleic acid base changes by PCR into SEQ ID NOs:7 and 10. Expression of the reporter gene by the deletion constructs is detected. Detection of expression of the reporter gene in a given deletion construct indicates that the candidate nucleotide sequence in that deletion construct has promoter activity.

At the 3' end of the nucleic acid sequence of interest, other DNA sequences may also be included, e.g., a 3' untranslated region containing a polyadenylation site and transcription termination sites.

The present invention is not limited to sense molecules of SEQ ID NOs:7 and 10 but contemplates within its scope antisense molecules comprising a nucleic acid sequence complementary to at least a portion (e.g., a portion greater than 100 nucletide bases in length and more preferably greater than 200 nucleotide bases in length) of the nucleotide sequence of SEQ ID NOs:7 and 10. These antisense molecules find use in, for example, reducing or preventing expression of a gene whose expression is controlled by SEQ ID NOs:7 and 10.

The nucleotide sequence of SEQ ID NOs:7 and 10, portions, homologs and antisense sequences thereof may be synthesized by synthetic chemistry techniques which are commercially available and well known in the art [see Caruthers M H et al., (1980) Nuc. Acids Res. Symp. Ser. 215–223; Horn T. et al., (1980) Nuc. Acids Res. Symp. Ser. 225–232]. Additionally, fragments of SEQ ID NOs:7 and 10 can be made by treatment of SEQ ID NOs:7 and 10 with restriction enzymes followed by purification of the fragments by gel electrophoresis. Alternatively, sequences may also produced using the polymerase chain reaction (PCR) as described by Mullis [U.S. Pat. Nos. 4,683,195, 4,683,202 and 4,965,188, all of which are hereby incorporated by reference]. SEQ ID NOs:7 and 10, portions, homologs and antisense sequences thereof may be ligated to each other or to heterologous nucleic acid sequences using methods well known in the art.

The nucleotide sequence of synthesized sequences may be confirmed using commercially available kits as well as using methods well known in the art which utilize enzymes such as the Klenow fragment of DNA polymerase I, Sequenase®, Taq DNA polymerase, or thermostable T7 polymerase. Capillary electrophoresis may also be used to analyze the size and confirm the nucleotide sequence of the products of nucleic acid synthesis, restriction enzyme digestion or PCR amplification.

It is readily appreciated by those in the art that the sequences of the present invention may be used in a variety of ways. For example, these sequences are useful in directing the expression of polypeptide sequences in vitro and in vivo. In plants, this is useful in determining the role of the polypeptide in disease development as well an in producing transgenic plants with desirable agronomic characteristics as described below. In addition, portions of the sequences of the invention can be used as probes for the detection and isolation of complementary DNA sequences, and for the amplification of nucleotide sequences as described below.

B. Using Probes to Identify and Isolate Homologs of the Sugarcane Promoter Sequences The invention provided herein is not limited to SEQ ID NO:7 and 10, homologs thereof, and portions thereof, having promoter activity, but includes sequences having no promoter activity (i.e., non-functional homologs and non-functional portions of homologs). This may be desirable, for example, where a portion of SEQ ID NOs:7 and 10 is used as a probe to detect the presence of SEQ ID NOs:7 and 10, respectively, or of portions thereof in a sample.

As used herein, the term "probe" refers to an oligonucleotide, whether occurring naturally as in a purified restriction digest or produced synthetically, recombinantly or by PCR amplification, which is capable of hybridizing to a nucleotide sequence of interest. A probe may be single-stranded or double-stranded. It is contemplated that any probe used in the present invention will be labelled with any "reporter molecule," so that it is detectable in any detection system including, but not limited to enzyme (e.g., ELISA, as well as enzyme-based histochemical assays), fluorescent, radioactive, calorimetric, gravimetric, magnetic, and luminescent systems. It is not intended that the present invention be limited to any particular detection system or label.

The probes provided herein are useful in the detection, identification and isolation of, for example, sequences such as those listed as SEQ ID NOs:7 and 10 as well as of homologs thereof. Preferred probes are of sufficient length (e.g., from about 9 nucleotides to about 20 nucleotides or more in length) such that high stringency hybridization may be employed. In one embodiment, probes from 20 to 50 nucleotide bases in length are employed.

C. Using Primers to Amplify Nucleotide Sequences

The invention provided herein is not limited to SEQ ID NO:7 and 10, homologs thereof, and portions thereof, having promoter activity, but includes sequences having no promoter activity. This may be desirable, for example, where a portion of the nucleic acid sequences set forth as SEQ ID NOs:7 and 10 is used as a primer for the amplification of nucleic acid sequences by, for example, polymerase chain reactions (PCR) or reverse transcription-polymerase chain reactions (RT-PCR). The term "amplification" is defined as the production of additional copies of a nucleic acid sequence and is generally carried out using polymerase chain reaction technologies well known in the art [Dieffenbach C W and G S Dveksler (1995) PCR *Primer, a Laboratory Manual*, Cold Spring Harbor Press, Plainview N.Y.]. As used herein, the term "polymerase chain reaction" ("PCR") refers to the method of K. B. Mullis disclosed in U.S. Pat. Nos. 4,683,195, 4,683,202 and 4,965,188, all of which are hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are the to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; and/or incorporation of $^{32}$P-labeled deoxyribonucleotide triphosphates, such as dCTP or dATP, into the amplified segment). In addition to genomic DNA, any nucleotide sequence can be amplified with the appropriate set of primer molecules. In particular, the amplified segments created by the PCR process itself are, themselves, efficient templates for subsequent PCR amplifications. Amplified target sequences may be used to obtain segments of DNA (e.g., genes) for the construction of targeting vectors, transgenes, etc.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long (e.g., from about 9 nucleotides to about 20 nucleotides or more in length) to prime the synthesis of extension products in the presence of the inducing agent. Suitable lengths of the primers may be empirically determined and depend on factors such as temperature, source of primer and the use of the method. In one embodiment, the present invention employs probes from 20 to 50 nucleotide bases in length.

The primers contemplated by the invention are useful in, for example, identifying sequences which are homologous to the sugarcane ubi4 and ubi9 gene sequences in plants and in other organisms.

D. Generating Transgenic Plants

The present invention provides methods for constitutively expressing a nucleotide sequence of interest in a cell, tissue, organ, and/or organism. In one embodiment, the methods provided herein direct constitutive expression of a nucleotide sequence of interest in monocotyledonous and dicotyledonous plant cells. In one embodiment, this is accomplished by introducing into a plant cell a vector that contains a nucleotide sequence of interest operably linked to sequences provided herein which have promoter activity. The transformed plant cell is allowed to develop into a transgenic plant in which the nucleotide sequence of interest is preferably, though not necessarily, expressed in substantially every tissue. These steps are further described below for specific embodiments.

1. Expression Vectors for Plants

In one embodiment, the methods of the invention involve transformation of monocotyledonous tissue (sugarcane suspension cultured cells, sugarcane callus, rice callus, maize embryos, pineapple leaves, protocorm-like bodies, roots and fruit, and sorghum callus) and dicotyledonous tissue (tobacco leaves, tomato plants, and soybean excised embryonic meristems) with expression vectors in which the β-glucuronidase (GUS) gene is under the transcriptional control of the exemplary sugarcane ubi4 gene promoter sequence (SEQ ID NO:7) or of the exemplary sugarcane ubi9 gene promoter sequence (SEQ ID NO:10). As used herein, the terms "vector" and "vehicle" are used interchangeably in reference to nucleic acid molecules that transfer DNA segment(s) from one cell to another. The term "expression vector" as used herein refers to a recombinant DNA molecule containing a desired coding sequence and appropriate nucleic acid sequences necessary for the expression of the operably linked coding sequence in a particular host organism.

The methods of the invention are not limited to the expression vectors disclosed herein. Any expression vector which is capable of introducing a nucleic acid sequence of interest into a plant cell is contemplated to be within the scope of this invention. Typically, expression vectors comprise the nucleic acid sequence of interest as well as companion sequences which allow the transcription of this sequence, and which allow cloning of the vector into a bacterial or phage host. The vector preferably, though not necessarily, contains an origin of replication which is functional in a broad range of prokaryotic hosts. A selectable marker is generally, but not necessarily, included to allow selection of cells bearing the desired vector.

In a preferred embodiment, the promoter sequence is SEQ ID NO:7 which is derived from the sugarcane ubi4 gene. In an alternative preferred embodiment, the promoter sequence is SEQ ID NO:10 which is derived from the sugarcane ubi9 gene. However, the invention is not limited to the promoter sequences used herein. Any sequence which is a portion, homolog, or a homolog of a portion of SEQ ID NOs:7 and 10 and which has promoter activity is contemplated to be within the scope of the invention.

In addition to a promoter sequence, the expression vector preferably contains a transcription termination sequence downstream of the nucleic acid sequence of interest to provide for efficient termination. Exemplary termination sequences include the nopaline synthase (NOS) termination sequence, and different fragments of the sugarcane ribulose-1,5-biphosphate carboxylase/oxygenase (rubisco) small subunit (scrbcs) gene. The termination sequences of the expression vectors are not critical to the invention. The termination sequence may be obtained from the same gene as the promoter sequence or may be obtained from different genes.

If the mRNA encoded by the nucleic acid sequence of interest is to be efficiently translated, polyadenylation sequences are also commonly added to the expression vector. Examples of the polyadenylation sequences include, but are not limited to, the Agrobacterium octopine synthase signal, or the nopaline synthase signal. Where it is preferred that the nucleic acid sequence of interest is not translated into a polypeptide (e.g., where the nucleic acid sequence of interest encodes an antisense RNA), polyadenylation signals are not necessary.

Vectors for the transformation of plant cells are not limited to the type or nature of the expressed genes disclosed herein. Any nucleic acid sequence of interest may be used to create transgenic plant cells, tissues, organs, and plants. Nucleic acid sequences of interest include sequences which encode a protein of interest. The terms "protein of interest" and "polypeptide of interest" refer to any protein or polypeptide, respectively, the manipulation of which may be deemed desirable for any reason, by one of ordinary skill in the art.

For example, it may be desirable to express a nucleic acid sequence which encodes a polypeptide sequence having, for example, enzyme activity. One example of such an enzyme is the 1-aminocyclopropane-1-carboxylic acid (ACC) deaminase enzyme which metabolizes ACC in plant tissue thereby lowering the level of ethylene which is responsible for fruit ripening (U.S. Pat. No. 5,512,466, the contents of which are hereby incorporated by reference).

Another enzyme which may be desirably expressed in a plant is the sucrose phosphate synthase enzyme which increases the level of sucrose in the fruit. The nucleic acid sequence of the gene encoding this enzyme is known [e.g., in maize; Worrell et al. (1991) Plant Cell 3:1121–1130] (FIG. 15) (SEQ ID NO:12) and has been assigned GenBank accession number m97550.

Yet another example of a suitable enzyme for use in this invention is EPSP synthase (5-enolpyruvyl-3-phosphoshikimate synthase; EC:25.1.19) which is an enzyme involved in the shikimic acid pathway of plants. The shikimic acid pathway provides a precursor for the synthesis of aromatic amino acids essential to the plant. Specifically, EPSP synthase catalyzes the conversion of phosphoenol pyruvate and 3-phosphoshikimic acid to 5-enolpyruvyl-3-phosphoshikimate acid. A herbicide containing N-phosphonomethylglycine inhibits the EPSP synthase enzyme and thereby inhibits the shikimic acid pathway of the plant. The term "glyphosate" is usually used to refer to the N-phosphonomethylglycine herbicide in its acidic or anionic forms. Novel EPSP synthase enzymes have been discovered that exhibit an increased tolerance to glyphosate containing herbicides. In particular, an EPSP synthase enzyme having a single glycine to alanine substitution in the highly conserved region having the sequence: -L-G-N-A-G-T-A-(SEQ ID NO:17) located between positions 80 and 120 in the mature wild-type EPSP synthase amino add sequence has been shown to exhibit an increased tolerance to glyphosate and is described in U.S. Pat. No. 4,971,908, the teachings of which are hereby incorporated by reference. Methods for transforming plants to exhibit glyphosate tolerance are discussed in U.S. Pat. No. 4,940,835, incorporated herein by reference. A glyphosate-tolerant EPSP synthase plant gene encodes a polypeptide which contains a chloroplast transit peptide (CTP) which enables the EPSP synthase polypeptide (or an active portion thereto) to be transported into a chloroplast inside the plant cell. The EPSP synthase gene is transcribed into mRNA in the nucleus and the mRNA is translated into a precursor polypeptide (CTP/mature EPSP synthase) in the cytoplasm. The precursor polypeptide is transported into the chloroplast.

Additional examples of enzymes suitable for use in this invention are acetolactate synthase, RNase to impart male sterility [Mariani et al. (1990) Nature 347:737–741], and wheat germ agglutinin.

Yet other examples of desirable nucleic acid sequence are those which encode the sweetness protein. The nucleic acid sequence for the gene encoding the sweetness protein is known in the art (see, e.g., U.S. patent application Ser. No. 08/670,186, now U.S. Pat. No. 5,859,343 the contents of which are herein incorporated by reference). Transformation of plants with the sweetness protein is useful in, for example, providing a base level of sweetness in the fruit, thus reducing the effects of differences in fruit maturity by providing more uniform sweetness in different parts of the fruit.

Further examples of suitable proteins for use in this invention are *Bacillus thuringiensis* (B.t.) crystal toxin proteins which when expressed in plants protect the plants from insect infestation because the insect, upon eating the plant containing the B.t. toxin protein either dies or stops feeding. B.t. toxin proteins which are toxic to either Lepidopteran or Coleopteran insects may be used. Examples of particularly suitable DNA sequences encoding B.t. toxin protein are described in the EP patent application 385,962 entitled "Synthetic Plant Genes and Method for Preparation," published Sep. 5, 1990.

Alternatively, it may be desirable to express a nucleic acid sequence which encodes an antisense RNA that hybridizes with a genomic plant DNA sequence. For example, it may be of advantage to express antisense RNA which is specific for genomic plant DNA sequences that encode an enzyme whose activity is sought to be decreased. Examples of DNA sequences whose reduced expression may be desirable are known in the art including, but not limited to, the ethylene inducible sequences in fruit (U.S. Pat. No. 5,545,815, the entire contents of which are herein incorporated by reference). Expression of antisense RNA which is homologous with these ethylene inducible sequences is useful in delaying fruit ripening and in increasing fruit firmness. Other DNA sequences whose expression may be desirably reduced include the ACC synthase gene which encodes the ACC synthase enzyme that is the first and rate limiting step in ethylene biosynthesis. Nucleic acid sequences for this gene have been described from a number of plant sources (e.g., Picton et al. (1993) The Plant J. 3:469–481; U.S. Pat. Nos. 5,365,015 and 5,723,766, the contents of both of which are herein incorporated by reference). Expression of antisense RNA which hybridizes with ACC synthase genomic sequences in plants may be desirable to delay fruit ripening.

Yet another sequence whose expression may be advantageously reduced is the genomic sequence encoding the enzyme polyphenol oxidase. This enzyme is involved in the browning reaction that occurs during chilling injury. Nucleic acid sequences encoding this enzyme have been previously described in the art (e.g., Shahar et al. (1992) Plant Cell 4:135–147], as shown in FIG. 14 (SEQ ID NO:11) (GenBank accession number s40548). The use of antisense polyphenol antisense sequences has been reported to inhibit polyphenol oxidase (PPO) gene expression and to inhibit browning [Bachem et al. (1994) Bio/Technology 12:1101–1105].

One of skill in the art knows that the antisense DNA segment to be introduced into the plant may include the full length coding region of the targeted gene or a portion thereof. Complete homology between the nucleotide sequences of the antisense RNA and the targeted genomic DNA is not required. Rather, antisense DNA sequences which encode antisense RNA sequences that are partially homologous to a targeted genomic DNA sequence are contemplated to be within the scope of the invention so long as the antisense RNA sequences are capable of repressing expression of the target genomic DNA sequence.

The invention is not limited to vectors which express a single nucleic acid sequence of interest. Vectors which contain a plurality of (i.e., two or more) nucleic acid sequences under the transcriptional control of the same promoter sequence are expressly contemplated to be within the scope of the invention. Such vectors may be desirable, for example, where the expression products of the plurality of nucleic acid sequences contained within the vector provide protection against different pathogens, and where simultaneous protection against these different pathogens is deemed advantageous.

Also included within the scope of this invention are vectors which contain the same or different nucleic acid sequences under the transcriptional control of different promoter sequences derived from SEQ ID NO:7, SEQ ID NO:10, and other sequences. Such vectors may be desirable to, for example, to control different levels of expression of different nucleic acid sequences of interest in plant tissues.

2. Transformation of Plant Cells

Once an expression vector is prepared, transgenic plants and plant cells are obtained by introducing the expression vectors into plants and plant cells using methods known in the art. The present invention is suitable for any member of the monocotyledonous (monocot) plant family including, but not limited to, maize, rice, barley, oats, wheat, sorghum, rye, sugarcane, pineapple, yams, onion, banana, coconut, dates and hops. The present invention is also suitable for any member of the dicotyledonous (dicot) plant family including, but not limited to, tobacco, tomato, soybean, and papaya.

In one embodiment, the expression vectors are introduced into plant cells by particle mediated gene transfer. Particle mediated gene transfer methods are known in the art, are commercially available, and include, but are not limited to, the gas driven gene delivery instrument descried in McCabe, U.S. Pat. No. 5,584,807, the entire contents of which are herein incorporated by reference. This method involves coating the nucleic acid sequence of interest onto heavy metal particles, and accelerating the coated particles under the pressure of compressed gas for delivery to the target tissue.

Other particle bombardment methods are also available for the introduction of heterologous nucleic acid sequences into plant cells. Generally, these methods involve depositing the nucleic acid sequence of interest upon the surface of small, dense particles of a material such as gold, platinum, or tungsten. The coated particles are themselves then coated onto either a rigid surface, such as a metal plate, or onto a carrier sheet made of a fragile material such as mylar. The coated sheet is then accelerated toward the target biological tissue. The use of the flat sheet generates a uniform spread of accelerated particles which maximizes the number of cells receiving particles under uniform conditions, resulting in the introduction of the nucleic acid sample into the target tissue.

Alternatively, an expression vector may be inserted into the genome of plant cells by infecting the cells with a bacterium, including but not limited to an Agrobacterium strain previously transformed with the nucleic acid sequence of interest. Since most dicotyledonous plant are natural hosts for Agrobacterium, almost every dicotyledonous plant may be transformed by Agrobacterium in vitro. Although monocotyledonous plants, and in particular, cereals and grasses, are not natural hosts to Agrobacterium, work to transform them using Agrobacterium has also been carried out (Hooykas-Van Slogteren et al., (1984) Nature 311:763–764). Plant genera that may be transformed by Agrobacterium include Chrysanthemum, Dianthus, Gerbera, Euphorbia. Pelaronium, Ipomoea, Passiflora, Cyclamen, Malus, Prunus, Rosa, Rubus, Populus, Santalum, Allium, Lilium, Narcissus, Ananas, Arachis, Phaseolus and Pisum.

For transformation with Agrobacterium, disarmed Agrobacterium cells are transformed with recombinant Ti plasmids of *Agrobacterium tumefaciens* or Ri plasmids of *Agrobacterium rhizogenes* (such as those described in U.S. Pat. No. 4,940,838, the entire contents of which are herein incorporated by reference) which are constructed to contain the nucleic acid sequence of interest using methods well known in the art [J. Sambrook et al. (1989) *Molecular Cloning: A Laboratory Manual*, Cold Spring Harbor Press, NY]. The nucleic acid sequence of interest is then stably integrated into the plant genome by infection with the transformed Agrobacterium strain. For example, heterologous nucleic acid sequences have been introduced into plant tissues using the natural DNA transfer system of *Agrobacterium tumefaciens* and *Agrobacterium rhizogenes* bacteria (for review, see Klee et al. (1987) Ann. Rev. Plant Phys. 38:467–486).

Construction of recombinant Ti and Ri plasmids in general follows methods typically used with the more common bacterial vectors, such as pBR322. Additional use can be made of accessory genetic elements sometimes found with the native plasmids and sometimes constructed from foreign sequences. These may include but are not limited to structural genes for antibiotic resistance as selection genes.

There are two systems of recombinant Ti and Ri plasmid vector systems now in use. The first system is called the "cointegrate" system. In this system, the shuttle vector containing the gene of interest is inserted by genetic recombination into a non-oncogenic Ti plasmid that contains both the cis-acting and trans-acting elements required for plant transformation as, for example, in the pMLJ1 shuttle vector and the non-oncogenic Ti plasmid pGV3850. The second system is called the "binary" system in which two plasmids are used; the gene of interest is inserted into a shuttle vector containing the cis-acting elements required for plant transformation. The other necessary functions are provided in trans by the non-oncogenic Ti plasmid as exemplified by the pBIN19 shuttle vector and the non-oncogenic Ti plasmid PAL4404. Some of these vectors are commercially available.

There are three common methods to transform plant cells with Agrobacterium: The first method is by co-cultivation of Agrobacterium with cultured isolated protoplasts. This method requires an established culture system that allows culturing protoplasts and plant regeneration from cultured protoplasts. The second method is by transformation of cells or tissues with Agrobacterium. This method requires (a) that the plant cells or tissues can be transformed by Agrobacterium and (b) that the transformed cells or tissues can be induced to regenerate into whole plants. The third method is by transformation of seeds, apices or meristems with Agrobacterium. This method requires micropropagation.

One of skill in the art knows that the efficiency of transformation by Agrobacterium may be enhanced by using a number of methods known in the art. For example, the inclusion of a natural wound response molecule such as acetosyringone (AS) to the Agrobacterium culture has been shown to enhance transformation efficiency with *Agrobacterium tumefaciens* [Shahla et al. (1987) Plant Molec. Biol. 8:291–298]. Alternatively, transformation efficiency may be enhanced by wounding the target tissue to be transformed. Wounding of plant tissue may be achieved, for example, by punching, maceration, bombardment with microprojectiles, etc. [see, e.g., Bidney et al. (1992) Plant Molec. Biol. 18:301–313].

It may be desirable to target the nucleic acid sequence of interest to a particular locus on the plant genome. Site-directed integration of the nucleic acid sequence of interest into the plant cell genome may be achieved by, for example, homologous recombination using Agrobacterium-derived sequences. Generally, plant cells are incubated with a strain of Agrobacterium which contains a targeting vector in which sequences that are homologous to a DNA sequence inside the target locus are flanked by Agrobacterium transfer-DNA (T-DNA) sequences, as previously described (Offringa et al., (1996), U.S. Pat. No. 5,501,967, the entire contents of which are herein incorporated by reference). One of skill in the art knows that homologous recombination may be achieved using targeting vectors which contain sequences that are homologous to any part of the targeted plant gene, whether belonging to the regulatory elements of the gene, or the coding regions of the gene. Homologous recombination may be achieved at any region of a plant gene so long as the nucleic acid sequence of regions flanking the site to be targeted is known.

Where homologous recombination is desired, the targeting vector used may be of the replacement- or insertion-type (Offringa et al. (1996), supra). Replacement-type vectors generally contain two regions which are homologous with the targeted genomic sequence and which flank a heterologous nucleic acid sequence, e.g., a selectable marker gene sequence. Replacement-type vectors result in the insertion of the selectable marker gene which thereby disrupts the targeted gene. Insertion-type vectors contain a single region of homology with the targeted gene and result in the insertion of the entire targeting vector into the targeted gene.

Other methods are also available for the introduction of expression vectors into plant tissue, e.g., electroinjection (Nan et al. (1995) In "Biotechnology in Agriculture and Forestry," Ed. Y. P. S. Bajaj, Springer-Verlag Berlin Heidelberg, Vol 34:145–155; Griesbach (1992) HortScience 27:620); fusion with liposomes, lysosomes, cells, minicells or other fusible lipid-surfaced bodies (Fraley et al. (1982) Proc. Natl. Acad. Sci. USA 79:1859–1863); polyethylene glycol (Krens et al. (1982) nature 296:72–74); chemicals that increase free DNA uptake; transformation using virus, and the like.

3. Selection of Transgenic Plant Cells

Plants, plant cells and tissues transformed with a heterologous nucleic acid sequence of interest are readily detected using methods known in the art including, but not limited to, restriction mapping of the genomic DNA, PCR-analysis, DNA-DNA hybridization, DNA-RNA hybridization, DNA sequence analysis and the like.

Additionally, selection of transformed plant cells may be accomplished using a selection marker gene. It is preferred, though not necessary, that a selection marker gene be used to select transformed plant cells. A selection marker gene may confer positive or negative selection.

A positive selection marker gene may be used in constructs for random integration and site-directed integration. Positive selection marker genes include antibiotic resistance genes, and herbicide resistance genes and the like. In one embodiment, the positive selection marker gene is the NPTII gene which confers resistance to geneticin (G418) or kanamycin. In another embodiment the positive selection marker gene is the HPT gene which confers resistance to hygromycin. The choice of the positive selection marker gene is not critical to the invention as long as it encodes a functional polypeptide product. Positive selection genes known in the art include, but are not limited to, the ALS gene (chlorsulphuron resistance), and the DHFR-gene (methothrexate resistance).

A negative selection marker gene may also be included in the constructs. The use of one or more negative selection marker genes in combination with a positive selection marker gene is preferred in constructs used for homologous recombination. Negative selection marker genes are generally placed outside the regions involved in the homologous recombination event. The negative selection marker gene serves to provide a disadvantage (preferably lethality) to cells that have integrated these genes into their genome in an expressible manner. Cells in which the targeting vectors for homologous recombination are randomly integrated in the genome will be harmed or killed due to the presence of the negative selection marker gene. Where a positive selection marker gene is included in the construct, only those cells having the positive selection marker gene integrated in their genome will survive.

The choice of the negative selection marker gene is not critical to the invention as long as it encodes a functional polypeptide in the transformed plant cell. The negative selection gene may for instance be chosen from the aux-2 gene from the 5Ti-plasmid of Agrobacterium, the tk-gene from SV40, cytochrome P450 from *Streptomyces griseolus*, the Adh-gene from Maize or Arabidopsis, etc. Any gene encoding an enzyme capable of converting a substance which is otherwise harmless to plant cells into a substance which is harmful to plant cells may be used.

4. Regeneration of Transgenic Plants

The present invention provides transgenic plants. The transgenic plants of the invention are not limited to plants in which each and every cell expresses the nucleic acid sequence of interest under the control of the sequences provided herein. Included within the scope of this invention is any plant which contains at least one cell which expresses the nucleic acid sequence of interest (e.g., chimeric plants). It is preferred, though not necessary, that the transgenic plant express the nucleic acid sequence of interest in more than one cell, and more preferably in one or more tissue.

Once transgenic plant tissue which contains an expression vector has been obtained, transgenic plants may be regenerated from this transgenic plant tissue using methods known in the art. The term "regeneration" as used herein, means growing a whole plant from a plant cell, a group of plant cells, a plant part or a plant piece (e.g., from a protoplast, callus, protocorm-like body, or tissue part).

Species from the following examples of genera of plants may be regenerated from transformed protoplasts: Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Hyoscyamus, Lycopersicon, Nicotiana, Solanum, Petunia, Digitalis, Majorana, Ciohorium, Helianthus, Lactuca, Bromus, Asparagus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum, and Datura.

For regeneration of transgenic plants from transgenic protoplasts, a suspension of transformed protoplasts or a petri plate containing transformed explants is first provided. Callus tissue is formed and shoots may be induced from callus and subsequently rooted. Alternatively, somatic embryo formation can be induced in the callus tissue. These somatic embryos germinate as natural embryos to form plants. The culture media will generally contain various amino acids and plant hormones, such as auxin and cytokinins. It is also advantageous to add glutamic acid and proline to the medium, especially for such species as corn and alfalfa. Efficient regeneration will depend on the medium, on the genotype, and on the history of the culture. These three variables may be empirically controlled to result in reproducible regeneration.

Plants may also be regenerated from cultured cells or tissues. Dicotyledonous plants which have been shown capable of regeneration from transformed individual cells to obtain transgenic whole plants include, for example, apple (*Malus pumila*), blackberry (Rubus), Blackberry/raspberry hybrid (Rubus), red raspberry (Rubus), carrot (*Daucus carota*), cauliflower (*Brassica oleracea*), celery (*Apium graveolens*), cucumber (*Cucumis sativus*), eggplant (*Solanum melongena*), lettuce (*Lactuca sativa*), potato (*Solanum tuberosum*), rape (*Brassica napus*), wild soybean (*Glycine canescens*), strawberry (*Fragaria x ananassa*), tomato (*Lycopersicon esculentum*), walnut (*Juglans regia*), melon (*Cucumis melo*), grape (*Vitis vinifera*), and mango (*Mangifera indica*). Monocotyledonous plants which have been shown capable of regeneration from transformed individual cells to obtain transgenic whole plants include, for example, rice (*Oryza sativa*), rye (*Secale cereale*), and maize.

In addition, regeneration of whole plants from cells (not necessarily transformed) has also been observed in: apricot (*Prunus armeniaca*), asparagus (*Asparagus officinalis*), banana (*hybrid Musa*), bean (*Phaseolus vulgaris*), cherry (*hybrid Prunus*), grape (*Vitis vinifera*), mango (*Mangifera indica*), melon (*Cucurnis melo*), ochra (*Abelmoschus esculentus*), onion (*hybrid Allium*), orange (*Citrus sinensis*), papaya (*Carrica papaya*), peach (*Prunus persica*), plum (*Prunus domestica*), pear (*Pyrus communis*), pineapple (*Ananas comosus*), watermelon (*Citrullus vulgaris*), and wheat (*Triticum aestivum*).

The regenerated plants are transferred to standard soil conditions and cultivated in a conventional manner. After the expression vector is stably incorporated into regenerated transgenic plants, it can be transferred to other plants by vegetative propagation or by sexual crossing. For example, in vegetatively propagated crops, the mature transgenic plants are propagated by the taking of cuttings or by tissue culture techniques to produce multiple identical plants. In seed propagated crops, the mature transgenic plants are self crossed to produce a homozygous inbred plant which is capable of passing the transgene to its progeny by Mendelian inheritance. The inbred plant produces seed containing the nucleic acid sequence of interest. These seeds can be grown to produce plants that would produce the selected phenotype. The inbred plants can also be used to develop new hybrids by crossing the inbred plant with another inbred plant to produce a hybrid.

Confirmation of the transgenic nature of the cells, tissues, and plants may be performed by PCR analysis, antibiotic or herbicide resistance, enzymatic analysis and/or Southern blots to verify transformation. Progeny of the regenerated plants may be obtained and analyzed to verify whether the transgenes are heritable. Heritability of the transgene is further confirmation of the stable transformation of the transgene in the plant.

EXPERIMENTAL

The following examples serve to illustrate certain preferred embodiments and aspects of the present invention and are not to be construed as limiting the scope thereof.

EXAMPLE 1

Isolation and Characterization of Sugarcane Polyubiquitin ubi4 And ubi9 Genes

A. Plant Materials

The plant materials used for the cDNA library and for expression studies were sugarcane hybrid H65-7052 plants grown in the greenhouse of the Hawaii Agriculture Research Center, Aiea, Ha. The genomic library used to isolate the genomic clones was made from the related sugarcane hybrid H32-8560 [Albert et al., Plant Mol Biol 20, 663–71 (1992)]. Internodes were numbered consecutively down the culm, with number one defined as that internode subtending the youngest fully expanded leaf, as previously described [Moore P. H.: Anatomy and Morphology. In: Heinz D J (ed) Sugarcane Improvement Through Breeding, pp. 85–142. Elsevier, Amsterdam (1987)].

Sequence comparisons of the 3' untranslated regions (UTR) of five polyubiquitin cDNA clones revealed significant differences, except for clones scubi241 and 511, which were identical in both 5' and 3' UTR sequences. Despite these identical regions, these clones do not represent transcripts from the same gene, as scubi241 contained four copies of the polyubiquitin coding repeat, whereas scubi511 contained five of these repeats (data not shown).

B. Plasmid DNA Gel Blots

Polyubiquitin cDNA plasmid clones were digested with appropriate restriction enzymes and size fractionated by gel electrophoresis. DNA was transferred to Hybond-N+ (Amersham) membranes by capillary transfer. Identical DNA gel blots of the five clones were hybridized to 3' UTR probes at high stringency. High stringency hybridization and stringency washes at 65° C. were by the method of [Church et al., Proc. Natl. Acad. Sci. USA 81, 1991–1995 (1984)]. Probe templates were prepared by PCR amplification of the 3' UTR of each cDNA clone. Probes were $^{32}$P labeled by the method of [Feinberg et al., Anal. Biochem. 132, 6–13 (1983)]. Blots were exposed to Kodak X-Omat RP XRP-5 film for five to 10 min at room temperature.

C. RNA Extraction

Total RNA was extracted from 10 g of each tissue sample by the method of [Bugos et al., Biotechniques 19, 734–737 (1995)]. RNA concentration was determined by spectrophotometer. Poly-A+RNA was isolated from total RNA using the PolyATract System (Promega).

D. RNA Gel Blot Analysis

Fifteen μg of each RNA sample was separated by denaturing gel electrophoresis as described by [Foumey et al., Focus 10, 5–7 (1988)]. Hybridization and stringency washes at 65° C. were by the simplified northern blot method of [Virca et al., BioTechniques 8, 370–371 (1990)]. $^{32}$P incorporation into probes was monitored by two methods: scintillation counting following Sephadex G-50 chromatography and TCA precipitation. Equal activity ($1.7\times10^7$ cpm/ml) of $^{32}$P-labeled gene-specific probe was used for each hybridization. Autoradiography was with Kodak X-Omat RP XRP-5 film that was preflashed to an $OD_{540}$ of 0.15 to maximize linearity of response, exposed at −80° C.

Four identical RNA gel blots, each containing 15 μg total RNA from mature leaves, immature leaves, stem apices, internode 1, internode 2, internode 3, roots, and callus cultures at control (26° C.) and heat shock (37° C.) temperatures, were hybridized to each of the four gene specific 3' UTR probes, respectively, and exposed to film for 16 h as shown in FIG. 1.

In FIG. 1, 15 μg total RNA from each indicated tissue was hybridized to equal activities of each gene-specific probe. Ethidium bromide stained gel indicates equal loading of RNA from each tissue. M. L., mature leaves; I. L., immature leaves; S. A., shoot apex; I1, internode 1; I2, internode 2; I3, internode 3; R, roots; C, callus 26° C.; C-HS, callus 37° C. Autoradiogram for scubi221 probe was exposed for 72 h, all others for 16 h. With this exposure time of 16 h, transcripts homologous to scubi221 were not detected except in callus tissue under 37° C. heat-shock, where a single band was barely detectable. After 72 h exposure, the single band in heat-shock callus was clear, but no clear signal was evident for any other tissue. The scubi241/511 probe detected transcripts of two size classes (on the 16 h autoradiogram exposure shown in FIG. 1 the two bands overlap, however on shorter exposures two bands can be resolved), with both transcripts present in approximately equal amounts in all tested tissues. Transcripts for this sub-family were present at the highest levels of all tested polyubiquitin genes; heat shock at 37° C. did not induce a significant change in transcript accumulation. The scubi561 probe also detected two mRNA size classes; however, the levels of these transcripts were considerably lower than those detected with the 241/511 probe. Transcript pools hybridizing to the 561 probe were elevated significantly by 37° C. heat shock. The scubi5121 probe hybridized to a single size class that was moderately abundant, but significantly lower than the scubi241/511 pool. The 5121 levels were very similar in all tissues except callus. Callus at control temperature (26° C.) contained less scubi5121 mRNA than did other tissues; 37° C. heat shock elevated transcript levels in callus to levels approximately equal to those in other tissues at 26° C. This pattern of reduced transcript levels in control temperature callus tissue could be seen to some extent for all probes except scubi561.

To confirm the northern analysis results, a "reverse northern" blot containing the 3' UTR DNA of all five polyubiquitin cDNA clones was hybridized to a $^{32}$P-labeled, first strand cDNA probe made from approximately 0.5 μg mRNA extracted from immature leaves. Fifty ng of each 3' UTR target DNA was loaded for the blot, ensuring that the target DNA would be present in excess and that hybridization signals should reflect relative abundance of the different mRNAs in the template mRNA population. Results of this experiment are shown in FIG. 2.

Figure 2:
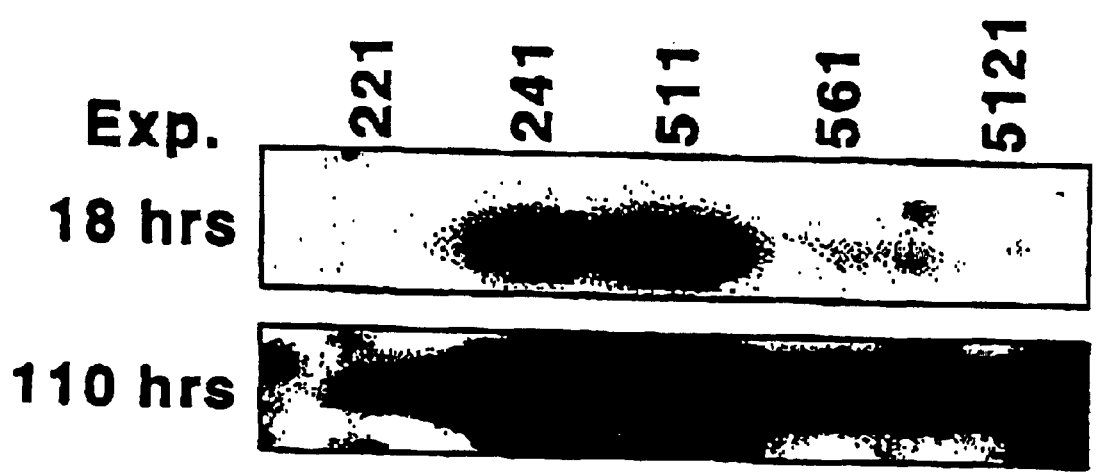
FIG. 2 shows a "Reverse northern" blot of sugarcane polyubiquitin mRNA pools.

In FIG. 2, 50 ng DNA from the gene-specific 3' UTR of each cDNA clone was hybridized to a total first strand cDNA probe from immature leaves. Results of this experiment confirmed the northern results, with scubi241/511 transcripts most abundant, scubi221 least abundant, and scubi561 and 5121 at intermediate levels (FIG. 2). Because these two independent methods of estimating the relative mRNA abundance for the different polyubiquitin gene sub-families both indicated the scubi241/511 sub-family as highest, and because the difference between scubi241/511 and the other sub-families was so large by both measures, this ranking of expression levels is accurate.

While expression of these sugarcane polyubiquitin genes was little affected by cell-type, several of them responded dramatically to an environmental stimulus: heat stress. mRNA pools homologous to scubi221, 561 and 5121 in sugarcane callus tissue subjected to 37° C. heat shock all rose substantially, whereas the pool homologous to scubi241/511 did not show a substantial increase. Overall, scubi241 and scubi511 most nearly fit the stereotype of "constitutive" genes, with uniformly high levels of mRNA accumulation in all tested tissues and little induction of expression by heat stress.

Approximately $1\times10^6$ pfu from a sugarcane genomic library in the vector λEMBL4 were screened with a polyubiquitin coding sequence probe. Fifty polyubiquitin positive plaques were screened again and purified with the scubi241/511 specific probe. Five scubi241/511 positive plaques were isolated, and two of these, λubi4 and kubi9, were subcloned into plasmid vectors for further analysis and sequencing.

Figure 4:
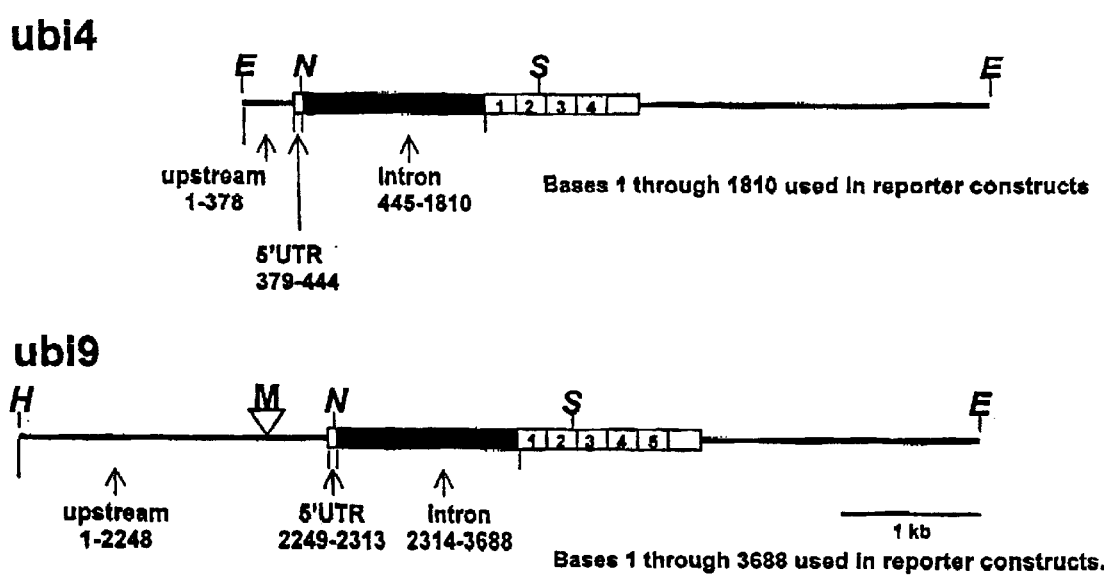
FIG. 4 is a diagrammatic representation of the initially-determined organization of ubi4 and ubi9 polyubiquitin genes. Numbered white boxes indicate polyubiquitin coding repeats, unnumbered white boxes are 5' and 3' untranslated regions, black boxes are introns, and lines are flanking DNA. E: EcoRI; N: NruI; S: SalI; H: HindIII; M: putative miniature inverted-repeat transposable element.

Subclone pubi4 sequence and organization were initially determined to be as shown in FIGS. 3A, 3B and 4. Tables 1–2 provide the meaning of sequence symbols other than the bases G, A, T, and C which indicates ambiguities where two or more bases are equally possible in the sequences shown in FIGS. 3A and 3B.

TABLE 1

Ambiguity codes for sugarcane polyubiquitin ubi4 gene sequences upstream of the translation start codon

| Position | Ambiguity Code Shown in FIG. 3A | Actual Base |
| --- | --- | --- |
| 243 | n | G, A, T, or C |
| 245 | n | G, A, T, or C |
| 790 | n | G, A, T, or C |
| 1023 | n | G, A, T, or C |
| 1089 | n | G, A, T, or C |
| 1174 | n | G, A, T, or C |
| 1656 | n | G, A, T, or C |

TABLE 2

Ambiguity codes for sugarcane polyubiquitin ubi4 gene downstream of the translation stop codon

| Position | Ambiguity Code Shown in FIG. 3B | Actual Base |
| --- | --- | --- |
| 17 | n | G, A, T, or C |
| 885 | n | G, A, T, or C |
| 1055 | s | C or G |
| 1059 | y | C or T |
| 1463 | n | G, A, T, or C |
| 1712 | n | G, A, T, or C |
| 1769 | r | A or G |
| 1810 | w | A or T |
| 1964 | y | C or T |
| 2495 | n | G, A, T, or C |

On subsequent sequencing of subclone pubi4, the nucleotide sequence (SEQ ID NO:5) and translated amino acid sequence (SEQ ID NO:6) were determined to be as shown in FIG. 5. The letter "X" in FIG. 5B refers to any amino acid. The organization of the ubi4 gene was determined as shown in FIG. 6.

SEQ ID NO:5 was cloned as two fragments into the plasmid vector pBluescript II KS+(Stratagene) to generate plasmids pubi4a and pubi4b. Plasmids pubi4a and pubi4b were introduced into the host *Escherichia coli* DH5alpha and the transformed *Escherichia coli* cells were deposited at the Agricultural Research Service Culture Collection (NRRL) under the terms of the Budapest Treaty on Mar. 8, 1999 as NRRLB-30112 (containing pubi4a) and NRRLB-30114 (containing pubi4b). NRRLB-30112 contains the 2227 bp EcoRI/SalI fragment of SEQ ID NO:5, i.e., including the 1802 bp 1802 bp SEQ ID NO:7, plus the first coding repeat and part of the second repeat. NRRLB-30114 contains the 3329 bp SalI/EcoRI fragment which includes the remainder of the coding region, the 3' UTR, and further downstream sequences.

An XbaI restriction site was added at the 3' end of the ubi4 promoter shown in SEQ ID NO:7 by way of PCR amplification with an XbaI adapter primer. The polyubiquitin ubi4 promoter so modified was ligated upstream of a GUS coding sequence and a NOS 3' terminator in the vector plasmid pUC19 to form pubi4-GUS. This plant expression plasmid was transformed into *E. coli* DH5a host cells and deposited with the NRRL under the terms of the Budapest Treaty on Mar. 15, 1999 as NRRLB-30115.

Table 3 shows the ambiguity codes and the bases they represent in the ubi4 sequences shown in FIGS. 5 and 10.

TABLE 3

Ambiguity codes for sugarcane polyubiquitin ubi4 and ubi9 genes

| Ambiguity Code | Actual Base |
| --- | --- |
| a | A |
| c | C |
| g | G |
| t/u | T |
| m | A or C |
| r | A or G |
| w | A or T |
| s | C or G |
| y | C or T |
| k | G or T |
| v | A or C or G |
| h | A or C or T |
| d | A or G or T |
| b | C or G or T |
| x/n | G or A or T or C |
| . | not G or A or T or C |

Subclone pubi4 (FIGS. 3, 4, 5 and 6) contained four copies of the polyubiquitin coding repeat, 238 bp of 3' UTR, which is approximately 95% identical to the corresponding region of the scubi241/511 cDNAs, a possible poly-A addition signal 215 bp 3' of the TAA stop codon, and approximately 2.6 kb of further downstream sequence. Immediately 5' of the initiation codon was an intron of 1360 bp within SEQ ID NO:5 (intron of 1382 bp within SEQ ID NO:1) which was preceded by 65 bp in SEQ ID NO:5 (67 bp in SEQ ID NO:1) that were 98% identical to the 5' UTR sequence of scubi241/5 11. The transcription start site has not yet been determined, and it is not known if the scubi241 and scubi511 cDNA clones contain the entire 5' UTR; however, since both scubi241 and scubi511 cDNA clones started at the same nucleotide, this site can serve as a putative transcription start site for discussion purposes. The pubi4 subclone contained an additional 377 bp upstream of the transcription start codon, with a TATA consensus at −30 bp relative to the beginning of the cDNAs. Approximately 320 bp upstream of the transcription start codon were two 10 bp sequences that showed homology to the heat stress promoter element (HSE) consensus sequence (aGAAnnTTCt) [Scharf et al.: Heat stress promoters and transcription factors. In: Nover L (ed) Plant Promoters and Transcription Factors, pp. 125–162. Springer-Verlag, Berlin (1994)]. The second of these 10 bp sequences, however, lacked the G residue at position two that has been found to be invariant in HSEs [Scharf et al. (1994) supra].

Subclone pubi9 sequence and organization were initially determined to be as shown in FIGS. 7A, 7B and 4. Tables 4–5 provide the meaning of sequence symbols other than the bases G, A, T, and C which indicates ambiguities where two or more bases are equally possible in the sequences shown in FIGS. 7A and 7B.

TABLE 4

Ambiguity codes for sugarcane polyubiquitin ubi9 gene upstream of the translation codon

| Position | Ambiguity Code Shown in FIG. 7A | Actual Base |
| --- | --- | --- |
| 9 | n | G, A, T, or C |
| 3613 | n | G, A, T, or C |

TABLE 5

Ambiguity codes for sugarcane polyubiquitin ubi9 gene downstream of the translation stop codon

| Position | Ambiguity Code Shown in FIG. 7B | Actual Base |
|---|---|---|
| 59 | n | G, A, T, or C |
| 286 | n | G, A, T, or C |
| 294 | n | G, A, T, or C |
| 319 | n | G, A, T, or C |

On subsequent sequencing of subclone pubi9, the nucleotide sequence (SEQ ID NO:8) and translated amino acid sequence (SEQ ID NO:9) were determined to be as shown in FIG. 8. The letter "X" in FIG. 8B refers to any amino acid. The organization of the ubi9 gene was determined as shown in FIG. 6. Table 3, supra, shows the ambiguity codes and the bases they represent in the ubi9 gene sequences shown in FIGS. 8 and 11.

An approximately 7.2 kb HindIII-EcoRI fragment, which contains SEQ ID NO:8 plus approximately 2kb additional downstream sequence, was cloned in the plasmid vector pBluescript II KS+(Stratagene) to form plasmid pubi9. This plasmid was transformed into E. coli DH5a host cells and deposited with the Agriculture Research Service culture collection (NRRL), under the terms of the Budapest Treaty on Mar. 8, 1999 as accession number NRRLB-30113.

An XbaI restriction site was added at the 3' end of the ubi9 promoter shown in SEQ ID NO:10 by way of PCR amplification with an XbaI adapter primer. The ubi9 promoter so modified was ligated upstream of a GUS coding sequence and a NOS 3' terminator in the vector plasmid pUC19 to form pubi9-GUS. This plant expression plasmid was transformed into E. coli DH5a host cells and deposited with the NRRL under the terms of the Budapest Treaty on Mar. 15, 1999 as accession number NRRLB-30116.

Subclone pubi9 (FIGS. 4, 6, 7 and 8) contained five copies of the polyubiquitin coding repeat, 244 bp of 3' UTR, which were 98% identical to the corresponding region of scubi241/511 and 95% identical to the corresponding region of pubi4. A possible poly-A addition signal was present 221 bp down stream of the TAA stop codon, and there was approximately 2 kb additional downstream sequence. As with the ubi4 gene, an intron was located immediately 5' of the initiation codon; this intron was 1374 bp. 5' of this intron were 65 bp (in SEQ ID NO:8) and 67 bp (in SEQ ID NO:3) that was 97% identical to both the 5' UTR of the scubi241/511 cDNA clones and the corresponding region of the ubi4 gene. The subclone contained an additional 2247 bp of upstream sequence, including a TATA consensus sequence at −30 bp relative to the beginning of the cDNA clones. Upstream of the 5' UTR, a 577 bp region of ubi9 from position 1671 to 2248 of SEQ ID NO:10 was highly homologous (>90% identity) to the corresponding region of ubi4 (positions 1 to 377 of SEQ ID NO:5). Partial sequence from an additional subclone of λubi4 indicated that this high degree of homology continues at least as far as 2 kb upstream of the transcribed region of the genes (unpublished data). Within this highly homologous region, approximately 344 bp upstream of transcription start codon, is an apparent insertion of approximately 200 bp not present in the sugarcane ubi4 promoter. This 200 bp region was delimited by 17 bp imperfect inverted repeats. A 202 bp region 82% identical to this insertion is also found in the 3' UTR of a sugarcane glucose transporter cDNA clone SGT1 [Bugos et al., Plant Physiol. 103, 1469–1470 (1993)]. The nature of this possible insertion event has not been investigated; however, it has features of miniature inverted-repeat transposable elements (MITEs) [Wessler et al., Curr Opin Genet Dev 5, 814–21 (1995)]. Without limiting the invention to any particular mechanism, this insertion is not believed to have a functional role in the promoter activity of the polyubiquitin ubi9 promoter since this insertion is inserted in the 3' UTR (not the promoter) of the glucose transporter gene, and since it is not present in the polyubiquitin ubi4 gene. Like the ubi4 gene, the ubi9 gene also contained two HSE-like sequences about 320 bp upstream of the transcription start codon; however, both of these HSE-like sequences lacked the invariant G residue.

A comparison of the sequences upstream of the translation start codon of the sugarcane ubi4 gene sequence with the maize polyubiquitin promoter (GenBank accession number S94464; Quail et al., U.S. Pat. Nos. 5,614,399 and 5,510,474) showed only 51% homology when comparing a fragment containing the sequence upstream of the 5' UTR; the 5' UTR sequence and the intron sequence, only 64% homology when comparing a fragment containing the sequence upstream of the transcription start codon, only 65% homology when comparing a fragment containing the 5' UTR sequence, and only 58% homology when comparing a fragment containing the intron sequence.

A comparison of the sequences upstream of the translation start codon of the sugarcane ubi9 gene sequence with the maize polyubiquitin promoter (GenBank accession number S94464; Quail et al., U.S. Pat. Nos. 5,614,399 and 5,510,474) showed only 61% homology when comparing a fragment containing the sequence upstream of the 5' UTR, the 5' UTR sequence and the intron sequence, only 63% homology when comparing a fragment containing the sequence upstream of the transcription start codon, only 66% homology when comparing a fragment containing the 5' UTR sequence, and only 59% homology when comparing a fragment containing the intron sequence.

Some heat-shock-inducible polyubiquitin promoters have been found to contain HSEs (Binet, et al., 1991, supra; Christensen et al. (1992) supra]. Both the ubi4 and ubi9 genes contained two short sequence elements that have some homology to HSEs; however, three out of four of these elements lacked the G residue that has been found to be invariant at position 2 of the HSE (aGAAnnTTCt) (Scharf et al. (1994) supra]. Given the very marginal induction (approximately 2-fold or less) of the ubi4 and ubi9 genes when compared to other sugarcane polyubiquitin genes, it is doubtful that these HSE-like elements play a role in regulating gene expression. Similar observations have been made in connection with the tobacco polyubiqutin promoter, Ubi.U4; while this promoter also contains " . . . two degenerated heat shock-like elements . . . , " removal of these elements had no significant effect on gene expression (Plesse, et al. (1997) supra].

Both the ubi4 and ubi9 genes contained a large intron immediately upstream of the protein coding region preceded by an approximately 65 bp fragment which was highly homologous to the 5' UTR of scubi241/511. An intron at this position (i.e., immediately upstream of the initiation codon) has been found in many other plant polyubiquitin genes (Binet, et al., 1991, supra; Christensen et al. (1992) supra; Garbarino et al. (1995) supra; Norris et al., Plant Mol Biol 21, 895–906 (1993)], and in some cases been shown important for high levels of expression (Norris et al. (1993) supra; Garbarino et al. (1995) supra]. By analogy, it is the inventors' belief that the intron of the ubi4 and ubi9 genes may also play a role in regulating gene expression.

The cDNA clones scubi241 and scubiS11 contain three and five copies of the polyubiquitin coding sequence, respectively. Genomic clones pubi4 and pubi9 contain four and five copies of the polyubiquitin coding sequence, respectively. Without limiting the invention to any particular mechanism, this may mean that the scubi241/511 sub-family contains at least three different genes, containing three (i.e., scubi 241/511), four (i.e., pubi4) and five (i.e., pubi9) ubiquitin repeats. Alternatively, it is possible that the difference in the number of copies of the polyubiquitin coding sequence reflects a difference between the cultivars, with the scubi241/511 sub-family in H65-7052 containing genes with three and five ubiquitin repeats, while the same sub-family in H32-8560 contains genes with four and five ubiquitin repeats.

EXAMPLE 2

Construction of Plasmids pubi4-GUS, pubi9-GUS, pCAM-ubi4-GUS, pCAM-ubi9-GUS, pCAM-Ubi-1-GUS, pBI-ubi4-GUS, pBI-ubi9-GUS, And pBI-Ubi-1-GUS Comprising Sugarcane Polyubiquitin Promoters And an Exemplary Structural Gene Reporter plasmids were made placing the uid A gene encoding β-glucuronidase (GUS) [Jefferson et al., Proc. Natl. Acad. Sci. USA 83, 8447–8451 (1986)] and the nopaline synthase (NOS) terminator under the control of the sugarcane polyubiquitin promoter disclosed herein. The promoter sequence in plasmid pubi4-GUS contained nucleotides 1–1810 of SEQ ID NO:1 (i.e., nucleotides 1–1802 of SEQ ID NO:5) and and XbaI site (TCTAGA) added immediately after bp 1802, by way of an adapter on a PCR primer. The promoter sequence in plasmid pubi9-GUS contained nucleotides 1–3688 of SEQ ID NO:3 (i.e., nucleotides 1–3688 of SEQ ID NO:8) and and XbaI site (TCTAGA) added immediately after bp 3688, by way of an adapter on a PCR primer. The Expand™ PCR system (Boehringer Mannheim) was used to amplify part of the 5' UTR and the intron including the 3' splice site; this PCR product was used to join the sequence upstream of the 5' UTR, the 5' UTR, and intron to the GUS gene using a unique NruI site in the 5' UTR and an XbaI site added as an adapter to the 3' PCR primer.

pHA9 contained the maize Ubi-1 promoter driving a neomycin phosphotransferase II (NPIII) gene and NOS terminator. It was made by removing the luc gene from pAHC18 described in [Christensen et al., Transgenic Research 5, 213–218 (1996)] as BamHI fragment and replacing it with an 844 bp BamHI fragment containing the NPTII gene.

pBI 121 contained the uid A gene encoding GUS under the control of the cauliflower mosaic virus (CaMV) 35S RNA promoter sequence (Clontech).

Binary plasmids pCAM-ubi4-GUS, pCAM-ubi9-GUS, pCAM-Ubi-1-GUS, pBI-ubi4-GUS, pBI-ubi9-GUS, and pBI-Ubi-1-GUS for Agrobacterium transformation were made by ligating the promoter-intron-GUS-NOS cassettes from pubi9-GUS, pubi4-GUS, and pAHC27 [Christensen et al. (1996) supra] respectively, as HindIII—EcoRI fragments, into the HindIII—EcoRI sites of pCAMBIA1300 [Roberts et al., Rockefeller Foundation Meeting of the International Program on Rice Biotechnology, Malacca, Malaysia (1997)]. Binary plasmid pCAM-5' M-ubi9-GUS-3' M contained a putative 5' nuclear matrix attachment region (MAR) from λubi4, ubi9 promoter and intron, GUS, and 3' terminator and putative 3' MAR from λubi4 as HindIII—EcoRI fragment in the HindIII—EcoRI sites of pCAMBIA1300.

Plasmids pCAM-ubi4-GUS, pCAM-ubi9-GUS, and pCAM-Ubi-1-GUS, were used for transformation of rice, while pBI-ubi4-GUS, pBI-ubi9-GUS, and pBI-Ubi-1-GUS and pBI121 (this construct contains 35S-GUS) were used to transfrom tobacco.

EXAMPLE 3

Transient Expression of pubi4-GUS and pubi9-GUS in Sugarcane Suspension Cultured Cells Sugarcane suspension cell cultures (variety H50-7209) were maintained as described by [Nickell et al., Physiol. Plant. 22, 117–125 (1969)]. DNA reporter plasmids (pubi4-GUS, pubi9-GUS,or pAHC27) were introduced into sugarcane suspension culture cells by particle bombardment as previously described [Klein et al., Nature 327, 70–73 (1987)] using a PDS1000 Biolistic particle accelerator (BioRad) at 1100 psi. Controls were not bombarded with DNA. Transient assays were carried out in a randomized complete block design with four treatments (promoters) and six replications. Each replication consisted of bombardment of five samples. Two days after bombardment, plant material was assayed for GUS expression. Each sample was divided into two equal parts, one for histochemical analysis and one for chemiluminescent measure of GUS enzyme activity using the GUS-Light kit (Tropix) and an MLX plate reader luminometer (DYNEX). GUS enzyme activity assays were performed according to the manufacturer's protocol, with 60 minutes incubation in GUS reaction buffer before chemiluminescence was measured. GUS activity was expressed as relative light units (RLU) per nanogram total protein [Bradford, Anal. Biochem. 72:248–254 (1976)]. From each experiment, the highest and lowest values were discarded for each plasmid. Analysis of variance was performed on the data from each set of experiments; those experiments which showed a significant effect ($P \leq 0.05$) from promoter treatments were further analyzed by a least significant difference test ($P \leq 0.05$) to identify which promoters produced significantly different results.

Figure 9:
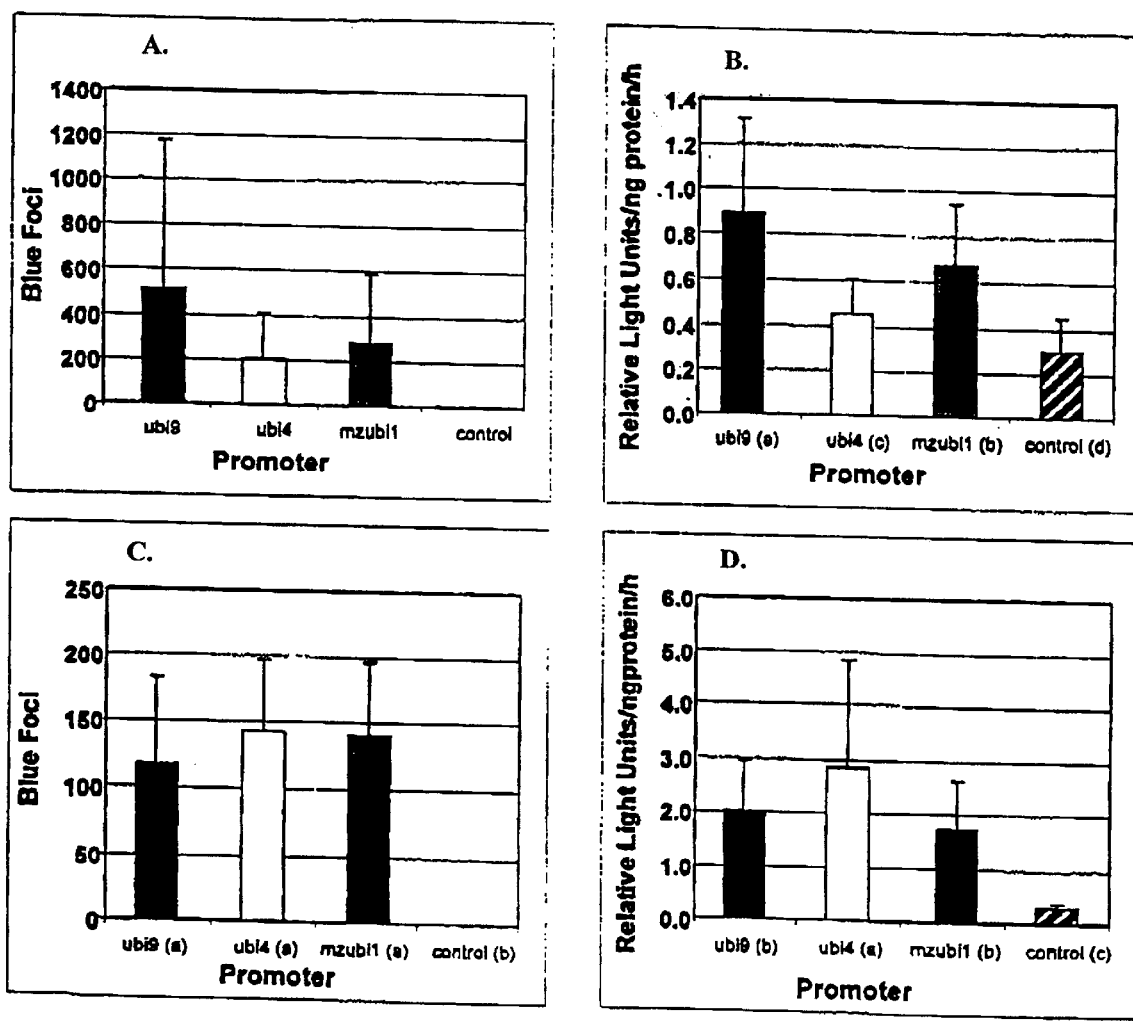
FIGS. 9(A–B) is a graph showing GUS activity following transient expression of GUS under the control of the sugarcane ubi4 promoter (ubi4), sugarcane ubi9 promoter (ubi9), and maize Ubi-1 promoter (mzubi1) in sugarcane suspension cells (A, B) and tobacco leaves (C, D). Controls received no DNA. Letters within parentheses indicate least significant difference levels, i.e., mean GUS activity values with different letters being significantly different at $P \leq 0.05$ confidence level.

The results of histochemical staining and chemiluminescent GUS activity assays of sugarcane suspension culture cells which had been bombarded with the reporter plasmids are shown in FIG. 9. FIG. 9A shows that the average number of blue foci detected after bombardment with GUS expression plasmids containing the ubi9 promoter was higher than observed for either the ubi4 or maize polyubiquitin Ubi-1 [Christensen et al. (1996), supra] promoters. Because of high levels of variability, it could not be determined from histochemical staining of these transient expression experiments whether the results seen in sugarcane callus are in fact significantly different. However, using a chemiluminescent assay to measure GUS activity again indicated the average level of expression was higher for the ubi9 promoter than for the sugarcane ubi4 or maize Ubi-1 promoters (FIG. 9B). Statistical analysis indicated that the difference, as measured by this assay, was significant at $P \leq 0.05$.

These data demonstrated that both the ubi4 and ubi9 promoters in pubi4-GUS and pubi9-GUS, respectively, were sufficient to direct transient expression in monocotyledonous sugarcane suspension cells.

EXAMPLE 4

Transient Expression of pubi4-GUS and pubi9-GUS in Tobacco Leaves

Tobacco cultivar Wisconsin 38 was grown in Magenta boxes on MSNT medium [1×Murashige and Skoog salts (GIBCO BRL #11117-074), 1×minimal organics (GIBCO BRL #11118-023), 30 g/l sucrose, 0.8% agar] at 26° C. under a 16 h light regime. DNA reporter plasmids (pubi4-GUS, pubi9-GUS, or pAHC27) were introduced into tobacco leaves by particle bombardment as previously described [Klein et al., (1987) supra] using a PDS1000 Biolistic particle accelerator (BioRad) at 650 psi. Controls were not bombarded with DNA. Transient assays were carried out in a randomized complete block design with four treatments (promoters) and six replications. Each replication consisted of bombardment of five samples. Two days after bombardment, plant material was assayed for GUS expression. Each sample was divided into two equal parts, one for histochemical analysis and one for chemiluminescent measure of GUS enzyme activity as described supra (Example 3).

The results of histochemical staining and chemiluminescent GUS activity assays of tobacco leaves which had been bombarded with the reporter plasmids are shown in FIG. 9. The results show that average GUS expression was higher for the sugarcane ubi4 promoter than for either the maize polyubiquitin promoter or the sugarcane ubi9 promoter when using either the histochemical (FIG. 9C) or chemiluminescent (FIG. 9D) assays. Analysis of the chemiluminescent data indicates that the difference between the sugarcane ubi4 and maize polyubiquitin promoters was statistically significant at $P \leq 0.05$.

These data demonstrated that both the ubi4 and ubi9 promoters in pubi4-GUS and pubi9-GUS, respectively, were sufficient to direct transient expression in dicotyledonous tobacco leaves.

EXAMPLE 5

Transient Expression of pubi4-GUS and pubi9-GUS in Sorghum Callus

Sorghum immature embryo derived callus was cultured and bombarded as previously described with the reporter plasmid ubi4-GUS or ubi9-GUS (prepared as described in Example 2) and with several reporter plasmids in which the uid A gene encoding GUS was placed under the control of each of several promoters including maize adh, 35S, 35S:35S, rice actin, and maize Ubi-1 as described below.
A. Culture Media N6 maintenance medium [Macro elements (mg/l final concentration), 2830 $KNO_3$, 1650 $(NH_4)_2SO_4$, 166 $CaCl_2$-$2H_2O$, 185 $MgSO_4$-$7H_2O$, 400 $KH_2PO_4$; Micro elements (mg/l final concentration), 37.3 $Na_2$ EDTA, 27.8 $FeSO_4$-$7H_2O$, 1.6 $H_3BO_3$ 0.76 KI, 3.3 $MnSO_4$, 1.5 $ZnSO_4$-$7H_2O$; Carbohydrates (g/l final concentration), 20 Sucrose; Hormones (mg/l final concentration), 1.0 2,4-Dichlorophenoxyacetic acid; Vitamins (mg/l final concentration), 0.5 Thiamine-HCl, 0.25 Pyridoxine-HCl, 0.25 Nicotinic Acid; Amino Acids (mg/l final concentration), 2875 L-Proline, 2.0 Glycine, 100 Casamino Acids; and Agar (g/l final concentration), 2.5 Phytagel] was used.
B. Plant Material Highly embryogenic callus tissue derived from sorghum plants (*Sorghum bicolor* L. Moench, cv BWheatland 399) was used. To establish callus cultures, caryopses 10 to 18 d post-anthesis were surface-sterilized with 70% ethanol for 5 min and 20% clorox bleach for 15 min, followed by two changes of sterile distilled water. Immature embryos, 1.0 to 1.5 mm long, were aseptically removed using a sterilized 11 cm forceps in a laminar flow hood under a stereo dissecting microscope. The embryos were placed with the scutella exposed on N6 medium modified for sorghum cell culture and solidified with 2.5 g/l Phytagel.
C. Microprojectile Bombardment Preparation Prior to bombardment, 1 mm gold particles were coated with transforming DNA by the procedure of Daines (1990). A stock suspension of gold particles was suspended at 60 mg/ml in absolute ethanol. Thirty-five microliters of the suspension was transferred into a 1.5 ml microcentrifuge tube, centrifuged at 14,000 g for 3 min, and the pellet was suspended in 200 µl of sterile distilled water. Following a second centrifugation, the pellet was suspended in 25 ml of Tris-EDTA containing 25 mg of the transforming plasmid DNA. The following chilled sterile solutions were added in order: 200 ml of water, 250 ml of 2.5 M $CaCl_2$, and 50 ml of 0.1 M Spermidine (0.2 µm filter-sterilized). The microcentrifuge tubes were shaken with a Tomy microtube shaker at 4° C. for 15 min and centrifuged at 16,000 g for 5 min. The supernatant was removed, the pellet washed with 200 ml of ethanol and the DNA-coated gold particles suspended in 36 ml of ethanol.
D. Target Tissue Establishment and Bombardment Immature embryos were removed from sorghum caryopses and cultured on N6 maintenance medium for 7 d. If the immature embryos are less than 0.5 mm they may die in culture and if they are larger than 1.5 mm they may precociously germinate instead of initiating into callus tissue. Four hours prior to bombardment, approximately 50 embryo-derived calli were placed in a circle (4 cm diameter) in the center of a Petri dish (15×100 mm) containing 0.2 M mannitol and 0.2 M sorbitol in N6 maintenance medium solidified with 2.5 g Phytagel. The Petri dish containing the target callus tissue was placed in the biolistic device and 10 ml of the DNA-gold suspension pipetted onto the center of a macroprojectile. The distance between the stopping plate and the target callus tissue was adjusted to 13 cm. The tissue was bombarded under vacuum with the rupture disk strength at 1100 p.s.i.

Callus tissue was sampled one day post bombardment using the GUS histochemical assay. Approximately twenty (20) replicates were performed for each promoter. The average number of blue foci per bombarded plate was determined for each reporter plasmid using a stereo microscope.

The ubi4 nucleotide sequence was sufficient to direct transient expression in monocotyledonous sorghum. Indeed, the ubi4 nucleotide sequences resulted in significantly higher levels of expression of GUS as compared to the levels of expression driven by each of the other tested promoters (data not shown). These results demonstrate that the ubi4 promoter in pubi4-GUS was sufficient to direct transient expression in monocotyledonous sorghum callus.

EXAMPLE 6

Transient Expression of pubi9-GUS in Pineapple Leaves, Protocorm-Like Bodies, Roots and Fruit Pineapple cultivar F153 leaves, protocorm-like bodies (plbs), roots and fruit were bombarded with a reporter plasmid [pAHC27, pubi9-GUS or pBI 121] described supra (Example 2). Target tissue (leaves, plbs, roots and fruit) was plated in the center (2.5 cm diameter) of petri plates in modified MS medium supplemented with 0.8% Difco Bacto agar and 3% sucrose. Bombardments were performed with a Bio-Rad helium gas-driven microprojectile accelerator (PDS-1000/He, Bio-Rad, Hercules, Calif.) with 1100 psi rupture discs. Gold microcarriers (1.6-µm-diameter, Bio-Rad) were coated with DNA using the CaCl2 precipitation method following the manufacturer's directions. Two ug of each DNA construct were used for each shot.

Histochemical GUS staining was performed 48 hours following bombardment to determine transient transformion. Five (5) or three (3) replicates were performed for each promoter in each type of bombarded tissue. The number of blue foci/plate of each bombarded tissue is shown in Table 4.

TABLE 4

Number of Blue Foci Per Plate In F153 Pineapple Tissues

| Plasmid | pAHC27 | ubi9-GUS | pBI121 |
|---------|--------|----------|--------|
| Leaves | 11.0 ± 7.0[a] | 244.0 ± 22.0 | — |
| Plbs | 142.0 ± 45.2 | 150.3 ± 52.3 | — |
| Roots | 3.2 ± 0.9 | 7.4 ± 2.2 | 1.6 ± 0.8 |
| Fruit | 8.7 ± 6.4 | 11.0 ± 3.7 | 14.2 ± 8.1 |

[a]Standard error.

The above data demonstrate successful transient expression of GUS under the control of the sugarcane polyubiquitin ubi9 promoter in pubi9-GUS in each of the four tissues of monocotyledonous pineapple.

EXAMPLE 7

Stable Expression of pubi4-GUS and pubi9-GUS in Transgenic Sugarcane Callus

Sugarcane callus cultures were initiated from stem apices (variety H62-4671) by surface sterilizing the plant material with 70% ethanol, cutting two mm transverse slices and growing on MS2 plates [1×Murashige and Skoog salts (GIBCO BRL #11117-074)], 1×minimal organics (GIBCO BRL#11118-023), 2 mg.L 2,4-D, 0.7% agar] under a 16 h light regime. After one to two months, callus was transferred to MSI plates [1×Murashige and Skoog salts (GIBCO BRL #11117-074), 1×minimal organics (GIBCO BRL #11118-023), 1 mg/L 2,4-D, 0.7% agar] and subcultured monthly.

Sugarcane callus was co-bombarded with a reporter plasmid (pubi4-GUS, pubi9-GUS, or pAHC27) and the selection plasmid pHA9 which contained the maize Ubi-1 promoter driving a neomycin phosphotransferase II (NPTII) gene (prepared as described supra in Example 2). Bombardment was with one micron gold particles and 1550 psi rupture discs. After bombardment, callus was kept on MS1 plates without selection for two weeks. After his recovery period, calli were transferred to MS1 plates with 50 mg/L G418 (Agri-bio) for one month, then transferred to MS1 plates with 100 mg/L G418 for 2–3 months. Calli which survived this selection were transferred to MS1 plates with 60 mg/L G418 for multiplication. Small calli totaling about 50 were randomly chosen from selected lines. These calli were assayed for GUS activity using the GUS-Light kit (Tropix) according tot the manufacturer's protocol, with 30 minutes incubation in GUS reaction buffer before chemiluminescence was measured. Two to ten 50 mg samples were assayed from each line, with three chemiluminescence assays for each sample.

Figure 12:
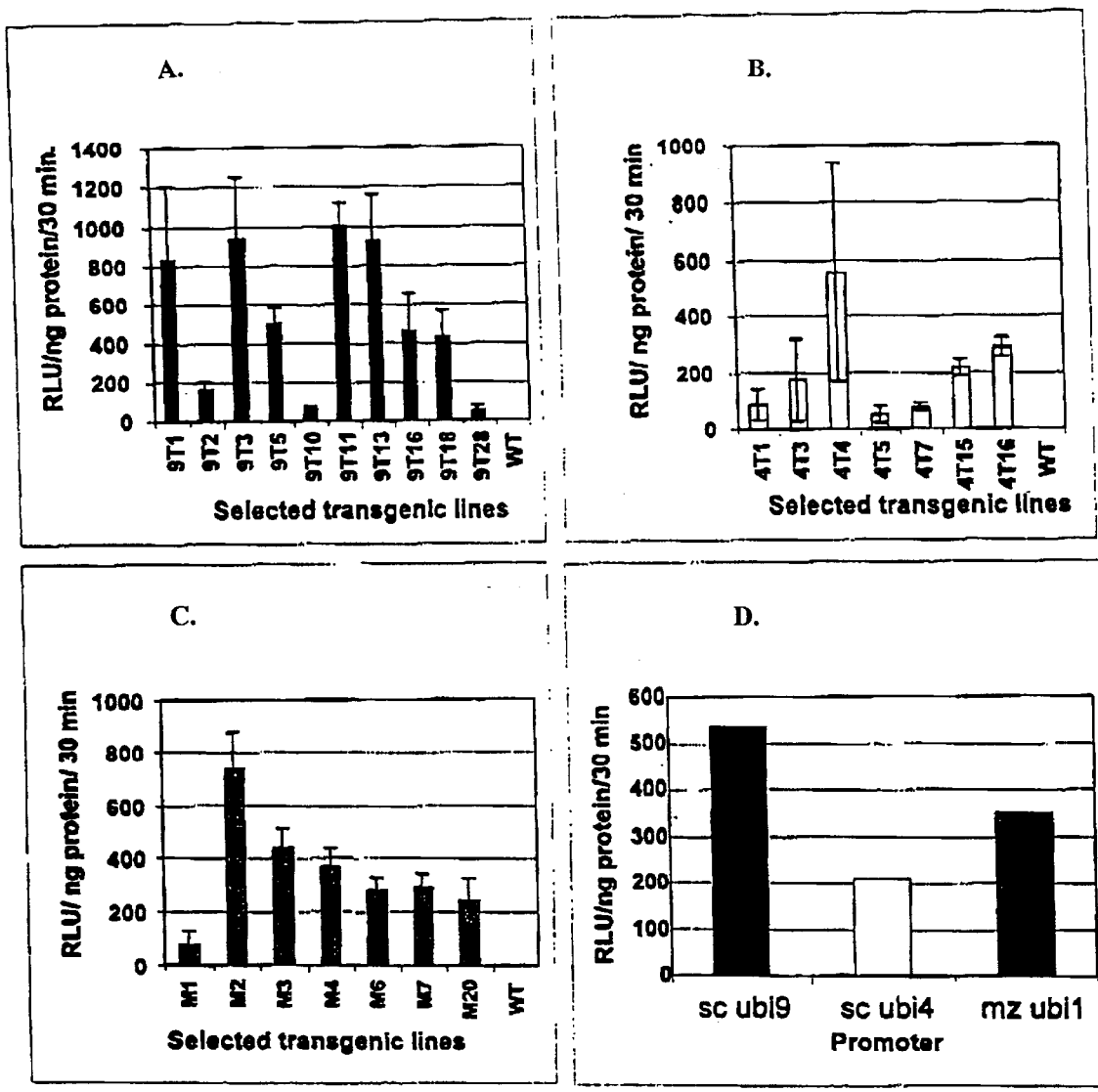
FIGS. 12(A–D) is a graph showing GUS activity following stable expression in sugarcane callus lines of GUS under the control of sugarcane ubi9 promoter (sc ubi9) (A, D), sugarcane ubi4 promoter (sc ubi4) (B, D), and maize Ubi-1 (C, D).

The results of the GUS chemiluminescent activity assays are shown in FIG. 12. In ten selected independent transgenic sugarcane callus lines, GUS expression from the sugarcane ubi9 promoter averaged 535.4 RLU/ng protein/30 min (FIGS. 12A, 12D). Seven selected stable transgenic lines expressing GUS under the control of the sugarcane ubi4 promoter averaged 209.3 RLU/ng protein/30 min (FIGS. 7B, & 7D), and seven lines expression GUS under the control of the maize Ubi-1 promoter averaged 348.2 RLU/ng protein/30 mon (FIGS. 7C, &D).

These results demonstrate that both the ubi4 and ubi9 nucleotide sequences in pubi4-GUS and pubi9-GUS, respectively, were sufficient to direct stable expression in monocotyledonous sugarcane callus.

EXAMPLE 8

Stable Expression of pCAM-ubi4-GUS, pCAM-ubi9-GUS, and pCAM-Ubi-1-GUS in Transgenic Rice Callus Agrobacterium strain EHA105 [Hood et al. J. Bacteriol. 168:1291–1301 (1986)] was used to transform rice callus. Reporter plasmids (pCAM-ubi9-GUS, pCAM-ubi4-GUS, pCAM-Ubi-1-GUS, and pCAM-5' M-ubi9-GUS-3' M, which were prepared as described in Example 2, supra] were introduced into Agrobacterium strain EHA105 by a standard procedure.

Rice callus was induced from scutellum tissue of rice (cv. Taipei 309) and transformed by Agrobacterium co-cultivation as previously described [Hiei et al., (1994) supra]. After 2–3 months on selection medium containing 100 mg/l hygromycin B (CalBiochem), small calli from selected lines were assayed for GUS activity by the chemiluminescence method described supra (Example 3).

PCR using one primer within the T-DNA and one outside of the T-DNA right border was used to confirm the absence of Agrobacterium contamination in tested callus lines using methods known in the art. Because rice transformation was by Agrobacterium, there is the possibility that the Agrobacterium were not killed after transformation, and thus that the GUS expression seen is from the Agrobacterium, not from transgenic rice cells. To test for this possibility, two PCRs were performed: one to test for the presence of the GUS gene, the second to test for the presence of vector plasmid sequences outside of the T-DNA. The Agrobacterium harbor a binary plasmid, one section of which contains the GUS encoding gene under the control of sugarcane promoter sequences. This section of the vector plasmid is called the T-DNA, and only this part is ordinarily transferred to the plant genome. A positive PCR for GUS indicates that the isolate plant DNA may be successfully amplified by PCR and the GUS gene is pressent (i.e., confirming the observation of GUS activity). A negative PCR for the vector plasmid outside of the T-DNA confirms that the entire plasmid, which is what is present in the Agrobacterium, is no longer present, i.e., that the T-DNA (which contains the GUS sequences under the control of the sugarcane promoter sequences) is successfully integrated into the plant genome.

Figure 13:
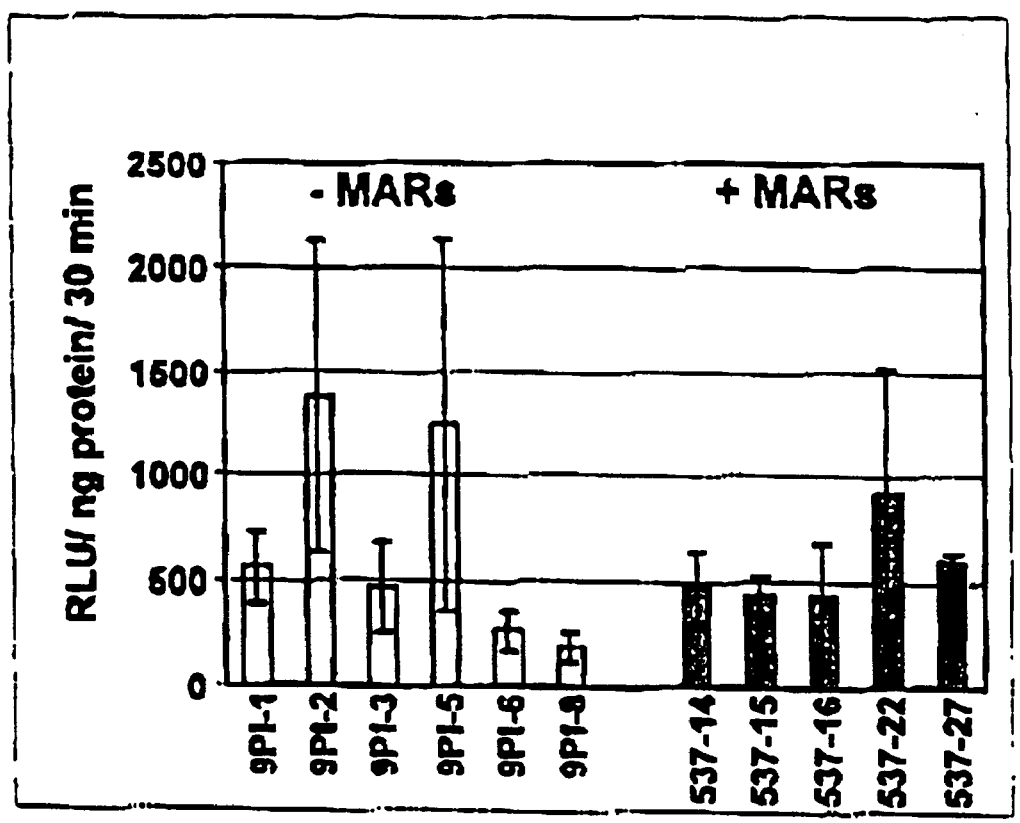
FIG. 13 is a graph showing GUS reporter gene activity in stable transgenic rice callus lines expressed under the control of the sugarcane ubi9 promoter in the presence and absence of the putative nuclear matrix attachment region (MAR).

One, seven, four, and two stably transformed transgenic rice callus lines were selected following co-cultivation of rice callus with Agrobacterium which had been transformed with the pCAM-ubi4-GUS, pCAM-ubi9-GUS, pCAM-5' M-ubi9-GUS-3' M, and pCAM-Ubi-1-GUS reporter plasmids, respectively. GUS expression in six transgenic lines transformed with the ubi9 promoter sequence is shown in FIG. 13. GUS expression in six transgenic lines transformed with the ubi9 promoter sequence averaged 681.0 RLU/ng protein/30 min.

Four stably transformed transgenic rice callus lines were selected following co-cultivation of rice callus with Agrobacterium which had been transformed with the pCAM-5' M-ubi9-GUS-3' M reporter plasmid. GUS expression in these transgenic lines averaged 567.7 RLU/ng protein/30 min. Since the pCAM-5' M-ubi9-GUS-3' M reporter plasmid differed from the pCAM-ubi9-GUS plasmid in additionally containing the putative 5' and 3' flanking nuclear matrix attachment regions (MARs), and since both the pCAM-ubi9-GUS and pCAM-5' M-ubi9-GUS-3' M reporter plasmids successfully resulted in expression of comparable levels of GUS in rice callus, these results demonstrate that the putative 5' and 3' flanking nuclear MARs are not necessary for promoter activity of the pubi9 sequences.

The results also suggest that either the polyubiquitin ubi4 or ubi9 promoter (with or without putative MARs) drives GUS expression at levels comparable to the maize Ubi-1 promoter in stable transgenic rice callus.

The above results demonstrate that the ubi9 promoter in pCAM-ubi9-GUS, and pCAM-5' M-ubi9-GUS-3' M was sufficient to direct stable expression in monocotyledonous rice callus.

EXAMPLE 9

Stable Expression of pBI-ubi4-GUS and pBI-ubi9-GUS in Transgenic Tobacco Leaves

*Agrobacterium tumefaciens* was used to transform tobacco leaves. Reporter plasmids pBI-ubi9-GUS, pBI-ubi4-GUS, pBI-Ubi-1-GUS, and pBI121, which were prepared as described in Example 2, supra), were introduced into leaf discs by an Agrobacterium mediated transformation procedure adapted from Horsch et al Science 227:1229–1231 (1985). Controls were untransformed.

Briefly, two ml overnight cultures of *Agrobacterium tumefaciens* were pelleted by brief centrifugation, decanted and resuspended in two ml of MSNTS liquid media (per liter of medium: one package MS salt mix [GIBCO BRL #11117-066], 30 g sucrose, 1.0 ml 1000×B5 vitamins, 50 µl 2 mg/ml α-naphthaleneacetic acetic acid [GIBCO BRL #21570-015], and 50 µl 20 mg/l benzyladenine [GIBCO BRL #16105-017]).

Aseptically grown tobacco leaves were harvested and placed in petri plates containing 20 ml MSNTS with 0.6 ml of the resuspended Agrobacterium and cut into approx. 1 cm squares with a sterile scalpel. After one to five minutes the leaf pieces were removed from the liquid, gently blotted on dry sterile paper, and placed on 0.8% agar MSNT plates (per liter of medium: one package MS salt mix [GIBCO BRL #11117-066], 30 g sucrose, 1.0 ml 1000×B5 vitamins, 8 g Bacto-Agar) with 500 µg/ml Cefotaxime (PhytoTechnology Laboratories). After two days, the leaf pieces were transferred to 0.8% agar MSNTS plates with 500 µg/ml Cefotaxime and 100 µg/ml Kanamycin (PhytoTechnology Laboratories). Shoots appeared after two to three weeks, at which time the shoots were transferred to Magenta boxes containing MSNT media with no antibiotics. To confirm Kanamycin resistance and to reduce the likelihood of obtaining chimeric plants, a "shooting assay" was used: leaves from putative transgenic plants were placed on 0.8% agar MSNTS plates containing 100 µg/ml Kanamycin. Shoots arising from these "shooting assays" were transferred to non-selective rooting media (MSNT) and grown in Magenta boxes.

Expression of GUS was determined as described in Example 3, supra. The results demonstrate that the both the ubi4 and ubi9 nucleotide sequences in pBI-ubi4-GUS and pBI-ubi9-GUS, respectively, were sufficient to direct stable expression in dicotyledonous tobacco leaves. Furthermore, the levels of GUS expression under the control of either the ubi4 and ubi9 nucleotide sequences in pBI-ubi4-GUS and pBI-ubi9-GUS were equal to or greater than the levels of GUS expression under the control of the maize Ubi-1 promoter. On the other hand, expression of GUS under the control of the CaMV 35 S promoter was greater than that under the control of either the sugarcane ubi4 or ubi9 promoters (data not shown).

EXAMPLE 10

Stable Expression of pubi4-GUS and pubi9-GUS in Transgenic Maize Embryos and Regeneration of Transgenic Maize Plants While transformation of maize embryos has not been carried out using the invention's sequences, this Example describes how the invention's sequences could be used and tested for expression of a gene of interest in maize embryos and for regeneration of transgenic maize plants.

Embryogenic corn cultures are initiated from immature maize embryos, bombarded simultaneously with a reporter plasmid (pubi4-GUS, pubi9-GUS, or pAHC27) and a selection plasmid (pHA9), and stably transformed corn plants regenerated as previously described by Brown et al., U.S. Pat. No. 5,593,874, incorporated by reference.

Briefly, embryogenic corn cultures are initiated from immature maize embryos of the "Hi-Ir" genotype which had been cultured 18–33 days on N6 2-100-25-Ag medium modified to contain 2 mg/L 2,4-dichlorophenoxyacetic acid, 180 mg/L casein hydrolysate, 25 mm L-proline, 10 µM silver nitrate, pH5.8, solidified with 0.2% Phytagel™ (Sigma). These embryogenic cultures are used as target tissue for transformation by particle gun bombardment.

A 1:1 mixture of the reporter vector (pubi-4-GUS, pubi-GUS or pAHC27) and selection plasmid (pHA9) is precipitated onto tungsten M10 particles by adding 12.5 of particles (25 mg/ml in 50% glycerol), 2.5 µl plasmid DNA (1 µg/µl), 12.5 µl 1M calcium chloride, and 5 µl 0.1M spermidine, and vortexing briefly. The particles are allowed to settle for 20 minutes, after which 12.5 µl of supernatant is removed and discarded. Each sample of DNA-tungsten is sonicated briefly and 2.5 µl is bombarded into the embryogenic cultures using a PDS-1000 Biolisitics particle gun (DuPont).

The bombarded tissue is transferred to fresh, nonselective medium the day after bombardment. Six days post-bombardment, the material is transferred to selective media containing 50 mg/L G418 (Agri-bio). After 2–3 weeks, the cultures are transferred to fresh media which contains 200 mg/L G418. The cultures are maintained on the 200 mg/L G418 media, transferred at 2–3 week intervals, until G418-resistant calli could be distinguished. G418-resistant calli are recovered from the embryogenic material. G418-resistant lines are bulked up and assayed for GUS expression using a histochemical or chemiluminescent assay as described supra (Example 3).

Plants are regenerated from the G418-resistant calli which express GUS activity in a three step regeneration protocol. All regeneration is performed on 200 mg/L G418. The first two steps are carded out in the dark at 28° C., and the final step under a 16:8 hour photoperiod, at about 25° C. Small green shoots that formed on Regeneration Medium 3 in 1000×25 mm Petri plates are transferred to Regeneration Medium 3 in 200×25 mm Pyrex™ or Phytatrays™ to permit further plantlet development and root formation. Upon formation of a sufficient root system, the plants are carefully removed from the medium, the root system washed under running water, and the plants placed into 2.5" pots containing Metromix 350 growing medium. The plants are maintained for several days in a high humidity environment, and then the humidity is gradually reduced to harden off the plants. The plants are transplanted from the 2.5" pots to 6" pots and finally to 10" pots during growth.

Corn plants regenerated from G418-resistant embryogenic calli which express GUS activity are tested for GUS expression using histochemical of chemiluminescent assays as described supra (Example 3). GUS expression (e.g., as determined by blue staining in the histochemical assay or by luminescence in the chemiluminescent assay) by one or more tissues of corn plants which are generated from calli that had been bombarded with pubi4-GUS or pubi9-GUS demonstrates that the ubi4 and ubi9 nucleotide sequences in pubi4-GUS and pubi9-GUS, respectively, are sufficient to direct stable expression in regenerated monocotyledonous maize plants.

EXAMPLE 11

Stable Expression of pBI-ubi4-GUS and pBI-ubi9-GUS in Transgenic Tomato Plants While transformation of tomatoes has not been carried out using the invention's sequences, this Example describes how the invention's sequences could be used and tested for expression of a gene of interest in tomato plants.

A reporter plasmid (pBI-ubi4-GUS or pBI-ubi9-GUS, prepared as described in Example 2) or a control plasmid (i.e., a plasmid which contains the uid A gene encoding GUS and which lacks a promoter sequence) are transformed into Agrobacterium, and the transformed Agrobacterium is used to infect tomato plants as previously described in Theologis et al., U.S. Pat. No. 5,723,766, incorporated by reference.

Briefly, a reporter plasmid or control plasmid is introduced into Agrobacterium strain LBA4404 as follows: *Agrobacterium tumefaciens* LBA-4404 (2 ml) is grown overnight at 28° C. in LB broth, and this used to inoculate 50 ml of LB broth to obtain the desired culture. The inoculated medium is grown at 28° C. until the $OD._{600}$ is 0.5–1.0. The cells are collected by centrifugation and the pellet is resuspended in 1 ml, 20 mM ice cold $CaCl_2$. To 100 $\mu$pl of the cell suspension, 1 $\mu$g of the plasmid is added, and the mixture is incubated on ice for 30 min before snap-freezing in liquid nitrogen. The cells are then thawed at 37° C. for 5 min and used to inoculate 1 ml LB. After 2 h growth at 28° C. with agitation, 100 $\mu$l of the culture are plated on LB+$Kanamycin_{50}$ medium; colonies are expected to appear in 2–3 days at 28° C. The cells are recultured by picking several colonies and streaking on LB+$Kanamycin_{50}$ medium; again, 3–4 colonies are picked from independent streaks and 5 ml cultures in LB+$Kanamycin_{50}$ medium are grown. Stationary phase cultures are used for transformion of tomato plants which are grown as described infra. Transformed Agrobacterium cells are frozen using 15% glycerol at −80° C. for later use.

To prepare host tomato plants, tomato seeds are sterilized using a protocol which consists of treatment with 70% ethanol for 2 min with mixing; followed by treatment with 10% sodium hypochlorite and 0.1% SDS for 10 min with mixing, followed by treatment with 1% sodium hypochlorite, 0.1% SDS for 30 min with mixing, and washing with sterile water 3 times for 2 min per wash. For germination of the sterilized seeds, 0.8 g of the sterilized seeds are placed in a Seed Germination Medium and grown for 2 weeks at low light in a growth room. After two weeks, when the seeds had germinated, cotyledons are dissected from the seedlings by cutting off the cotyledon tips and then cutting off the stem. This process is conducted in a large petri dish containing 5–10 ml of MSO medium.

Feeder plates are prepared from a tobacco cell suspension in liquid medium at 25° C. prepared with shaking at 130–150 rpm. The suspension is transferred to fresh medium at 1:10 dilution every 3–5 days. 1 ml of rapidly dividing culture is placed on the feeder plate, overlaid with filter paper and placed in low light in a growth room. The feeder plates are supplemented with 10 ml Feeder Medium Transformed Agrobacterium cultures which contain the reporter or control plasmids are inoculated into 50 ml LB containing kanamycin with a single colony of the strain. The culture is grown by shaking vigorously at 30° C. to saturation (OD>2.0 at 600 nm). The strain is chosen to come to full growth in less than 24 h. The culture is then diluted 5 times and split into 50 ml portions in plastic tubes.

Cotyledons from two of the feeder plates are scraped into each tube and rocked gently for 10–30 min. The cotyledons are then removed from the bacterial culture onto sterile filter paper (abaxial side up) on a tobacco feeder plate and incubated for 48 h in low light in a growth room. The cotyledons are then transferred axial side up to callus inducing medium. In the Callus inducing Medium, approximately four plates are used per magenta box, and the explants are crowded. The box is placed in a growth room for three weeks, and small masses of callus are expected to form at the surface of the cotyledons. The explants are transferred to fresh plates containing the callus inducing medium every three weeks. When the calli exceed 2 ml, they are transferred to plates containing shoot inducing medium. When the stem structure is evident, the shoots are dissected from the calli and the shoots are transferred to plates containing root inducing medium. After a vigorous root system is formed on the plants, the plantlets are transferred to soil by taking the plantlets from the plates, removing as much agar as possible and placing the plantlets in a high peat content soil in a small peat pot which fits into a magenta box with cover. When the seedling leaves reach the top of the box, the lid is loosened to uncover the box slowly over a period of 4–5 days. The plants are then transferred to a light cart and larger pots, and kept moist. Flowers of these regenerated plants are pollinated and tomatoes are developed.

Expression of GUS is measured in regenerated tomato plant tissues transformed with the reporter or control plasmids using a histochemical or chemiluminescent assays as described supra (Example 3). GUS expression by one or more tissues of tomato plants which are generated from tissue that had been transformed with pBI-ubi4-GUS or pBI-ubi9-GUS demonstrates that the ubi4 and ubi9 nucleotide sequences in pBI-ubi4-GUS and pBI-ubi9-GUS, respectively, are sufficient to direct stable expression in regenerated dicotyledonous tomato plants.

EXAMPLE 12

Stable Expression of pubi4-GUS and pubi9-GUS in Transgenic Soybean Excised Embryonic Meristems and Regeneration of Transgenic Soybean Plants While transformation of soybean excised embryonic meristems has not been carried out using the invention's sequences, this Example describes how the invention's sequences could be used and tested for expression of a gene of interest in soybean excised embryonic meristems and regeneration of transgenic soybean plants.

Soybean explants are derived from excised meristems, bombarded simultaneously with a reporter plasmid (pubi4-GUS, pubi9-GUS, or pAHC27) and a selection plasmid (pHA9), and stably transformed soybean plants are regenerated as previously described by Christou et al., U.S. Pat. No. 5,015,580, incorporated by reference.

Briefly, soybean explants of cultivar Williams 82 are derived from meristems excised from the embryonic axes of immature seeds. Primary leaves are removed and the explant plated on a target plate containing 1% water agar. The explants are transformed with a reporter plasmid or a selection plasmid loaded at 1.0–0.001 μg/ml of beads. The particle accelerator is charged at 13–16 kV. The carrier is loaded with 0.05–0.40 mg of loaded beads per square centimeter, with a preferred level of loading of 0.2 mg/cm$^2$.

The bombarded explants are then plated in the dark on modified MS basal medium which has a high level (i.e., 13.3 μM) of the cytokinin benzylaminopurine. Following incubation of 1 to 2 weeks in the dark, the tissues are transferred onto the same basal medium at a lower (1.7 μM) level of cytokinin to promote shoot elongation. Shoots are harvested at 0.5 to 1 cm in height.

The success of the transformation protocol is verified by fixing transformed explants at each stage to assay for GUS activity as described supra (Example 3). Two days after DNA particle injection, dozens of GUS active cells are expected to be detected in each explant. At 6 to 8 weeks, the plants are assayed for GUS activity in the shoot. Most plants are expected to be chimeric, having streaks of blue (i.e., GUS-expression cells) when assayed using the histochemical assay.

The transformed excised meristem tissue is used to regenerate fully mature, and sexually mature chimeric plants using methods known in the art such as those described in U.S. Pat. No. 5,015,580 to Christou et al. (incorporated by reference). GUS expression by one or more tissues of soybean plants which are regenerated from excised embryonic meristems that had been transformed with pubi4-GUS or pubi9-GUS demonstrates that the ubi4 and ubi9 nucleotide sequences in pubi4-GUS and pubi9-GUS, respectively, are sufficient to direct stable expression in regenerated dicotyledonous soybean plants.

EXAMPLE 13

Transient Expression of pubi4-GUS and pubi9-GUS in Banana Callus and Maize Leaves The ability of sugarcane polyubiquitin promoters ubi4 and ubi9 to drive GUS expression was also examined in a transient expression system in which banana embryo-derived callus and maize leaves were bombarded with the same constructs as described above. This Example demonstrates transient transformation of banana callus and maize leaves using the invention's ubi4 and ubi9 promoter sequences.

A. Plant Materials

Sweet corn seeds were sterilized with 70% ethanol for 3 min and then with 1.5% Clorox for 30 min, rinsed with sterile water and allowed to germinate on N6F medium [Hiei et al. (1994) Plant J 6:271–82.]. After 2 weeks, leaves from small seedling were harvested for transient expression assays. Banana calli were generated using methods known in the art, and provided by Dr. John Hu at University of Hawaii at Manoa.

B. Construction of Reporter Plasmids

The reporter plasmids pubi4-GUS, pubi9-GUS, and pAHC27 which were used in the transformation experiments were prepared as described supra, Example 2 [see, also, Wei et al. (1999) J. Plant Physiol. 155:513–519].

C. Particle Bombardment

DNA reporter constructs, pubi4-GUS, pubi9-GUS, pAHC27 [described supra; and Wei et al. (1999) supra] were introduced into maize leaves and banana callus by particle bombardment at 1100 psi using a PDS1000 biolistic particle accelerator (BioRad). A randomized complete block design (without sub-sampling) was used. In banana, the experiment consisted of 3 treatments (3 promoters), and 3 replications. In maize, the experiment consisted of 3 treatments (3 promoters), and 4 replications.

D. Histochemical Staining 48 h after bombardment, plant tissues were washed with 0.1 M sodium phosphate buffer (pH7.0) and transferred to the GUS staining solution containing 2 mM X-Gluc (5-bromo-4-chloro-3-indolyl-β-D-glucuronide; Clontech), 50 mM sodium phosphate buffer, 10 mM EDTA and 0.1% Triton X-100. After 12–16 h, the number of blue foci was counted under a dissecting microscope.

E. Chemiluminescent Assay

Chemiluminescent assay of GUS activity was performed using the GUS-Light kit (Tropix) and an MLX plate reader luminometer (DYNEX).

F. Transient Transformation of Banana Callus

Figure 16:
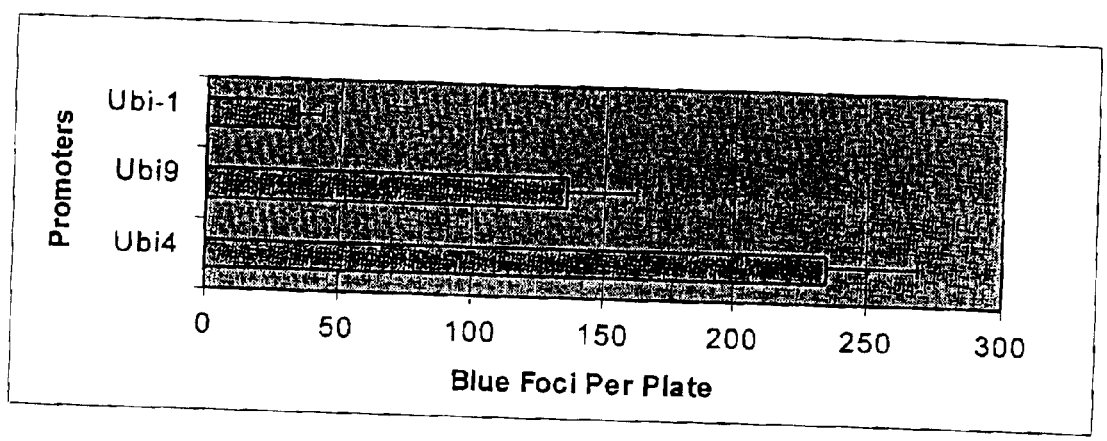
FIG. 16 is a graph showing the number of blue foci formed as a result of GUS activity following transient expression of GUS under the control of the sugarcane ubi4 promoter (ubi4), sugarcane ubi9 promoter (ubi9), and maize Ubi-1 promoter (Ubi-1) in banana callus.

The maize Ubi-1 promoter was used for comparison. The ubi9 promoter exhibited 4-fold higher promoter activity than the maize Ubi-1 promoter activity. The difference between the promoter activities of ubi9 and Ubi-1 was highly significant ($P \leq 5\%$). Substantially higher promoter activity was obtained with the ubi4 promoter, which produced nearly 7-fold higher promoter activity than the maize Ubi-1 promoter (FIG. 16). The experiment was repeated 3 in three plates, and the same relative expression levels were observed in each replication of experiment.

Another interesting observation was that the apparent size of the foci was much larger when using ubi4 than when using either ubi9 or maize Ubi-1. This data suggests that the observed difference in promoter activity between ubi4 and either ubi9 or Ubi-1 is an underestimate.

These results demonstrate successful transient transformation of banana callus using the invention's ubi4 and ubi9 promoter sequences.

G. Transient Expression in Maize Leaves

The results of transient expression experiments in which sweet corn leaves were bombarded with pubi4-GUS, pubi9-GUS, and pAHC27 are shown in Table 5.

TABLE 5

| Transient expression in maize leaves (Foci/Plate) | | | | |
|---|---|---|---|---|
| Replication | pubi4:GUS | pubi9:GUS | pHAC27 | Control |
| 1 | 17 | 118 | 60 | 0 |
| 2 | 16 | 141 | 51 | 0 |
| 3 | 70 | 79 | 52 | 0 |
| 4 | 40 | 58 | 99 | 0 |
| SUM | 143 | 396 | 262 | 0 |
| AVG | 35.8 | 99 | 65.5 | 0 |
| STDEV | 25.4 | 37.4 | 22.7 | 0 |

The data in Table 5 shows that the ubi9 promoter produced the highest promoter activity (as measured by the highest number of blue foci), maize Ubi-1 showed intermediate promoter activity, and ubi4 showed the lowest promoter activity. This result is consistent with the result of transient expression assays in sugarcane, described supra (Example 3).

EXAMPLE 14

Stable Transformation of Rice Calli and Expression in R0 and R1 Plants Regenerated Therefrom This Example demonstrates successful stable transformation of rice callus and of R0 and R1 generation plants regenerated therefrom.

A. Constructs

The introduction of transgene constructs into rice was accomplished by *Agrobacterium tumefaciens*-mediated transformation via a binary vector pCAMBIA1300 [Roberts et al. (1997) V.: "A comprehensive new set of modular vectors to allow both routine and advanced manipulations and efficient transformation of rice by both Agrobacterium and direct gene transfer methods," Rockefeller Foundation Meeting of the International Program on Rice Biotechnology, Malacca, Maylasia] which contains a hygromycin resistance gene near the left border of T-DNA. All constructs (shown in FIG. 17), pCAM-ubi4-GUS, pCAM-ubi9-GUS, pCAM-Ubi-1-GUS, were made by transferring the expression cassettes of pBI-ubi4-GUS, pBI-ubi9-GUS, and pBI-Ubi-1-GUS from pBI121 to pCAMBIA1300 as a HindIII and EcoR I fragment.

B. Rice Callus Culture

Mature Taipei 309 seeds were de-husked, sterilized with 70% ethanol for 1 min and then with 1.5% Clorox for 30 min, rinsed with sterile water and allowed to generate on N6F medium [Hiei et al. (1994) supra]. Scutella were excised from germinated seeds and cultured on fresh 2N6 medium for one month. Calli derived from scutella were proliferated on the same medium and then used for transformation.

C. Transformation of Rice Callus

Figure 17:
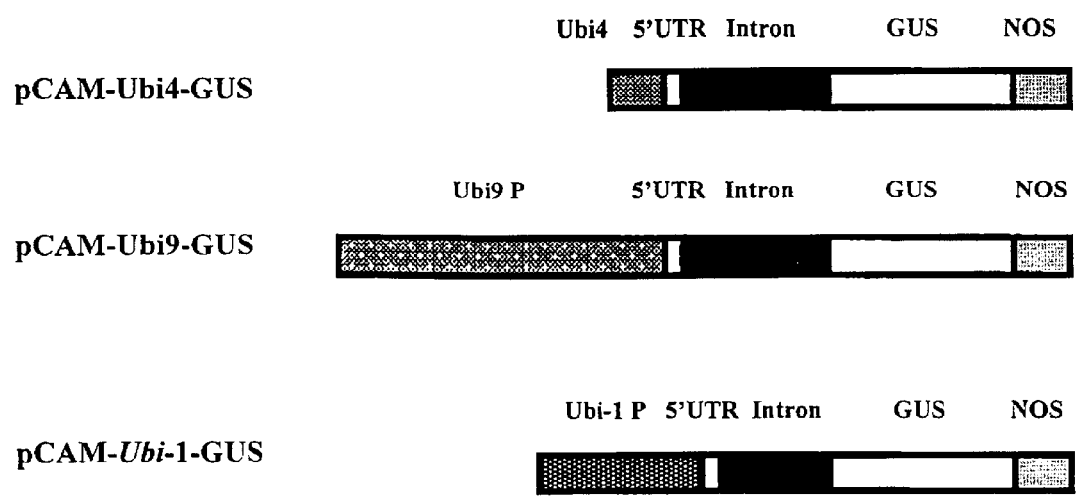
FIG. 17 is a diagramatic representation of the constructs used for rice callus transformation. All constructs were inserted into pCAMBIA 1300 binary vector.

*Agrobacterium tumefaciens* strain (EHA105) carrying one of the plasmid constructs of FIG. 17 was grown for 3 days in LB medium supplemented with 50 mg/l hygromycin and 50 mg/l kanamycin. The bacteria were collected and suspended at density of 4–5×10$^9$ cells/ml in AAM medium as described [Hiei et al. (1994) supra]. Rice calli were immersed in bacterial suspension for 10 min, and then were transferred to 2N6-AS medium [Hiei et al. (1994) supra] or MS2 medium [Dong and Hall (1996) Molecular Breeding 2:267–276] and incubated at 26° C. for three days. The calli were then washed with sterile water containing 250 mg/l cefotaxime (Agri-bio, USA, cat. #2000) and placed onto 2N6-CH medium [Hiei et al. (1994) supra], or MS2 containing 250 mg/l cefotaxime. Regeneration of rice plants took place as previously described on N6S3-CH medium [Hiei et al. (1994) supra] or MS4 [Dong and Hall (1996) supra].

D. ubi4 and ubi9 Promoter Activity in Stably Transformed Transgenic Rice Callus

Stably transformed rice calli were selected by 50 mg/l hygromycin B. The rice calli that could grow on the medium were stained with X-gluc for 12 h to detect the expression of GUS gene. DNA gel blot analysis was performed to confirm the integration of the transgene in the genome of those callus lines that exhibit GUS activity.

In rice callus lines, the level of GUS activity under the control of the three polyubiquitin gene promoters was comparable. Out of 9 transformed callus lines of pCAM-ubi9-GUS, three showed higher GUS expression than all transgenic callus lines of either pCAM-ubi4-GUS and pCAM-Ubi-1-GUS, two showed similar expression, and all the rest showed lower expression. The only transgenic callus line of pCAM-ubi4-GUS showed expression that exceeded two transgenic callus lines of pCAM-Ubi-1-GUS but was lower than the other two of pCAM-Ubi-1-GUS. When mean activity of each construct was calculated and compared, it was 690, 490, 542 GUS (ng)/soluble protein (mg) for pCAM-ubi4-GUS, pCAM-ubi9-GUS and pCAM-Ubi-1-GUS, respectively. However, a T test indicated the difference between any 2 of them was not significant at P$\leq$0.05. These results demonstrate that the invention's ubi4 and ubi9 sequences exhibited promoter activity in rice callus and that this promoter activity was comparable to that of Ubi-1.

E. ubi4 and ubi9 Promoter Activity in Stably Transformed R0 Transgenic Rice Plants Several rice transgenic callus lines were successfully regenerated. With respect to these, GUS expression in leaves, stems and roots was analyzed when plants grew to 3 months old. Plants regenerated from strongly expressing calli also showed high levels of GUS expression. Furthermore, the rank of expression levels remained similar among the different lines. However it was found that GUS expression in roots was up to 14 fold higher than that in calli. While it is not intended that the invention be limited to any particular mechanism, this difference may reflect developmental regulation of the promoter, or may reflect the difference in growth conditions between the growth chamber and greenhouse.

The ubi9 promoter was found to drive GUS expression at a level comparable to maize Ubi-1 promoter in leaves, stems, and roots. Although the transgenic rice callus line (9T5) which showed the highest level of GUS expression was not successfully regenerated, GUS expression in all tested tissues of transgenic rice plants which were regenerated from the second transgenic rice callus line (9T6) was higher than the level of GUS expression in all tested tissues of transgenic rice plants which were regenerated from calli transformed with the pCAM-Ubi-1-GUS construct. These results demonstrate that the relative promoter activity level in transformed rice calli is maintained in R0 generation rice plants which are regenerated from that callus.

The inventors also observed that the relative GUS activity (i.e., promoter activity) in roots, as normalized to total soluble protein, was much higher than that in leaves. The inventors had demonstrated in tobacco that the majority of this difference results from the much lower concentration of total of soluble protein in roots. Likewise, the majority of the difference in expression levels (i.e, promoter activity) between different tissues in rice also resulted from the difference of total soluble protein between the two tissues, which were usually 8–15 fold higher in leaves than in roots.

F. ubi4 and ubi9 Promoter Activity in Stably Transformed R1 Transgenic Rice Plants It has been reported that a bar gene driven by maize Ubi-1 promoter in transgenic rice plants which were generated via biolistics-mediated transformation was silenced in the RI generation [Kumpatla et al. (1997) Plant Physiol. 115:361–373]. To determine whether the GUS gene was expressed normally in R1 generation plants, GUS expression was examined several times in R1 generation rice plants derived from stably transformed rice callus using histochemical staining. No sign of transgene silencing was detected. Quantitative assays showed that expression in R1 transgenic rice plants was at the same or higher level as compared with R0 plants. These results indicate that high levels of expression driven by the ubi9 promoter, with highest levels in root tissue, are stably transmitted through meiosis in rice.

EXAMPLE 15

Stable Transformation of Sugarcane Calli and Plants Regenerated Therefrom

This Example demonstrates successful stable transformation of sugarcane callus and regeneration of sugarcane plants therefrom.

A. Constructs

The constructs used for stable transformation of sugarcane were the same constructs used for transient expression assays, i.e., pubi4-GUS, pubi9-GUS, and pAHC27 [Example 7, supra; Wei et al. (1999) supra]. pAHC27 [Christensen and Quail (1996) Plant Mol Biol 18:675–89], which harbors the maize Ubi-1 promoter-5' UTR-intron, the coding sequence of the Escherichia coli uid gene (which encodes β-glucuronidase, or GUS) and 3' terminus of Agrobacterium tumefaciens nopaline synthase (NOS) gene, was used for comparison.

B. Sugarcane Callus Culture

Embryogenic calli were initiated from the apices of H62-4671 (Saccharum spp. Hybrid) plants and grown on Murashige and Skoog medium with 3% sucrose and 0.2% 2,4-D (MS2). All calli were maintained on the same medium as above except that 2,4-D was decreased to 0.1% (MS1). Subculture of solid, healthy, and yellowish calli was performed monthly.

C. Transformation of Callus

Sugarcane transformation was carried out by microprojectile bombardment with a BioRad helium gas-driven apparatus PDS-100/He. pHA9 carrying a kanamycin resistant gene driven by the maize Ubi-1 promoter, was co-bombarded as the selectable marker. Gold particles of 1.6 and 1.0 μm (BioRad) were used as DNA-carriers. DNA coating and precipitation was according to previously disclosed methods [Klein et al. (1987) supra].

One- to two-months old sugarcane embryogenic calli were placed in the central area of a 9 cm diameter petri dish containing MS1 medium. After culturing for 1–2 days, each plate was bombarded two times with the rupture pressure of 1550 psi. The bombarded calli were transferred onto freshly-made MS1 medium for recovery. After 2 weeks, calli were transferred to the same medium with 50 μg/ml G418 for selection, which was increased to 100 μg/ml from the second transfer on. Subculture was done at an interval of one month.

D. ubi4 and ubi9 Promoter Activity in Stably Transformed Transgenic Sugarcane Calli 16 independent callus transgenic lines were recovered with both pubi4-GUS and pubi9-GUS constructs, and 9 independent callus transgenic lines were recovered with pAHC27. Southern blots of the transgenic sugarcane callus lines were performed. These blots showed a large number of hybridizing bands, and strong band intensity, indicating that transgene copy was very high. The large number of bands of other than the expected molecular weight indicate many copies have undergone rearrangements.

GUS activity in each transgenic callus line was determined soon after recovery. Comparison of ubi4 transgenic callus lines with transgenic callus lines of either ubi9 or maize Ubi-1 indicated that, while ubi4 showed promoter activity, it directed GUS expression at substantially lower levels than either the ubi9 or Ubi-1 promoters. Specifically, the GUS activity under the control of ubi4 is only 23.2% and 14% of the GUS activity under the control of ubi9 and Ubi-1, respectively.

The results also showed that the average GUS activity from 16 independent ubi9 transgenic lines was 65.8% higher than that from 9 independent maize Ubi-1 transgenic lines. This difference was significant ($P \leq 0.05$), suggesting that sugarcane ubi9 is a stronger promoter than maize Ubi-1 in sugarcane callus.

E. ubi4 and ubi9 Promoter Activity in Stably Transformed Transgenic Sugarcane Plants The majority of transgenic callus lines recovered with pubi4-GUS, pubi9-GUS, and pHAC27 were successfully regenerated. Histochemical staining was then employed to monitor the expression of the GUS reporter gene in the plant developmental stages. It was found that expression of GUS was still detectable in young seedlings grown in magenta boxes, but that it progressively decreased to undetectable levels after the seedlings were planted in pots and transferred to the green house. Although examination using histochemical staining at 3 and 6 months after planting detected no GUS expression, examination at 9 months successfully detected expression of GUS in some transgenic lines, albeit expression levels in plants were lower than those detected in calli.

The above results demonstrate that ubi4 and ubi9 promoters are efficient in directing reporter gene expression in sugarcane calli. However, the reporter gene expression was silenced in plants regenerated from these callus lines. The underlying mechanisms are being investigated. While an understanding of mechanism is not required to practice the invention, and without limiting the invention to any particular mechanism, this kind of homology-dependent gene silencing is very universal and is usually caused by the reporter gene, the vector, the transformation method (in particular, bombardment), the promoters, or even the structure generated during complicated integration of transgene into genome.

EXAMPLE 16

Transient Transformation of Garlic Suspension Cells

This Example demonstrates successful transient transformation of garlic suspension cultured cells.

A. Garlic Suspension Cells

Suspension cells (embryogenic and non-embryogenic) of garlic, *Allium sativum* L., of the following four types, CA Early 1, CA Early 2, CA Late 1, and CA Late 2, were prepared using methods known in the art. Cells were collected the night before all experiments by vacuum filtration on a 5 cm Whatman #4 filter paper and then transplanted onto a 9 cm Whatman #1 filter paper in a sterile petri plate containing callus induction media. Plates were stored in the dark until they were subjected to biolistic bombardment.

B. Transformation of Garlic Suspension Cells

Garlic suspension cells were bombarded with either the pubi4-GUS or pubi9-GUS constructs described supra using the Bio-Rad PDS/1000 He gun. The vacuum in the chamber was drawn to 28 in. Hg, the rupture pressure was 1100 psi using 1.6 micron gold particles which were prepared made just prior to bombardment at a distance to the plate of 6 cm. Controls were either not subjected to bombardment, or subjected to bombardment in the absence of the constructs.

C. Transient Expression of GUS Under Control of ubi4 and ubi9 Promoters

Two days following bombardment of garlic calli, a GUS assay was performed to determine the transient expression efficiency by counting the number of blue spots using a dissecting microscope. The results are shown in Table 6.

TABLE 6

Transformation Efficiency of pubi4-GUS and pubi9-GUS in Garlic, *Allium sativum* L., Suspension Cells

| Variety/Clone | Treatment | Number of Blue Spots |
|---|---|---|
| CA Early 1 | Not bombarded | 0 |
| | Bombarded - No DNA | 0 |
| | Bombarded - pubi4-GUS | 50.7 |
| | Bombarded - pubi9-GUS | 122.7 |

TABLE 6-continued

Transformation Efficiency of pubi4-GUS and pubi9-GUS in Garlic, *Allium sativum* L., Suspension Cells

| Variety/Clone | Treatment | Number of Blue Spots |
| --- | --- | --- |
| CA Early 2 | Not bombarded | 0 |
| | Bombarded - No DNA | 0 |
| | Bombarded - pubi4-GUS | 12 |
| | Bombarded - pubi9-GUS | 134.3 |
| CA Late 1 | Not bombarded | 0 |
| | Bombarded - No DNA | 0 |
| | Bombarded - pubi4-GUS | 24 |
| | Bombarded - pubi9-GUS | 51.8 |
| CA Late 2 | Not bombarded | 0 |
| | Bombarded - No DNA | 0 |
| | Bombarded - pubi4-GUS | 0 |
| | Bombarded - pubi9-GUS | 0 |

The results in Table 6 demonstrate that each of ubi4 and ubi9 was successful in bringing about transient gene expression in the three varieties CA Early 1, CA Early 2, and CA Late 1.

With respect to promoter activity, the ubi9 sequence showed a higher transformation efficiency (i.e., promoter activity) than the ubi4 sequence in each of the transformed garlic types (Table 6). Comparison of the results using pubi4 and pubi9 as promoters (Table 6) with the result obtained in other experiments in which the cauliflower mosaic virus (CaMV) 35S RNA promoter sequence was used showed that the promoter activity of ubi9 was comparable with the promoter activity of the CaMV 35S promoter.

From the above, it is clear that the invention provides promoter sequences which are capable of driving transgene expression in both monocotyledonous and dicotyledonous plant cells, and which are useful for generating transgenic plants with desirable agronomic characteristics.

What is claimed is:

1. A transgenic plant cell comprising a promoter comprising SEQ ID NO:10, wherein said promoter is operably linked to a nucleic acid sequence of interest, and said plant cell is selected from sugar cane, tobacco, sorghum, pineapple, rice, maize, tomato, soybean, banana, and garlic.

2. The transgenic plant cell of claim 1, wherein said plant cell is from garlic.

3. The transgenic plant cell of claim 1, wherein said plant cell is a leaf cell, root cell, fruit cell, or embryonic cell.

4. The transgenic plant cell of claim 1, wherein said plant cell is transiently transformed.

5. The transgenic plant cell of claim 1, wherein said plant cell is stably transformed.

6. A method for expressing a nucleic acid sequence of interest in a plant cell selected from sugar cane, tobacco, sorghum, pineapple, rice, maize, tomato, soybean, banana, and garlic, comprising:
   a) providing:
      i) said plant cell;
      ii) a nucleic acid sequence of interest; and
      iii) a promoter comprising SEQ ID NO: 10;
   b) operably linking said nucleic acid sequence of interest to said promoter to produce a transgene; and
   c) introducing said transgene into said plant cell to produce a transgenic plant cell under conditions such that said nucleic acid sequence of interest is expressed in said transgenic plant cell.

7. The method of claim 6, further comprising d) identifying said transgenic plant cell.

8. The method of claim 6, further comprising d) regenerating transgenic plant tissue from said transgenic plant cell.

9. The method of claim 6, further comprising d) regenerating a transgenic plant from said transgenic plant cell.

10. The method of claim 6, wherein said plant cell is from garlic.

11. The method of claim 6, wherein said plant cell is a leaf cell, root cell, fruit cell, or embryonic cell.

12. The method of claim 6, wherein said transgenic plant cell is transiently transformed.

13. The method of claim 6, wherein said transgenic plant cell is stably transformed.

* * * * *

SEQUENCE LISTING

```
<160> NUMBER OF SEQ ID NOS: 17

<210> SEQ ID NO 1
<211> LENGTH: 1813
<212> TYPE: DNA
<213> ORGANISM: Saccharum Hybrid Cultivar H32-8560
<220> FEATURE:
<221> NAME/KEY: misc_feature
<222> LOCATION: (243)
<223> OTHER INFORMATION: The "n" at position 243 is any nucleotide.
<220> FEATURE:
<221> NAME/KEY: misc_feature
<222> LOCATION: (245)
<223> OTHER INFORMATION: The "n" at position 245 is any nucleotide.
<220> FEATURE:
<221> NAME/KEY: misc_feature
<222> LOCATION: (790)
<223> OTHER INFORMATION: The "n" at position 790 is any nucleotide.
<220> FEATURE:
<221> NAME/KEY: misc_feature
<222> LOCATION: (1023)
<223> OTHER INFORMATION: The "n" at position 1023 is any nucleotide.
<220> FEATURE:
<221> NAME/KEY: misc_feature
<222> LOCATION: (1089)
<223> OTHER INFORMATION: The "n" at position 1089 is any nucleotide.
<220> FEATURE:
<221> NAME/KEY: misc_feature
<222> LOCATION: (1174)
<223> OTHER INFORMATION: The "n" at position 1174 is any nucleotide.
<220> FEATURE:
<221> NAME/KEY: misc_feature
<222> LOCATION: (1656)
<223> OTHER INFORMATION: The "n" at position 1656 is any nucleotide.

<400> SEQUENCE: 1
gaattcatta tgtggtctag gtaggttcta tatataagaa aacttgaaat gttctaaaaa      60
aaaattcaag cccatgcatg attgaagcaa acggtatagc aacggtgtta acctgatcta     120
gtgatctctt gcaatcctta acggccacct accgcaggta gcaaacggcg tccccctcct     180
cgatatctcc gcggcgacct ctggcttttt ccgcggaatt gcgcggtggg gacggattcc     240
acnanaccgc gacgcaaccg cctctcgccg ctgggcccca caccgctcgg tgccgtagcc     300
tcacgggact ctttctccct cctccccgt tataaattgg cttcatcccc tccttgcctc      360
atccatccaa atcccagtcc ccaatcccat cccttcgtcg gagaaattca tcgaagcgaa     420
gcgaatcctc gcgatcctct caaggtactg cgagttttcg atcccctct cgaccctcg      480
```

-continued

| | |
|---|---|
| tatgtttgtg tttgtcgtac gtttgattag gtatgctttc cctgtttgtg ttcgtcgtag | 540 |
| cgtttgatta ggtatgcttt ccctgttcgt gttcatcgta gtgtttgatt aggtcgtgtg | 600 |
| aggcgatggc ctgctcgcgt ccttcgatct gtagtcgatt tgcgggtcgt ggtgtagatc | 660 |
| tgcgggctgt gatgaagtta tttggtgtga tctgctcgcc tgattctgcg ggttggctcg | 720 |
| agtagatatg gatggttgga ccggttggtt cgtttaccgc gctaggggtg ggctgggatg | 780 |
| atgttgcatn gcgccgttgc gcgtgatccc gcagcaggac ttgcgtttga ttgccagatc | 840 |
| tcgttacgat tatgtgattt ggtttggact tattagatct gtagcttctg cttatgttgc | 900 |
| cagatgcgcc tactgctcca tatgcctgat gataatccat aaatggcagt ggaaatcaac | 960 |
| tagttgattg cggagtcatg tatcagctac aggtgtaggg actagctaca ggtgtaggga | 1020 |
| ctngcgtcta attgtttggt ccttaactca tgtgcaatta tgcaattag tttagatgtt | 1080 |
| tgttccaant catctaggct gtaaaaggga cactggttag attgctgttt aatctttta | 1140 |
| gtagattata ttatattggt aacttattaa cccntattaa catgccataa cgtggattct | 1200 |
| gctcatgcct gatgataatc atagatcact gtggaattaa ttagttgatt gttgaatcat | 1260 |
| gtttcatgta cataccacgg cacaattgct tagttcctta acaaatgcaa attttactga | 1320 |
| tccatgtatg atttgcgtgg ttctctaatg tgaaatacta tagctacttg ttagtaagaa | 1380 |
| tcaggttcgt atgcttaatg ctgtatgtgc cttctgctca tgcctgatga taatcatata | 1440 |
| tcactggaat taattagttg atcgtttaat catatatcaa gtacatacca tggcacaatt | 1500 |
| tttagtcact taacccatgc agattgaact ggtccctgca tgttttgcta aattgttcta | 1560 |
| ttctgattag accatatatc aggtatttt ttttggtaat ggttctctta ttttaaatgc | 1620 |
| tatatagttc tggtacttgt tagaaagatc tggttncata gtttagttgc ctatccttcg | 1680 |
| aattaggatg ctgagcagct gatcctatag ctttgtttca tgtatcaatt cttttgtgtt | 1740 |
| caacagtcag tttttgttag attcattgta acttatgttc gcttactctt ctggtcctca | 1800 |
| atgcttgcag atg | 1813 |

<210> SEQ ID NO 2
<211> LENGTH: 2804
<212> TYPE: DNA
<213> ORGANISM: Saccharum Hybrid Cultivar H32-8560
<220> FEATURE:
<221> NAME/KEY: misc_feature
<222> LOCATION: (17)
<223> OTHER INFORMATION: The "n" at position 17 is any nucleotide.
<220> FEATURE:
<221> NAME/KEY: misc_feature
<222> LOCATION: (885)
<223> OTHER INFORMATION: The "n" at position 885 is any nucleotide.
<220> FEATURE:
<221> NAME/KEY: misc_feature
<222> LOCATION: (1463)
<223> OTHER INFORMATION: The "n" at position 1463 is any nucleotide.
<220> FEATURE:
<221> NAME/KEY: misc_feature
<222> LOCATION: (1712)
<223> OTHER INFORMATION: The "n" at position 1712 is any nucleotide.
<220> FEATURE:
<221> NAME/KEY: misc_feature
<222> LOCATION: (2495)
<223> OTHER INFORMATION: The "n" at position 2495 is any nucleotide.

<400> SEQUENCE: 2

| | |
|---|---|
| taatcctggg ccatgancag ctgtccttcc aggttcacaa gtctggtgcc ttcttctgtc | 60 |
| cctccgatgg agattatctg catgtcgtgg tcgtgtccta atcgaatcct cgttgaatcc | 120 |
| ctatgttttt cttcaagaaa tgtgagtcct atgtcagtct ggttgcgttt gtgaacattt | 180 |

-continued

| | |
|---|---|
| ctgctgctga gcagcacttt ggctggaact gtgcaatgaa ataaatggaa ccctggtttc | 240 |
| tggttatgtg tgtgttagct aatgtttttg aagtggaagc tctaatcttc tatcgcgttg | 300 |
| ctactacaat tctgcttgtg ttttgatggt tcttggtttc tgttagttgg ttcagaggaa | 360 |
| gttttgcttc cacagactaa gatgcagttg aactttggtt gccctggttt ctagatttca | 420 |
| tttgtgctgt tgagtgata gtaagaaaca accggtgttc acatataatc aggttttgtg | 480 |
| ctgctcgagt gatcgtcaaa accaccggt gttcacatct aaaaaggttt cgatccccag | 540 |
| gtttagatct cccgtttaat tccaaaaaaa aagttctgtg tacttgcatt tagttgggtg | 600 |
| gttgatgctg gaaagagtaa cttttcaagag taataatctt tggtgactac tctgtttcaa | 660 |
| ctgatcaatc cctaggaaag gtacaccttt acttagggaa gaaattctta gaaccttgca | 720 |
| ctttgtttca actgataata gtatacttta ttagataaaa aatattcaga tatattagac | 780 |
| accggatgtc atccactcat ccttacaaac ctctgtcatg gtcctgcaga aatgtttgcc | 840 |
| agctccagtg gcttcctgat aaatctgtgg agtgcctgtt aatcngctgc caattttgc | 900 |
| tgagcactgt atatatgtta gtaagtacta ttgggccacc aattccattt tgacacagca | 960 |
| ctattggtcc accaattcga tcctgacaca gcactgcata atttgaaacg ttttgctcc | 1020 |
| cattttgcaa ggctacaaat ttagatcatg tttascatyc tgtgggatac aatatatgga | 1080 |
| tatcgaacaa acttggtatg tcagagaaaa aatagtttat tttcaaaact aacatttta | 1140 |
| aagccttcta tgaactttaa accttcagca tttgggatca agatgagtgc tcgaacaaga | 1200 |
| gtgcacttt tctccaaaat aatctactac agagttcttt tttatatata aaaaactta | 1260 |
| tacttaacag ataaatcaga cctcttctgc tccatatcac cttgacaaat caagaagca | 1320 |
| gcaccagcga agggtattat tattgaggta aatataagat ctcgtttact gaaaagacc | 1380 |
| gcgtgtttac ctaaactacc attttgcttt gatagcagca tacatgtgat agaattgcgg | 1440 |
| atcctaccgt gctgactgtg aangtggtaa gggtgagaga ttggtgggcg aggtctgaac | 1500 |
| gagcgaaaac agtactgcat ttactgttca caaggaggcg gcttaggttt tggtctccca | 1560 |
| gctctctaag ggaagctgag aattatgatt ctcttgctta attatttctt aaccaaagtt | 1620 |
| ataaatatat agcctatgag atcctaattt atggaaataa ctaaactatt ttaaggaaat | 1680 |
| atataaatag ataatcagcc cactaacggg cntagcgccc actaacaggc ctggtgctga | 1740 |
| gcccgacata acatctctcc ccgcctggrg aaacagctcg tcctcgagct gaaatctggt | 1800 |
| agaagcatcw tcaaccaaca ccggggtcat gctggaacac tgcatcaggc gctaccgcag | 1860 |
| ctggtacgtc gtcgtcgagg aagtcagccg actccaagta gaacagtcgc ttacaactga | 1920 |
| tgtccgcgga cgtagggctc atcacaattg taaacaaagc cctygacgac ggcactccaa | 1980 |
| acagctcttc cggtgtgaga cgacgaaacg agggagctag agcgggtagt ggcgcgggga | 2040 |
| acagccagtg tagcgcctgt agtcaccgag ggatggggcg gtcgggcgcc gcgaggctgc | 2100 |
| ggtgccaggt ggaggttcaa cattcttcaa acgcccgtgc caagtacatg gcggactgga | 2160 |
| ggtcgggcgg tgcgcggagc tgaacctgct tacggaggtg gtccggcagc ccacccacgt | 2220 |
| acaactccgc cttttggcga gcggagaggt tgtgggcatg gcacaggacg gcgttgtaac | 2280 |
| gctccgagta atcctgaacg gaagaaccaa aaggaaggcg ggcaagctcc gccaaccgag | 2340 |
| tgcccaaaac aggaggcccg aagcgaagcg agcataattc gcggaagcgc tcccaaggag | 2400 |
| gcatacctc gtcttgctcc agggcgtagt accatgtctg gcaacaccc cgaagatggt | 2460 |
| aggacgcgag ccatgtgcga gcggaggcga gcgtntgctg gccgcggaag aactgctcgc | 2520 |
| actggttcaa ccaattcagg ggatcggtcg aaccgtcgta cgtagggaac tccagttttgt | 2580 |

-continued

| | |
|---|---|
| agaatttggg ccccgcctgg gcgcctgcga gggcagcagc aagggctggg tcgagccccc | 2640 |
| cctgcggctg gccgcccgag ggagagggcg cccgaagaac agcggcccgt ccacccccc | 2700 |
| gaaaagagtg ctggcggggg gtagggagga catcgttgtc gccgccgccg tcgtgtaggc | 2760 |
| tgtcggggag ggcgacgtgg ccatcgagta gatccgggga attc | 2804 |

<210> SEQ ID NO 3
<211> LENGTH: 3691
<212> TYPE: DNA
<213> ORGANISM: Saccharum Hybrid Cultivar H32-8560
<220> FEATURE:
<221> NAME/KEY: misc_feature
<222> LOCATION: (9)
<223> OTHER INFORMATION: The "n" at position 9 is any nucleotide.
<220> FEATURE:
<221> NAME/KEY: misc_feature
<222> LOCATION: (3613)
<223> OTHER INFORMATION: The "n" at position 3613 is any nucleotide.

<400> SEQUENCE: 3

| | |
|---|---|
| aagttttgnt aaaatgaaca aagaattggg gaaactatag ccaaagtggg tggggaatgg | 60 |
| tgccaaacaa aacttcgtaa accaacccaa aaagatccgg aaaacaaatg gatacgtgca | 120 |
| gggcatgcat gcaatagccc agccataaaa agcggcgagc caatgcccgg gtgtcaaaca | 180 |
| aaatggcgcc tgtgccggct ctggctgctt ccggctcagc tttcggaacg atccgccgca | 240 |
| gtttggcctc gcatatgatg acgatgatgg tctcctcttc tcgatttgta gctccggcat | 300 |
| gggagccacc tcctgtcggc tcacacatag cacgcgcctt agcccgtgct cgctctcccc | 360 |
| tagatgcttc acctgcgcca atcagtgtga gcccatcgtg tcagatggta ctcgtacgta | 420 |
| tggagtaacg tgataccaca acacgtacac tggtcagaat tgatagtata tgatcctgtc | 480 |
| gacccgatgt gttttagtac cttgcagtgg ccggagagga gtggccgcgc gcatgcggcg | 540 |
| cagggggttct ccgcgctcgc tgatcgcttc ctcactgtgc gctcgtttag gaacaccacc | 600 |
| tcgtggtcgc tcaccatgtg tgactgcatg caacgctacg aatcaggacc cagatggaaa | 660 |
| cgaagcgcct ctcgaccacc tctgcctcgg tgatggttgg tgtgcagtgc gtacgcatgc | 720 |
| acgctaccaa tatcatacct ggatgccggt gcaatcgaac agcttcaggt tgtcgacgcg | 780 |
| gacggcgaag caggacgcgt acttccatat cttgggtc cattacgtac cgtcaatcga | 840 |
| ataaataaag agaagagttt gagatcagct tgttgggagc aggtgaccgc ccgacatgca | 900 |
| tgccgattgt cgacggcacg gaaataaaca acacatttgt gagggagcca gggaggcagt | 960 |
| ggcggcacag cgtcgcggca cagtcgatgc agaagtggtt cttgtcgttc ttgcgctccc | 1020 |
| cccgggtgtg cagcgcacgc ctttgaaaaa ctccgatagc aggccacaca gccattgcgg | 1080 |
| ggcgccgcgc acggccgcca gctgcatccc cgtttgttcg cacatgcgct aggtggtcct | 1140 |
| gcggccgttc cttgcaccgc ggagacgcgg ggtggaccag tggggaatg gatgaactgc | 1200 |
| tggtaggttt ggttggattg gcgagtgcgt agaggggca tgggcaacga tagactcgat | 1260 |
| tcaattcaaa gactgaaaat agtggagttc taacaccatt ctgtgcggcg ctaattctcg | 1320 |
| acatggcagg cgtaagcata ataccgacat ggcatgcaac gatgttcgtg aacagtggtg | 1380 |
| acacatggat atggtggccg tccagggat tcgttccatt caattcaaag accgaaaatc | 1440 |
| gcggggttcc gtagcatttt gtgcggtgct aattctcgaa catgcgagac gtaagcctaa | 1500 |
| taccgagatg gcatgcaaca atgttcgtga acaacagtga cacgtggatg cggtggccgt | 1560 |
| ctagggattc gcgttctaag ctggtatatg tgcggtgtta attcttgaca tgcggggcgt | 1620 |
| aagtgtaata ccaagatgaa cggtgacacg tggacgcggg ggtcgtcaaa caattcattc | 1680 |

```
cgtggtctag ggtaggttat atataaaggc cagtcttagt gggggatttt atggccatgt    1740
tattaatgca acccatattt ggaaaacagt gcaggaagag tttcatcttc gtaaaactct    1800
ctctaattcc atgaaactct tatcatctct ctcttcatca atacggtgcc acatcagcct    1860
atttaatgtc catgaaactc tgatgaaatc cactgagacg ggcctcagaa aacttgaaat    1920
cttctaaaaa aaattcaagt ccatgcatga ttgaagcaaa cggtatagca acggtgttaa    1980
cctgatctag tgatctcttg taatccttaa cggccaccta ccacaggtag caaacggcgt    2040 cccctcctc gatatctccg cggcggcctc tggcttttc cgcggaattg cgcggtgggg       2100
acggattcct cgagaccgcg acacaaccgc ctttcgccgc tgggcccac accgctcggt      2160 gccgtagcct cacgggactc tttctccctc ctcccccgct ataaattggc ttcatcccct     2220
ccttgcctca tccatccaaa tcccagtccc caatcccagc ccatcgtcgg agaaattcat    2280
agaagcgaag cgaatcctcg cgatcctctc aaggtagtgc gagttttcga ttcccctctc     2340 gaccctcgt atgctttccc tgtttgtgtt tcgtcgtagc gtttgattag gtatgctttc      2400
cctgtttgtg ttcgtcgtag cgtttgattt ggtatgcttt cccgttcgt gttcctcgta      2460 gtgtttgatt aggtcgtgtg aggcgatggc ctgctcgcat ccttcgatct gtagtcgatt    2520
tgcgggtcgt ggtgtagatc tgcgggctgt gatgaagtta tttggtgtga tcgtgctcgc    2580
ctgattctgc gggttggctc gagtagatat gatggttgga ccggttggtt tgtttaccgc    2640
gctagggttg ggctgggatg atgttgcatg cgccgttgcg cgtgatcccg cagcaggact    2700
tgcgtttgat tgccagatct cgttacgatt atgtgatttg gtttggactt tttagatctg    2760
tagcttctgc ttatgtgcca gatgcgccta ctgctcatat gcctgatgat aatcataaat    2820
ggctgtggaa ctaactagtt gattgcgag tcatgtatca gctacaggtg tagggactag     2880
ctacaggtgt agggacttgc gtctaaattg tttggtcctg tactcatgtt gcaattatgc    2940
aatttagttt agattgtttg ttccactcat ctaggctgta aaagggacac tgcttagatt    3000
gctgtttaat cttttagta gattatatat tatattggta acttattacc cttattacat     3060
gccatacgtg acttctgctc atgcctgatg ataatcatag atcactgtgg aattaattag    3120
ttgattgttg aatcatgttt catgtacata ccacggcaca attgcttagt tccttaacaa    3180
atgcaaattt tactgatcca tgtatgattt gcgtggttct ctaatgtgaa atactatagc    3240
tacttgttag taagaatcag gttcgtatgc ttaatgctgt atgtgccttc tgctcatgcc    3300
tgatgataat catatatcac tggaattaat tagttgatcg tttaatcata tatcaagtac    3360
ataccatggc acaatttta gtcacttaac ccatgcagat tgaactggtc cctgcatgtt    3420
ttgctaaatt gttctatttc tgattagacc atatatcatg taattttttt tttgggtaat    3480
ggttctccta ttttaaatgc tatatagttc tggtacttgt tagaaaaatc tgcttccata    3540
gtttagttgc ttatccctcg aattatgatg ctgagcagct gatcctatag ctttgtttca    3600
ggtatcaatt ctngtgttca acagtcagtt tttgttagat tcattgtaac ttatggtcgc    3660
ttactcttct ggtcctcaat gcttgcagat g                                    3691
```

<210> SEQ ID NO 4
<211> LENGTH: 343
<212> TYPE: DNA
<213> ORGANISM: Saccharum Hybrid Cultivar H32-8560
<220> FEATURE:
<221> NAME/KEY: misc_feature
<222> LOCATION: (59)
<223> OTHER INFORMATION: The "n" at this position is any nucleotide.

```
<220> FEATURE:
<221> NAME/KEY: misc_feature
<222> LOCATION: (286)
<223> OTHER INFORMATION: The "n" at this position is any nucleotide.
<220> FEATURE:
<221> NAME/KEY: misc_feature
<222> LOCATION: (294)
<223> OTHER INFORMATION: The "n" at this position is any nucleotide.
<220> FEATURE:
<221> NAME/KEY: misc_feature
<222> LOCATION: (319)
<223> OTHER INFORMATION: The "n" at position 319 is any nucleotide.

<400> SEQUENCE: 4
taagtcctgg gccatgagca gctgtccttc cagggttcac aagtagtggt gccttcttnc      60
tgtccctccg atggagatta tctgcatgtc gtggtcgtgt cctgatcgag tcgtcgttga     120
gtccctatgt tttttcttca agaaatgtga gtcctatgtc agtctggttg cgtttgtgaa     180
cattttctgc tgctgcgcag cagtttggtt ggaactgtgc aatgaaataa attgaaccct     240
ggtttctggt tatgtgtgtt agctaatgtt tttgaagtgg aagctntaat cttntatcgc     300
gttgctacta caattctgnt tgtgttttga tgttcttgtt tct                       343

<210> SEQ ID NO 5
<211> LENGTH: 5512
<212> TYPE: DNA
<213> ORGANISM: Saccharum Hybrid Cultivar H32-8560
<220> FEATURE:
<221> NAME/KEY: misc_feature
<222> LOCATION: (2218)
<223> OTHER INFORMATION: The "n" at position 2218 is any nucleotide.
<220> FEATURE:
<221> NAME/KEY: misc_feature
<222> LOCATION: (2227)
<223> OTHER INFORMATION: The "n" at position 2227 is any nucleotide.
<220> FEATURE:
<221> NAME/KEY: misc_feature
<222> LOCATION: (2229)
<223> OTHER INFORMATION: The "n" at position 2229 is any nucleotide.
<220> FEATURE:
<221> NAME/KEY: misc_feature
<222> LOCATION: (2249)
<223> OTHER INFORMATION: The "n" at position 2249 is any nucleotide.
<220> FEATURE:
<221> NAME/KEY: misc_feature
<222> LOCATION: (2282)
<223> OTHER INFORMATION: The "n" at position 2282 is any nucleotide.
<220> FEATURE:
<221> NAME/KEY: misc_feature
<222> LOCATION: (2327)
<223> OTHER INFORMATION: The "n" at position 2327 is any nucleotide.
<220> FEATURE:
<221> NAME/KEY: misc_feature
<222> LOCATION: (2341)
<223> OTHER INFORMATION: The "n" at position 2341 is any nucleotide.
<220> FEATURE:
<221> NAME/KEY: misc_feature
<222> LOCATION: (2477)
<223> OTHER INFORMATION: The "n" at position 2477 is any nucleotide.

<400> SEQUENCE: 5
gaattcatta tgtggtctag gtaggttcta tatataagaa aacttgaaat gttctaaaaa      60
aaaattcaag cccatgcatg attgaagcaa acggtatagc aacggtgtta acctgatcta     120
gtgatctctt gcaatcctta acggccacct accgcaggta gcaaacggcg tcccctcct      180 cgatatctcc gcggcgacct ctggcttttt ccgcggaatt gcgcggtggg gacggattcc     240
acaaccgcga cgcaaccgcc tctcgccgct gggcccaca ccgctcggtg ccgtagcctc     300
acgggactct ttctccctcc tcccccgtta taaattggct tcatcccctc cttgcctcat     360
```

```
ccatccaaat cccagtcccc aatcccatcc cttcgtcgga gaaattcatc gaagcgaagc      420
gaatcctcgc gatcctctca aggtactgcg agttttcgat cccctctcg acccctcgta       480 tgtttgtgtt tgtcgtacgt ttgattaggt atgctttccc tgtttgtgtt cgtcgtagcg     540
tttgattagg tatgctttcc ctgttcgtgt tcatcgtagt gtttgattag gtcgtgtgag     600
gcgatggcct gctcgcgtcc ttcgatctgt agtcgatttg cgggtcgtgg tgtagatctg     660
cgggctgtga tgaagttatt tggtgtgatc tgctcgcctg attctgcggg ttggctcgag     720
tagatatgga tggttggacc ggttggttcg tttaccgcgc tagggttggg ctgggatgat     780
gttgcatgcg ccgttgcgcg tgatcccgca gcaggacttg cgtttgattg ccagatctcg     840
ttacgattat gtgatttggt ttggacttat tagatctgta gcttctgctt atgttgccag     900
atgcgcctac tgctccatat gcctgatgat aatccataaa tggcagtgga aatcaactag     960
ttgattgcgg agtcatgtat cagctacagg tgtagggact agctacaggt gtagggactg    1020
cgtctaattg tttggtcctt aactcatgtg caattatgca atttagttta gatgtttgtt    1080
ccaatcatct aggctgtaaa agggacactg gttagattgc tgtttaatct ttttagtaga    1140
ttatattata ttggtaactt attaacccta ttacatgcca taacgtggat tctgctcatg    1200
cctgatgata atcatagatc actgtggaat taattagttg attgttgaat catgtttcat    1260
gtacatacca cggcacaatt gcttagttcc ttaacaaatg caaattttac tgatccatgt    1320
atgatttgcg tggttctcta atgtgaaata ctatagctac ttgttagtaa gaatcaggtt    1380
cgtatgctta atgctgtatg tgccttctgc tcatgcctga tgataatcat atatcactgg    1440
aattaattag ttgatcgttt aatcatatat caagtacata ccatggcaca atttttagtc    1500
acttaaccca tgcagattga actggtccct gcatgttttg ctaaattgtt ctattctgat    1560
tagaccatat atcaggtatt ttttttggt aatggttctc ttatttaaa tgctatatag       1620 ttctggtact tgttagaaag atctggttca tagtttagtt gcctatcctt cgaattagga    1680
tgctgagcag ctgatcctat agctttgttt catgtatcaa ttcttttgtg ttcaacagtc    1740 agttttgtt agattcattg taacttatgt tcgcttactc ttctggtcct caatgcttgc     1800
agatgcagat cttcgttaag accctcactg gcaagaccat caccttgag gttgagtctt     1860 cagacamtat tgacmatgtc maggctaaga tacaggacaa ggaaggcatt cctccggatc    1920
agcagaggct gatctttgct ggcaagcagc tcgaggatgg ccgtacccta gytgactaca    1980
acatccagaa ggagtccacc stccacctgg tgctcaggct cagggaggc atgcaaatct     2040 tcgtcaagac cctcactggc aagactatca cgcttgaggt cgagtcttct gacacgatcg    2100
acaacgtgaa ggccaagatc caggacaagg agggaatccc ccggaccag cagcgtctca     2160 tcttcgctgg caagcagctc gaggatggcc gcaccctcgc tgactacaac atccagangg    2220
agtcgantnt ccaccttgtg ctcaggttna ggggtggcat gcagatttt gtcaagacct     2280 tnactggcaa gaccatcacc ttggaggtgg agtcttcgga caccatngac aatgtgaagg    2340
ngaagatcca ggacaaggaa ggaatccccc cagaccagca gcgtcttatt tttgctggca    2400
agcagcttga ggatggccgc accctagcag actacaacat ccagaaggag tccacccttc    2460
acctggtgct ccgcttncgc ggtggtatgc agatcttcgt caagaccctc accggcaaga    2520
ccatcaccct ggaggtggag tcctctgaca ccatcgacaa tgtgaaggcg aagatccagg    2580
acaaggaggg catcccccg gaccagcagc gtctcatctt cgccggcaag cagctggagg     2640
atggccgcac cctggcagac tacaacatcc agaaggagtc cactctccac ctggtgctcc    2700
gtctccgtgg tggccagtaa tcctgggcca tgaagctgtc cttccaggtt cacaagtctg    2760
```

-continued

```
gtgccttctt ctgtccctcc gatggagatt atctgcatgt cgtggtcgtg tcctgatcga    2820
atcctcgttg aatccctatg ttttcttca agaaatgtga gtcctatgtc agtctggttg     2880
cgtttgtgaa catttctgct gctgagcagc actttggctg aactgtgca atgaaataaa     2940 tggaaccctg gtttctggtt atgtgtgtgt tagctaatgt ttttgaagtg gaagctctaa    3000
tcttctatcg cgttgctact acaattctgc ttgtgttttg atgttcttgg tttctgttag    3060
ttggttcaga ggaagttttg cttccacaga ctaagatgca gttgaacttt ggttgccctg    3120
gtttctagat ttcatttgtg ctggttgagt gatagtaaga aacaaccggt gttcacatat    3180
aatcaggttt tgtgctgctc gagtgatcgt caaaaaccac cggtgttcac atctaaaaag    3240
gtttcgatcc ccaggtttag atctcccgtt taattccaaa aaaaaagttc tgtgtacttg    3300
catttagttg ggtggttgat gctggaaaga gtaactttca agagtaataa tctttggtga    3360
ctactctgtt tcaactgatc aatccctagg aaaggtacac ctttacttag ggaagaaatt    3420
cttagaacct tgcactttgt ttcaactgat aatagtatac tttattagat aaaaaatatt    3480
cagatatatt agacaccgga tgtcatccac tcatccttac aaacctctgt catggtcctg    3540
cagaaatgtt tgccagctcc agtggcttcc tgataaatct gtggagtgcc tgttaatcgg    3600
ctgccaattt ttgctgagca ctgtatatat gttagtaagt actattgggc caccaattcg    3660
attttgacac agcactattg gtccaccaat tcgattctga cacagcactg cataatttga    3720
aacgtgttgc tccattttgc aaggctacaa atttagatca tgtttagcat tctgtgggat    3780
acaatatatg gatatcgaac aaacttggta tgtcagagaa aaaatagttt attttcaaaa    3840
ctaacatttt taaagccttc tatgaacttt aaaccttcag catttgggat caagatgagt    3900
gctcgaacaa gagtgcactt tttctccaaa ataatctact acagagttct tttttatata    3960
taaaaaaact tatacttaac agataaatca gacttttct gctccatatc accttgacaa     4020
atcaaagaag cagcaccagc gaagggtatt attattgagg taaatataag atctcgttta    4080
ctgaaaaaga ccgcgtgttt acctaaacta ccatttgct tgatagcag catacatgtg      4140 atagaattgc ggatcctacc gtgctgactg tgaaggtgg aggggtgaga gattggtggg     4200
cgaggtctga acgagcgaga acagtactgc atttactgtt cacaaggagg cggcttaggt    4260
tttgggtctc ccagctctct aagggaagct gagaattatg attctcttgc ttaattattt    4320
cttaaccaaa gttataaata tatagcctat gagatcctaa tttatggaaa taactaaact    4380
atttaaggaa aatatataaa tagataatca gcccactaac gggcctagcg cccactaaca    4440
ggcctggtgc tgagcccgac ataacatctc tccccgcctg gagaaacagc tcgtcctcga    4500
gctgaaatct ggtagaagca tcatcaacca acaccgggt catgctggaa cactgcatca    4560
ggcgctaccg cagctggtac gtcgtcgtcg aggaagtcag ccgactccaa gtagaacagt    4620
cgcttacact gatgtccgcg gacgtagggc tcatcacaat tgtaacaaag cccttgacga    4680
cggcactcca acagctcctc cggtgtgaga cgacgaaacg agggagctag agcgggtagt    4740
ggcgcgggaa cagccagtgt agcgcctgta gtcaccgagg gatggggcgg tcgggcgccg    4800
cgaggctgcg gtgcaggtgg aggtttcaca ttcctcaaac gcccgtgcca agtacatggc    4860
ggactggagg tcggcggtg cgcggagctg aacctgctta cggaggtggt ccggcagccc    4920
acccacgtac aactccgcct tttggcgagc ggagaggttg tgggcatggc acaggacggc    4980
gttgtaacgc tccgagtaat cctgaacgga agaaccaaaa ggaaggcggg caagctccgc    5040
caaccgagtg cccaaaacag gaggcccgaa gcgaagcgag cataattcgc ggaagcgctc    5100
ccaaggaggc atacctcgt cttgctccag ggcgtagtac catgtctggg caacaccccg     5160
```

-continued

```
aagatggtag gacgcgagcc atgtgcgagc ggaggcgagc gtctgctggc cgcggaagaa    5220
ctgctcgcac tggttcaacc aattcagggg atcggtcgaa ccgtcgtacg tagggaactc    5280
cagtttgtag aatttgggcc ccgcctgggc gcctgcgagg gcagcagcaa gggctgggtc    5340
gagccccccc tgcggctggc cgcccgaggg agagggcgcc cgaagaacag cggcccgtcc    5400
acccccccga aaagagtgct ggcgggggt agggaagaca tcgttgtcgc cgccgccgtc     5460
gtgtaggctg tcggggaagg cgacgtggcc atcgagtaga tccggggaat tc            5512
```

<210> SEQ ID NO 6
<211> LENGTH: 305
<212> TYPE: PRT
<213> ORGANISM: Saccharum Hybrid Cultivar H32-8560
<220> FEATURE:
<221> NAME/KEY: VARIANT
<222> LOCATION: (22)
<223> OTHER INFORMATION: The "Xaa" at position 22 is any amino acid.
<220> FEATURE:
<221> NAME/KEY: VARIANT
<222> LOCATION: (25)
<223> OTHER INFORMATION: The "Xaa" at position 25 is any amino acid.
<220> FEATURE:
<221> NAME/KEY: VARIANT
<222> LOCATION: (27)
<223> OTHER INFORMATION: The "Xaa" at position 27 is any amino acid.
<220> FEATURE:
<221> NAME/KEY: VARIANT
<222> LOCATION: (57)
<223> OTHER INFORMATION: The "Xaa" at position 57 is any amino acid.
<220> FEATURE:
<221> NAME/KEY: VARIANT
<222> LOCATION: (67)
<223> OTHER INFORMATION: The "Xaa" at position 67 is any amino acid.
<220> FEATURE:
<221> NAME/KEY: VARIANT
<222> LOCATION: (139)
<223> OTHER INFORMATION: The "Xaa" at position 139 is any amino acid.
<220> FEATURE:
<221> NAME/KEY: VARIANT
<222> LOCATION: (142)..(143)
<223> OTHER INFORMATION: The "Xaa" at positions 142 and 143 is any amino
       acid.
<220> FEATURE:
<221> NAME/KEY: VARIANT
<222> LOCATION: (149)
<223> OTHER INFORMATION: The "Xaa" at position 149 is any amino acid.
<220> FEATURE:
<221> NAME/KEY: VARIANT
<222> LOCATION: (160)
<223> OTHER INFORMATION: The "Xaa" at position 160 is any amino acid.
<220> FEATURE:
<221> NAME/KEY: VARIANT
<222> LOCATION: (175)
<223> OTHER INFORMATION: The "Xaa" at position 175 is any amino acid.
<220> FEATURE:
<221> NAME/KEY: VARIANT
<222> LOCATION: (180)
<223> OTHER INFORMATION: The "Xaa" at position 180 is any amino acid.
<220> FEATURE:
<221> NAME/KEY: VARIANT
<222> LOCATION: (225)
<223> OTHER INFORMATION: The "Xaa" at position 225 is any amino acid.

<400> SEQUENCE: 6

Met Gln Ile Phe Val Lys Thr Leu Thr Gly Lys Thr Ile Thr Leu Glu
 1               5                  10                  15

Val Glu Ser Ser Asp Xaa Ile Asp Xaa Val Xaa Ala Lys Ile Gln Asp
             20                  25                  30

Lys Glu Gly Ile Pro Pro Asp Gln Gln Arg Leu Ile Phe Ala Gly Lys
         35                  40                  45

```
Gln Leu Glu Asp Gly Arg Thr Leu Xaa Asp Tyr Asn Ile Gln Lys Glu
 50                  55                  60

Ser Thr Xaa His Leu Val Leu Arg Leu Arg Gly Gly Met Gln Ile Phe
 65                  70                  75                  80

Val Lys Thr Leu Thr Gly Lys Thr Ile Thr Leu Glu Val Glu Ser Ser
                 85                  90                  95

Asp Thr Ile Asp Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Tyr Asn Ile Gln Xaa Glu Ser Xaa Xaa His
130                 135                 140

Leu Val Leu Arg Xaa Arg Gly Gly Met Gln Ile Phe Val Lys Thr Xaa
145                 150                 155                 160

Thr Gly Lys Thr Ile Thr Leu Glu Val Glu Ser Ser Asp Thr Xaa Asp
                165                 170                 175

Asn Val Lys Xaa Lys Ile Gln Asp Lys Glu Gly Ile Pro Pro Asp Gln
            180                 185                 190

Gln Arg Leu Ile Phe Ala Gly Lys Gln Leu Glu Asp Gly Arg Thr Leu
        195                 200                 205

Ala Asp Tyr Asn Ile Gln Lys Glu Ser Thr Leu His Leu Val Leu Arg
210                 215                 220

Xaa Arg Gly Gly Met Gln Ile Phe Val Lys Thr Leu Thr Gly Lys Thr
225                 230                 235                 240

Ile Thr Leu Glu Val Glu Ser Ser Asp Thr Ile Asp Asn Val Lys Ala
                245                 250                 255

Lys Ile Gln Asp Lys Glu Gly Ile Pro Pro Asp Gln Gln Arg Leu Ile
            260                 265                 270

Phe Ala Gly Lys Gln Leu Glu Asp Gly Arg Thr Leu Ala Asp Tyr Asn
        275                 280                 285

Ile Gln Lys Glu Ser Thr Leu His Leu Val Leu Arg Leu Arg Gly Gly
    290                 295                 300

Gln
305
```

<210> SEQ ID NO 7
<211> LENGTH: 1802
<212> TYPE: DNA
<213> ORGANISM: Saccharum Hybrid Cultivar H32-8560

<400> SEQUENCE: 7

```
gaattcatta tgtggtctag gtaggttcta tatataagaa aacttgaaat gttctaaaaa    60
aaaattcaag cccatgcatg attgaagcaa acggtatagc aacggtgtta acctgatcta   120
gtgatctctt gcaatcctta acggccacct accgcaggta gcaaacggcg tcccctcct    180
cgatatctcc gcggcgacct ctggctttt ccgcggaatt gcgcggtggg gacggattcc    240
acaaccgcga cgcaaccgcc tctcgccgct gggcccaca ccgctcggtg ccgtagcctc     300
acgggactct ttctccctcc tccccgtta taaattggct tcatcccctc cttgcctcat    360
ccatccaaat cccagtcccc aatcccatcc cttcgtcgga gaaattcatc gaagcgaagc   420
gaatcctcgc gatcctctca aggtactgcg agttttcgat ccccctctcg accctcgta    480
tgtttgtgtt tgtcgtacgt ttgattaggt atgctttccc tgtttgtgtt cgtcgtagcg    540
tttgattagg tatgctttcc ctgttcgtgt tcatcgtagt gtttgattag gtcgtgtgag   600
```

```
-continued gcgatggcct gctcgcgtcc ttcgatctgt agtcgatttg cgggtcgtgg tgtagatctg    660
cgggctgtga tgaagttatt tggtgtgatc tgctcgcctg attctgcggg ttggctcgag    720
tagatatgga tggttggacc ggttggttcg tttaccgcgc tagggttggg ctgggatgat    780
gttgcatgcg ccgttgcgcg tgatcccgca gcaggacttg cgtttgattg ccagatctcg    840
ttacgattat gtgatttggt ttggacttat tagatctgta gcttctgctt atgttgccag    900
atgcgcctac tgctccatat gcctgatgat aatccataaa tggcagtgga aatcaactag    960
ttgattgcgg agtcatgtat cagctacagg tgtagggact agctacaggt gtagggactg   1020
cgtctaattg tttggtcctt aactcatgtg caattatgca atttagttta gatgtttgtt   1080
ccaatcatct aggctgtaaa agggacactg gttagattgc tgtttaatct ttttagtaga   1140
ttatattata ttggtaactt attaacccta ttacatgcca taacgtggat tctgctcatg   1200
cctgatgata atcatagatc actgtggaat taattagttg attgttgaat catgtttcat   1260
gtacatacca cggcacaatt gcttagttcc ttaacaaatg caaattttac tgatccatgt   1320
atgatttgcg tggttctcta atgtgaaata ctatagctac ttgttagtaa gaatcaggtt   1380
cgtatgctta atgctgtatg tgccttctgc tcatgcctga tgataatcat atatcactgg   1440
aattaattag ttgatcgttt aatcatatat caagtacata ccatggcaca attttttagtc   1500 acttaaccca tgcagattga actggtccct gcatgttttg ctaaattgtt ctattctgat   1560
tagaccatat atcaggtatt ttttttttggt aatggttctc ttattttaaa tgctatatag   1620
ttctggtact tgttagaaag atctggttca tagtttagtt gcctatcctt cgaattagga   1680
tgctgagcag ctgatcctat agctttgttt catgtatcaa ttcttttgtg ttcaacagtc   1740 agttttttgtt agattcattg taacttatgt tcgcttactc ttctggtcct caatgcttgc   1800
ag                                                                  1802

<210> SEQ ID NO 8
<211> LENGTH: 5174
<212> TYPE: DNA
<213> ORGANISM: Saccharum Hybrid Cultivar H32-8560
<220> FEATURE:
<221> NAME/KEY: misc_feature
<222> LOCATION: (9)
<223> OTHER INFORMATION: The "n" at position 9 is any nucleotide.
<220> FEATURE:
<221> NAME/KEY: misc_feature
<222> LOCATION: (4318)
<223> OTHER INFORMATION: The "n" at position 4318 is any nucleotide.
<220> FEATURE:
<221> NAME/KEY: misc_feature
<222> LOCATION: (4546)
<223> OTHER INFORMATION: The "n" at position 4546 is any nucleotide.
<220> FEATURE:
<221> NAME/KEY: misc_feature
<222> LOCATION: (4890)
<223> OTHER INFORMATION: The "n" at position 4890 is any nucleotide.
<220> FEATURE:
<221> NAME/KEY: misc_feature
<222> LOCATION: (5117)
<223> OTHER INFORMATION: The "n" at position 5117 is any nucleotide.
<220> FEATURE:
<221> NAME/KEY: misc_feature
<222> LOCATION: (5125)
<223> OTHER INFORMATION: The "n" at position 5125 is any nucleotide.
<220> FEATURE:
<221> NAME/KEY: misc_feature
<222> LOCATION: (5150)
<223> OTHER INFORMATION: The "n" at position 5150 is any nucleotide.
```

```
<400> SEQUENCE: 8
aagttttgnt aaaatgaaca aagaattggg gaaactatag ccaaagtggg tggggaatgg      60
tgccaaacaa aacttcgtaa accaacccaa aaagatccgg aaaacaaatg gatacgtgca     120
gggcatgcat gcaatagccc agccataaaa agcggcgagc caatgcccgg gtgtcaaaca     180
aaatggcgcc tgtgccggct ctggctgctt ccggctcagc tttcggaacg atccgccgca     240
gtttggcctc gcatatgatg acgatgatgg tctcctcttc tcgatttgta gctccggcat     300
gggagccacc tcctgtcggc tcacacatag cacgcgcctt agcccgtgct cgctctcccc     360
tagatgcttc acctgcgcca atcagtgtga gcccatcgtg tcagatggta ctcgtacgta     420
tggagtaacg tgataccaca acacgtacac tggtcagaat tgatagtata tgatcctgtc     480
gacccgatgt gttttagtac cttgcagtgg ccggagagga gtggccgcgc gcatgcggcg     540
cagggggttct ccgcgctcgc tgatcgcttc ctcactgtgc gctcgtttag gaacaccacc     600
tcgtggtcgc tcaccatgtg tgactgcatg caacgctacg aatcaggacc cagatggaaa     660
cgaagcgcct ctcgaccacc tctgcctcgg tgatggttgg tgtgcagtgc gtacgcatgc     720
acgctaccaa tatcatacct ggatgccggt gcaatcgaac agcttcaggt tgtcgacgcg     780
gacggcgaag caggacgcgt acttccatat cttttgggttc cattacgtac cgtcaatcga     840
ataaataaag agaagagttt gagatcagct tgttgggagc aggtgaccgc ccgacatgca     900
tgccgattgt cgacggcacg gaaataaaca acacatttgt gagggagcca gggaggcagt     960
ggcggcacag cgtcgcggca cagtcgatgc agaagtggtt cttgtcgttc ttgcgctccc    1020
cccgggtgtg cagcgcacgc ctttgaaaaa ctccgatagc aggccacaca gccattgcgg    1080
ggcgccgcgc acgccgcca gctgcatccc cgtttgttcg cacatgcgct aggtggtcct    1140
gcggccgttc cttgcaccgc ggagacgcgg ggtggaccag tgggggaatg gatgaactgc    1200
tggtaggttt ggttggattg gcgagtgcgt agaggggca tggcaacga tagactcgat    1260
tcaattcaaa gactgaaaat agtggagttc taacaccatt ctgtgcggcg ctaattctcg    1320
acatggcagg cgtaagcata ataccgacat ggcatgcaac gatgttcgtg aacagtggtg    1380
acacatggat atggtggccg tccagggat tcgttccatt caattcaaag accgaaaatc    1440
gcggggttcc gtagcatttt gtgcggtgct aattctcgaa catgcgagac gtaagcctaa    1500
taccgagatg gcatgcaaca atgttcgtga acaacagtga cacgtggatg cggtggccgt    1560
ctagggattc gcgttctaag ctggtatatg tgcggtgtta attcttgaca tgcggggcgt    1620
aagtgtaata ccaagatgaa cggtgacacg tggacgcggg ggtcgtcaaa caattcattc    1680
cgtggtctag ggtaggttat atataaaggc cagtcttagt gggggatttt atggccatgt    1740
tattaatgca acccatattt ggaaaacagt gcaggaagag tttcatcttc gtaaaactct    1800
ctctaattcc atgaaactct tatcatctct ctcttcatca atacggtgcc acatcagcct    1860
atttaatgtc catgaaactc tgatgaaatc cactgagacg ggcctcagaa aacttgaaat    1920
cttctaaaaa aaattcaagt ccatgcatga ttgaagcaaa cggtatagca acggtgttaa    1980
cctgatctag tgatctcttg taatccttaa cggccaccta ccacaggtag caaacggcgt    2040
cccctcctc gatatctccg cggcggcctc tggcttttc cgcggaattg cgcggtgggg    2100
acggattcct cgagaccgcg acacaaccgc ctttcgccgc tgggcccccac accgctcggt    2160
gccgtagcct cacgggactc tttctcccctc ctcccccgct ataaattggc ttcatccct    2220
ccttgcctca tccatccaaa tcccagtccc caatcccagc ccatcgtcgg agaaattcat    2280
agaagcgaag cgaatcctcg cgatcctctc aaggtagtgc gagttttcga ttcccctctc    2340
```

-continued

```
gacccctcgt atgctttccc tgtttgtgtt tcgtcgtagc gtttgattag gtatgctttc    2400
cctgtttgtg ttcgtcgtag cgtttgattt ggtatgcttt cccgttcgt gttcctcgta    2460 gtgtttgatt aggtcgtgtg aggcgatggc ctgctcgcat ccttcgatct gtagtcgatt    2520
tgcgggtcgt ggtgtagatc tgcgggctgt gatgaagtta tttggtgtga tcgtgctcgc    2580
ctgattctgc gggttggctc gagtagatat gatggttgga ccggttggtt tgtttaccgc    2640 gctaggggttg ggctgggatg atgttgcatg cgccgttgcg cgtgatcccg cagcaggact    2700
tgcgtttgat tgccagatct cgttacgatt atgtgatttg gtttggactt tttagatctg    2760
tagcttctgc ttatgtgcca gatgcgccta ctgctcatat gcctgatgat aatcataaat    2820
ggctgtggaa ctaactagtt gattgcggag tcatgtatca gctacaggtg tagggactag    2880
ctacaggtgt agggacttgc gtctaaattg tttggtcctg tactcatgtt gcaattatgc    2940
aatttagttt agattgtttg ttccactcat ctaggctgta aagggacac tgcttagatt    3000 gctgtttaat cttttttagta gattatatat tatattggta acttattacc cttattacat    3060
gccatacgtg acttctgctc atgcctgatg ataatcatag atcactgtgg aattaattag    3120
ttgattgttg aatcatgttt catgtacata ccacggcaca attgcttagt tccttaacaa    3180
atgcaaattt tactgatcca tgtatgattt gcgtggttct ctaatgtgaa atactatagc    3240
tacttgttag taagaatcag gttcgtatgc ttaatgctgt atgtgccttc tgctcatgcc    3300
tgatgataat catatatcac tggaattaat tagttgatcg tttaatcata tatcaagtac    3360
ataccatggc acaattttta gtcacttaac ccatgcagat tgaactggtc cctgcatgtt    3420
ttgctaaatt gttctatttc tgattagacc atatatcatg taatttttttt tttgggtaat    3480 ggttctccta ttttaaatgc tatatagttc tggtacttgt tagaaaaatc tgcttccata    3540
gtttagttgc ttatccctcg aattatgatg ctgagcagct gatcctatag ctttgtttca    3600
kgtatcaatt cttgtgttca acagtcagtt tttgttagat tcattgtaac ttatggtcgc    3660
ttactcttct ggtcctcaat gcttgcagat gcagattttc gttaagaccc tcactggcaa    3720
gaccatcacc cttgaggttg agtcctcaga cactattgac aatgtcaagg ctaagatcca    3780
ggacaaggaa ggcattcctc cagatcagca gaggctgaty tttgctggca agcagctcga    3840
ggatggccgt accctagctg actacaacat ccagaaggag tccaccctcc acctggtgct    3900
caggcttagg ggaggcatgc agattttcgt caagaccctc actggcaaga ctatcacgct    3960
tgaggtcgag tcttctgaca cgatcgacaa cgtgaaggcc aagatccagg acaaggaggg    4020 aatcccccccg gaccagcagc gtytcatttt cgctggcaag cagctcgagg atggccgcac    4080
cctcgctgac tacaacatcc agaaggagtc gactctccac cttgtgctca ggctcagggg    4140
tggcatgcag atcttcgtca gaccctcac tggcaagacc atcaccttgg aggtggagtc    4200
ctcggacacc attgacaatg tgaaggcgaa gatccaggac aaggagggca tcccccccgga    4260 ccagcagcgt ctcatyttcg ccggcaagca rcttgaggat ggccgcaccc ttgcgganta    4320
caacatccag aargagtcca cccttcacct ggtgctccgc cttcgtggtg gtatgcagat    4380
tttcgtcaag accctcaccg gcaagaccat cacccctggag gtggagtcct ctgacaccat    4440
tgacaatgtg aaggcgaaga tccaggataa ggagggcatc cccccggacc agcagcgtyt    4500
tatctttgct ggcaagcagc ttgaggatgg ccgcaccctg gcagantaca acatccagaa    4560
ggagtccacc cttcacctgg tgctccgcct tcgcggtggt atgcagatyt tcgtcaagac    4620
cctcaccggc aagaccatca cccctggaggt ggagtcctct gacaccatcg acaatgtgaa    4680
ggcgaagatc caggacaagg agggcatccc cccggaccag cagcgtctca tcttcgccgg    4740
```

-continued

```
caagcagctg gaggatggcc gcaccctggc agactacaac atccagaagg agtccactct    4800
ccacctggtg ctccgtctcc gtggtggcca gtaagtcctg ggccatgagc agctgtcctt    4860
ccagggttca caagtagtgg tgccttcttn ctgtccctcc gatggagatt atctgcatgt    4920
cgtggtcgtg tcctgatcga gtcgtcgttg agtccctatg ttttttcttc aagaaatgtg    4980
agtcctatgt cagtctggtt gcgtttgtga acattttctg ctgctgcgca gcagtttggt    5040
tggaactgtg caatgaaata aattgaaccc tggtttctgg ttatgtgtgt tagctaatgt    5100
ttttgaagtg gaagctntaa tcttntatcg cgttgctact acaattctgn ttgtgttttg    5160
atgttcttgt ttct                                                      5174
```

<210> SEQ ID NO 9
<211> LENGTH: 381
<212> TYPE: PRT
<213> ORGANISM: Saccharum Hybrid Cultivar H32-8560
<220> FEATURE:
<221> NAME/KEY: VARIANT
<222> LOCATION: (119)
<223> OTHER INFORMATION: The "Xaa" at position 119 is any amino acid.
<220> FEATURE:
<221> NAME/KEY: VARIANT
<222> LOCATION: (210)
<223> OTHER INFORMATION: The "Xaa" at position 210 is any amino acid.
<220> FEATURE:
<221> NAME/KEY: VARIANT
<222> LOCATION: (271)
<223> OTHER INFORMATION: The "Xaa" at position 271 is any amino acid.
<220> FEATURE:
<221> NAME/KEY: VARIANT
<222> LOCATION: (286)
<223> OTHER INFORMATION: The "Xaa" at position 286 is any amino acid.

<400> SEQUENCE: 9

```
Met Gln Ile Phe Val Lys Thr Leu Thr Gly Lys Thr Ile Thr Leu Glu
  1               5                  10                  15

Val Glu Ser Ser Asp Thr Ile Asp Asn Val Lys Ala Lys Ile Gln Asp
             20                  25                  30

Lys Glu Gly Ile Pro Pro Asp Gln Gln Arg Leu Ile Phe Ala Gly Lys
         35                  40                  45

Gln Leu Glu Asp Gly Arg Thr Leu Ala Asp Tyr Asn Ile Gln Lys Glu
     50                  55                  60

Ser Thr Leu His Leu Val Leu Arg Leu Arg Gly Gly Met Gln Ile Phe
 65                  70                  75                  80

Val Lys Thr Leu Thr Gly Lys Thr Ile Thr Leu Glu Val Glu Ser Ser
             85                  90                  95

Asp Thr Ile Asp Asn Val Lys Ala Lys Ile Gln Asp Lys Glu Gly Ile
            100                 105                 110

Pro Pro Asp Gln Gln Arg Xaa Ile Phe Ala Gly Lys Gln Leu Glu Asp
        115                 120                 125

Gly Arg Thr Leu Ala Asp Tyr Asn Ile Gln Lys Glu Ser Thr Leu His
    130                 135                 140

Leu Val Leu Arg Leu Arg Gly Gly Met Gln Ile Phe Val Lys Thr Leu
145                 150                 155                 160

Thr Gly Lys Thr Ile Thr Leu Glu Val Glu Ser Ser Asp Thr Ile Asp
                165                 170                 175

Asn Val Lys Ala Lys Ile Gln Asp Lys Glu Gly Ile Pro Pro Asp Gln
            180                 185                 190

Gln Arg Leu Ile Phe Ala Gly Lys Gln Leu Glu Asp Gly Arg Thr Leu
        195                 200                 205
```

```
Ala Xaa Tyr Asn Ile Gln Lys Glu Ser Thr Leu His Leu Val Leu Arg
    210                 215                 220
Leu Arg Gly Gly Met Gln Ile Phe Val Lys Thr Leu Thr Gly Lys Thr
225                 230                 235                 240
Ile Thr Leu Glu Val Glu Ser Ser Asp Thr Ile Asp Asn Val Lys Ala
                245                 250                 255
Lys Ile Gln Asp Lys Glu Gly Ile Pro Pro Asp Gln Gln Arg Xaa Ile
                260                 265                 270
Phe Ala Gly Lys Gln Leu Glu Asp Gly Arg Thr Leu Ala Xaa Tyr Asn
                275                 280                 285
Ile Gln Lys Glu Ser Thr Leu His Leu Val Leu Arg Leu Arg Gly Gly
            290                 295                 300
Met Gln Ile Phe Val Lys Thr Leu Thr Gly Lys Thr Ile Thr Leu Glu
305                 310                 315                 320
Val Glu Ser Ser Asp Thr Ile Asp Asn Val Lys Ala Lys Ile Gln Asp
                325                 330                 335
Lys Glu Gly Ile Pro Pro Asp Gln Gln Arg Leu Ile Phe Ala Gly Lys
                340                 345                 350
Gln Leu Glu Asp Gly Arg Thr Leu Ala Asp Tyr Asn Ile Gln Lys Glu
                355                 360                 365
Ser Thr Leu His Leu Val Leu Arg Leu Arg Gly Gly Gln
            370                 375                 380

<210> SEQ ID NO 10
<211> LENGTH: 3688
<212> TYPE: DNA
<213> ORGANISM: Saccharum Hybrid Cultivar 32-8560
<220> FEATURE:
<221> NAME/KEY: misc_feature
<222> LOCATION: (9)
<223> OTHER INFORMATION: The "n" at position 9 is any nucleotide.

<400> SEQUENCE: 10
aagttttgnt aaaatgaaca agaattggg gaaactatag ccaaagtggg tggggaatgg      60
tgccaaacaa aacttcgtaa accaacccaa aaagatccgg aaaacaaatg gatacgtgca    120
gggcatgcat gcaatagccc agccataaaa agcggcgagc caatgcccgg gtgtcaaaca    180
aaatggcgcc tgtgccggct ctggctgctt ccggctcagc tttcggaacg atccgccgca    240
gtttggcctc gcatatgatg acgatgatgg tctcctcttc tcgatttgta gctccggcat    300
gggagccacc tcctgtcggc tcacacatag cacgcgcctt agcccgtgct cgctctcccc    360
tagatgcttc acctgcgcca atcagtgtga gcccatcgtg tcagatggta ctcgtacgta    420
tggagtaacg tgataccaca acacgtacac tggtcagaat tgatagtata tgatcctgtc    480
gacccgatgt gttttagtac cttgcagtgg ccggagagga gtggccgcgc gcatgcggcg    540
cagggttct ccgcgctcgc tgatcgcttc ctcactgtgc gctcgtttag gaacaccacc     600
tcgtggtcgc tcaccatgtg tgactgcatg caacgctacg aatcaggacc cagatggaaa    660
cgaagcgcct ctcgaccacc tctgcctcgg tgatggttgg tgtgcagtgc gtacgcatgc    720
acgctaccaa tatcatacct ggatgccggt gcaatcgaac agcttcaggt tgtcgacgcg    780
gacggcgaag caggacgcgt acttccatat ctttgggttc cattacgtac cgtcaatcga    840
ataaataaag agaagagttt gagatcagct tgttgggagc aggtgaccgc ccgacatgca    900
tgccgattgt cgacggcacg gaaataaaca acacatttgt gagggagcca gggaggcagt    960
ggcggcacag cgtcgcggca cagtcgatgc agaagtggtt cttgtcgttc ttgcgctccc   1020
```

-continued

```
cccgggtgtg cagcgcacgc ctttgaaaaa ctccgatagc aggccacaca gccattgcgg    1080
ggcgccgcgc acggccgcca gctgcatccc cgtttgttcg cacatgcgct aggtggtcct    1140
gcggccgttc cttgcaccgc ggagacgcgg ggtggaccag tgggggaatg gatgaactgc    1200
tggtaggttt ggttggattg gcgagtgcgt agaggggggca tgggcaacga tagactcgat    1260
tcaattcaaa gactgaaaat agtggagttc taacaccatt ctgtgcggcg ctaattctcg    1320
acatggcagg cgtaagcata ataccgacat ggcatgcaac gatgttcgtg aacagtggtg    1380
acacatggat atggtggccg tccagggat tcgttccatt caattcaaag accgaaaatc    1440
gcggggttcc gtagcatttt gtgcggtgct aattctcgaa catgcgagac gtaagcctaa    1500
taccgagatg gcatgcaaca atgttcgtga acaacagtga cacgtggatg cggtggccgt    1560
ctagggattc gcgttctaag ctggtatatg tgcggtgtta attcttgaca tgcggggcgt    1620
aagtgtaata ccaagatgaa cggtgacacg tggacgcggg ggtcgtcaaa caattcattc    1680
cgtggtctag ggtaggttat atataaaggc cagtcttagt gggggatttt atggccatgt    1740
tattaatgca acccatattt ggaaaacagt gcaggaagag tttcatcttc gtaaaactct    1800
ctctaattcc atgaaactct tatcatctct ctcttcatca atacggtgcc acatcagcct    1860
atttaatgtc catgaaactc tgatgaaatc cactgagacg ggcctcagaa aacttgaaat    1920
cttctaaaaa aaattcaagt ccatgcatga ttgaagcaaa cggtatagca acggtgttaa    1980
cctgatctag tgatctcttg taatccttaa cggccaccta ccacaggtag caaacggcgt    2040
cccctcctc gatatctccg cggcggcctc tggcttttc gcggaattg gcggtgggg        2100
acggattcct cgagaccgcg acacaaccgc ctttcgccgc tgggccccac accgctcggt    2160
gccgtagcct cacgggactc tttctcccte ctcccccgct ataaattggc ttcatcccct    2220
ccttgcctca tccatccaaa tcccagtccc caatcccagc ccatcgtcgg agaaattcat    2280
agaagcgaag cgaatcctcg cgatcctctc aaggtagtgc gagttttcga ttcccctctc    2340
gacccctcgt atgctttccc tgtttgtgtt tcgtcgtagc gtttgattag gtatgctttc    2400
cctgtttgtg ttcgtcgtag cgtttgattt ggtatgcttt cccgttcgt gttcctcgta    2460
gtgtttgatt aggtcgtgtg aggcgatggc ctgctcgcat ccttcgatct gtagtcgatt    2520
tgcgggtcgt ggtgtagatc tgcgggctgt gatgaagtta tttggtgtga tcgtgctcgc    2580
ctgattctgc gggttggctc gagtagatat gatggttgga ccggttggtt tgtttaccgc    2640
gctagggttt ggctgggatg atgttgcatg cgccgttgcg cgtgatcccg cagcaggact    2700
tgcgtttgat tgccagatct cgttacgatt atgtgatttg gtttggactt tttagatctg    2760
tagcttctgc ttatgtgcca gatgcgccta ctgctcatat gcctgatgat aatcataaat    2820
ggctgtggaa ctaactagtt gattgcggag tcatgtatca gctacaggtg tagggactag    2880
ctacaggtgt agggacttgc gtctaaattg tttggtcctg tactcatgtt gcaattatgc    2940
aatttagttt agattgtttg ttccactcat ctaggctgta aagggacac tgcttagatt    3000
gctgtttaat cttttttagta gattatatat tatattggta acttattacc cttattacat    3060
gccatacgtg acttctgctc atgcctgatg ataatcatag atcactgtgg aattaattag    3120
ttgattgttg aatcatgttt catgtacata ccacggcaca attgcttagt tccttaacaa    3180
atgcaaattt tactgatcca tgtatgattt gcgtggttct ctaatgtgaa atactatagc    3240
tacttgttag taagaatcag gttcgtatgc ttaatgctgt atgtgccttc tgctcatgcc    3300
tgatgataat catatatcac tggaattaat tagttgatcg tttaatcata tatcaagtac    3360
ataccatggc acaattttta gtcacttaac ccatgcagat tgaactggtc cctgcatgtt    3420
```

-continued

| | |
|---|---|
| ttgctaaatt gttctatttc tgattagacc atatatcatg taattttttt tttgggtaat | 3480 |
| ggttctccta ttttaaatgc tatatagttc tggtacttgt tagaaaaatc tgcttccata | 3540 |
| gtttagttgc ttatccctcg aattatgatg ctgagcagct gatcctatag ctttgtttca | 3600 |
| kgtatcaatt cttgtgttca acagtcagtt tttgttagat tcattgtaac ttatggtcgc | 3660 |
| ttactcttct ggtcctcaat gcttgcag | 3688 |

<210> SEQ ID NO 11
<211> LENGTH: 2146
<212> TYPE: DNA
<213> ORGANISM: Lycopersicon esculentum
<220> FEATURE:
<221> NAME/KEY: misc_feature
<222> LOCATION: (16)
<223> OTHER INFORMATION: The "n" at position 16 is any nucleotide.

<400> SEQUENCE: 11

| | |
|---|---|
| agatctacaa ttatcngcaa cgtgttacac attttgtgct acaatatacc ttcaccattt | 60 |
| tgtgtatata taaaggttgc atctcttcaa acaaaaatca ctccatcaca acacaatgtc | 120 |
| ttcttcttct tctattacta ctactcttcc tttatgcacc aacaaatccc tctcttcttc | 180 |
| cttcaccacc accaactcat ccttgttatc aaaaccctct caacttttcc tccacggaag | 240 |
| gcgtaatcaa agtttcaagg tttcatgcaa cgcaaacaac gttgacaaaa accctgacgc | 300 |
| tgttgataga cgaaacgttc ttttagggtt aggaggtctt tatggtgcag ctaatcttgc | 360 |
| accattagcg actgctgcac ctataccacc tcctgatctc aagtcttgtg gtactgccca | 420 |
| tgtaaaagaa ggtgttgatg taatatacag ttgttgccct cctgtacccg atgatatcga | 480 |
| tagtgttccg tactacaagt tcccttctat gactaaactc cgcatccgcc ccctgctca | 540 |
| tgcggcggat gaggagtacg tagccaagta tcaattggct acgagtcgaa tgagggaact | 600 |
| tgataaagac ccctttgacc ctcttggctt taaacaacaa gctaatattc attgtgctta | 660 |
| ttgcaacggt gcttacaaag ttggtggcaa agaattgcaa gttcatttct cgtggctttt | 720 |
| cttttccttt catagatggt acttgtactt ttacgaaaga attttgggat cacttattaa | 780 |
| tgatccaact tttgctttac cttactggaa ttgggatcat ccaaaaggca tgcgtatacc | 840 |
| tcccatgttt gatcgtgagg gatcatctct ttacgatgag aaacgtaacc aaaatcatcg | 900 |
| caatggaact attattgatc ttggtcattt tggtaaggaa gttgacacac ctcagctaca | 960 |
| gataatgact aataatttaa ccctaatgta ccgtcaaatg gttactaatg ctccttgccc | 1020 |
| ttcccaattc ttcggtgctg cttacctctg ggttctgaac ccagtccggg tcagggtac | 1080 |
| tattgaaaac atccctcata ctccggttca catctgggacc ggtgacaaac ctcgtcaaaa | 1140 |
| aaacggtgaa gacatgggta atttctactc agccggttta gatccgattt tttactgcca | 1200 |
| ccatgccaat gtggacagga tgtggaatga atggaaatta attggcggga aagaaggga | 1260 |
| tttaacagat aaagattggt tgaactctga attcttttc tacgatgaaa atcgtaaccc | 1320 |
| ttaccgtgtg aaagtccgtg atgttttgga cagtaaaaaa atgggattcg attacgcgcc | 1380 |
| aatgcccact ccatggcgta atttttaaacc aatcagaaag tcatcatcag gaaaagtgaa | 1440 |
| tacagcgtca attgcaccag ttagcaaggt gttcccattg gcgaagctgg accgtgcgat | 1500 |
| ttcgttctct atcacgcggc cagcctcgtc aaggacaaca caagagaaaa atgagcagga | 1560 |
| ggagattctg acattcaata aaatatcgta tgatgatagg aactatgtaa ggttcgatgt | 1620 |
| gtttctgaac gtggacaaga ctgtgaatgc agatgagctt gataaggcgg agtttgcagg | 1680 |
| gagttatact agcttgccgc atgttcatgg aagtaatact aatcatgtta ccagtgttac | 1740 |

-continued

```
tttcaagctg gcgataactg aactgttgga ggatattgga ttggaagatg aagatactat    1800
cgcggtgact ttaattccaa aagctggcgg tgaaggtgta tccattgaaa gtgtggagat    1860
caagcttgag gattgttaaa gtctgcatga gttggtggct atggagccaa atttatgttt    1920
aattagtata attatgtgtg gtttgagtta tgttttatgt taaaatgtat cagctcgatc    1980
gatagctgat tgctagttgt gttaatgcta tgtatgaaat aaataaatgg ttgtcttcca    2040
ttcagtttat catttttgt cattctaatt aacggttaac ttttttttct actatttata    2100
cgaagctact atactatgta tatcatttgg aaaattatat attatt                  2146

<210> SEQ ID NO 12
<211> LENGTH: 3509
<212> TYPE: DNA
<213> ORGANISM: Zea mays

<400> SEQUENCE: 12
gaattccggc gtgggcgctg ggctagtgct cccgcagcga gcgatctgag agaacggtag      60
agttccggcc gggcgcgcgg gagaggagga gggtcgggcg gggaggatcc gatggccggg     120
aacgagtgga tcaatgggta cctggaggcg atcctcgaca gccacacctc gtcgcggggt     180
gccggcggcg gcggcggcgg gggggacccc aggtcgccga cgaaggcggc gagccccgc     240 ggcgcgcaca tgaacttcaa cccctcgcac tacttcgtcg aggaggtggt caagggcgtc     300
gacgagagcg acctccaccg gacgtggatc aaggtcgtcg ccacccgcaa cgcccgcgag     360
cgcagcacca ggctcgagaa catgtgctgg cggatctggc acctcgcgcg caagaagaag     420
cagctggagc tggagggcat ccagagaatc tcggcaagaa ggaaggaaca ggagcaggtg     480
cgtcgtgagg cgacggagga cctggccgag gatctgtcag aaggcgagaa gggagacacc     540
atcggcgagc ttgcgccggt tgagacgacc aagaagaagt tccagaggaa cttctctgac     600
cttaccgtct ggtctgacga caataaggag aagaagcttt acattgtgct catcagcgtg     660
catggtcttg ttcgtggaga aaacatggaa ctaggtcgtg attctgatac aggtggccag     720
gtgaaatatg tggtcgaact tgcaagagcg atgtcaatga tgcctggagt gtacagggtg     780
gacctcttca ctcgtcaagt gtcatctcct gacgtggact ggagctacgg tgagccaacc     840
gagatgttat cgccggttc caatgatgga gaggggatgg tgagagtgg cggagcctac     900 attgtgcgca taccgtgtgg gccgcgggat aaatacctca agaaggaagc gttgtggcct     960
tacctccaag agtttgtcga tggagcccct gcgcatatcc tgaacatgtc caaggctctg    1020
ggagagcagg ttggaaatgg gaggccagta ctgccttacg tgatacatgg cactatgcc     1080 gatgctggga tgttgctgc tctccttct ggtgcgctga atgtgccaat ggtgctcact    1140
ggccactcac ttgggaggaa caagctggaa caactgctga agcaagggcg catgtccaag    1200
gaggagatcg attcgacata caagatcatg aggcgtatcg agggtgagga gctggccctg    1260
gatgcgtcag agcttgtaat cacgagcaca aggcaggaga ttgatgagca gtgggattg    1320 tacgatggat ttgatgtcaa gcttgagaaa gtgctgaggg cacgggcgag gcgcggggtt    1380
agctgccatg gtcgttacat gcctaggatg gtggtgattc ctccgggaat ggatttcagc    1440
aatgttgtag ttcatgaaga cattgatggg gatggtgacg tcaaagatga tatcgttggt    1500
ttggagggtg cctcacccaa gtcaatgccc ccaatttggg ccgaagtgat gcggttcctg    1560
accaaccctc acaagccgat gatcctggcc ttatcaagac cagacccgaa gaagaacatc    1620
actaccctcg tcaaagcgtt tggagagtgt cgtccactca gggaacttgc aaaccttact    1680
ctgatcatgg gtaacagaga tgacatcgac gacatgtctg ctggcaatgc cagtgtcctc    1740
```

```
accacagttc tgaagctgat tgacaagtat gatctgtacg gaagcgtggc gttccctaag    1800
catcacaatc aggctgacgt cccggagatc tatcgcctcg cggccaaaat gaagggcgtc    1860
ttcatcaacc ctgctctcgt tgagccgttt ggtctcaccc tgatcgaggc tgcggcacac    1920
ggactcccga tagtcgctac caagaatggt ggtccggtcg acattacaaa tgcattaaac    1980
aacggactgc tcgttgaccc acacgaccag aacgccatcg ctgatgcact gctgaagctt    2040
gtggcagaca agaacctgtg gcaggaatgc cggagaaacg ggctgcgcaa catccacctc    2100
tactcatggc cggagcactg ccgcacttac ctcaccaggg tggccgggtg ccggttaagg    2160
aacccgaggt ggctgaagga cacaccagca gatgccggag ccgatgagga ggagttcctg    2220
gaggattcca tggacgctca ggacctgtca ctccgtctgt ccatcgacgg tgagaagagc    2280
tcgctgaaca ctaacgatcc actgtggttc gaccccagg atcaagtgca aagatcatg     2340 aacaacatca agcagtcgtc agcgcttcct ccgtccatgt cctcagtcgc agccgagggc    2400
acaggcagca ccatgaacaa atacccactc ctgcgccggc gccggcgctt gttcgtcata    2460
gctgtggact gctaccagga cgatggccgt gctagcaaga agatgctgca ggtgatccag    2520
gaagttttca gagcagtccg atcggactcc cagatgttca agatctcagg gttcacgctg    2580
tcgactgcca tgccgttgtc cgagacactc cagcttctgc agctcggcaa gatcccagcg    2640
accgacttcg acgccctcat ctgtggcagc ggcagcgagg tgtactatcc tggcacggcg    2700
aactgcatgg acgctgaagg aaagctgcgc ccagatcagg actatctgat gcacatcagc    2760
caccgctggt cccatgacgg cgcgaggcag accatagcga agctcatggg cgctcaggac    2820
ggttcaggcg acgctgtcga gcaggacgtg gcgtccagta atgcacactg tgtcgcgttc    2880
ctcatcaaag accccaaaa ggtgaaaacg gtcgatgaga tgagggagcg gctgaggatg     2940
cgtggtctcc gctgccacat catgtactgc aggaactcga caaggcttca ggttgtccct    3000
ctgctagcat caaggtcaca ggcactcagg tatctttccg tgcgctgggg cgtatctgtg    3060
gggaacatgt atctgatcac cggggaacat ggcgacaccg atctagagga gatgctatcc    3120
gggctacaca agaccgtgat cgtccgtggc gtcaccgaga agggttcgga agcactggtg    3180
aggagcccag gaagctacaa gagggacgat gtcgtcccgt ctgagacccc cttggctgcg    3240
tacacgactg tgagctgaa ggccgacgag atcatgcggg ctctgaagca agtctccaag     3300
acttccagcg gcatgtgaat ttgatgcttc ttttacattt tgtccttttc ttcactgcta    3360
tataaaataa gttgtgaaca gtaccgcggg tgtgtatata tatattgcag tgacaaataa    3420
aacaggacac tgctaactat actggtgaat atacgactgt caagattgta tgctaagtac    3480
tccatttctc aatgtatcaa tcggaattc                                      3509
```

<210> SEQ ID NO 13
<211> LENGTH: 10
<212> TYPE: DNA
<213> ORGANISM: Saacharum Hybrid Cultivar H32-8560
<220> FEATURE:
<221> NAME/KEY: misc_feature
<222> LOCATION: (9)
<223> OTHER INFORMATION: The "n" at position 9 is any nucleotide.

<400> SEQUENCE: 13 aagttttgnt                                                           10

<210> SEQ ID NO 14
<211> LENGTH: 10
<212> TYPE: DNA
<213> ORGANISM: Saccharum Hybrid Cultivar H32-8560

```
<220> FEATURE:
<221> NAME/KEY: misc_feature
<222> LOCATION: (9)
<223> OTHER INFORMATION: The "n" at position 9 is any nucleotide.

<400> SEQUENCE: 14 aagctttgnt                                                            10

<210> SEQ ID NO 15
<211> LENGTH: 10
<212> TYPE: DNA
<213> ORGANISM: Saccharum Hybrid Cultivar H32-8560
<220> FEATURE:
<221> NAME/KEY: misc_feature
<222> LOCATION: (10)
<223> OTHER INFORMATION: The "n" at position 10 is any nucleotide.

<400> SEQUENCE: 15 aagcttttgn                                                            10

<210> SEQ ID NO 16
<211> LENGTH: 10
<212> TYPE: DNA
<213> ORGANISM: Saccharum Hybrid Cultivar H32-8560
<220> FEATURE:
<221> NAME/KEY: misc_feature
<222> LOCATION: (9)
<223> OTHER INFORMATION: The "n" at position 9 is any nucleotide.

<400> SEQUENCE: 16 aagttttgnt                                                            10

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence:  Unknown

<400> SEQUENCE: 17

Leu Gly Asn Ala Gly Thr Ala
 1               5
```